United States Patent [19]

Eggler et al.

[11] Patent Number: 4,486,428

[45] Date of Patent: Dec. 4, 1984

[54] BICYCLIC BENZO FUSED COMPOUNDS

[75] Inventors: James F. Eggler, Stonington; Michael R. Johnson, Gales Ferry; Lawrence S. Melvin, Jr., Ledyard, all of Conn.

[73] Assignee: Pfizer Inc., New York, N.Y.

[21] Appl. No.: 457,171

[22] Filed: Jan. 13, 1983

Related U.S. Application Data

[63] Continuation-in-part of Ser. No. 358,751, Mar. 16, 1982, abandoned.

[51] Int. Cl.$^3$ .................. A61K 31/35; C07D 311/58
[52] U.S. Cl. ................. 424/248.4; 546/330; 546/331; 424/248.5; 546/333; 546/334; 424/248.51; 544/121; 544/124; 424/248.52; 544/129; 544/131; 424/248.53; 544/132; 544/141; 424/248.54; 544/146; 544/150; 424/248.55; 544/151; 544/357; 424/248.56; 544/360; 544/365; 424/248.57; 544/366; 544/372; 424/250; 544/376; 544/378; 424/263; 548/252; 548/517; 424/267; 548/523; 548/524; 424/268; 548/531; 549/60; 424/269; 549/72; 549/281; 424/274; 549/386; 549/407; 424/275; 424/279; 424/283; 546/187; 546/188; 546/189; 546/190; 546/191; 546/194; 546/195; 546/196; 546/197; 546/256; 546/262; 546/266; 546/269; 546/270; 546/323
[58] Field of Search ................. 549/407, 386, 281, 60; 546/187, 194, 197, 256, 269, 270; 548/252, 517, 523, 524; 544/360, 365, 366, 372, 376, 378, 357, 121, 129, 131, 124, 132, 141, 146, 150, 151; 424/279, 283, 275, 248.4, 248.5, 248.51, 248.52, 248.53, 248.54, 248.55, 248.56, 248.57, 250, 263, 267, 268, 269, 274

[56] References Cited

U.S. PATENT DOCUMENTS

| | | | |
|---|---|---|---|
| 4,087,545 | 5/1978 | Archer et al. | 424/283 |
| 4,143,139 | 3/1979 | Bindra | 424/248.55 |
| 4,152,450 | 5/1979 | Day et al. | 424/283 |
| 4,188,495 | 2/1980 | Althuis et al. | 568/633 |
| 4,210,663 | 7/1980 | Belletire | 549/407 |
| 4,228,169 | 10/1980 | Johnson et al. | 424/258 |
| 4,235,913 | 11/1980 | Johnson et al. | 424/263 |
| 4,260,764 | 4/1981 | Johnson | 546/153 |

Primary Examiner—Nicky Chan
Attorney, Agent, or Firm—Charles J. Knuth; Albert E. Frost; Paul D. Thomas

[57] ABSTRACT

Bicyclic fused benzenoid compounds of the formula

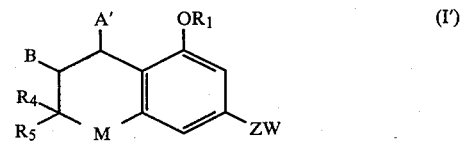

(I')

and pharmaceutically acceptable cationic and acid addition salts thereof, where M is O, $CH_2$ or $NR_6$; $R_6$ is hydrogen, formyl, carbobenzyloxy or certain carboalkoxyalkyl, alkanoyl, alkyl, aralkyl or aralkylcarbonyl groups;

A' is:
(1) A where one of A and B is hydrogen such that when A is hydrogen, B is $C(R_2R_3)(CH_2)_fQ$ and f is 1 or 2; when B is hydrogen, A is $C(R_2R_3)(CH_2)_fQ$ and f is 0 or 1, when taken together A and $OR_1$ form a lactone or certain derivatives thereof;
(2) A' is

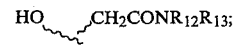

(3) A' is $Q_3$;
Q is $CO_2R_7$, $COR_8$, $C(OH)R_8R_9$, CN, $CONR_{12}R_{13}$, $CH_2NR_{12}R_{13}$, $CH_2NHCOR_{14}$, $CH_2NHSO_2R_{17}$ or 5-tetrazoyl;
$Q_3$ is

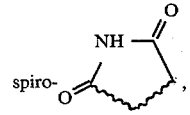

5-tetrazolyl, $CH_2CONHCOR_7$, COOH or certain ester, amide, carboximido or sulfonimido derivatives thereof, CONHOH, $CONHCONH_2$, or $COCH_2Q_4$ where $Q_4$ is CN or COOH or certain esters thereof;
$R_1$ is hydrogen, benzyl or certain acyl groups; $R_4$ is hydrogen, certain alkyl or certain aralkyl groups; $R_5$ is hydrogen or certain alkyl groups; Z is $(C_1-C_9)$ alkylene, optionally interrupted by O, S, SO or $SO_2$; and W is hydrogen, methyl, certain aryl or cycloalkyl groups; useful in mammals as analgesics, tranquilizers, antiemetic agents, diuretics, anticonvulsants, antidiarrheals, antitussives, in treatment of glaucoma, and intermediates therefore.

14 Claims, No Drawings

BICYCLIC BENZO FUSED COMPOUNDS

CROSS REFERENCE TO RELATED APPLICATION

This application is a continuation-in-part of copending application Ser. No. 358,751 filed Mar. 16, 1982, now abandoned.

BACKGROUND OF THE INVENTION

1. Field of the Invention

This invention relates to certain novel bicyclic benzo fused compounds, more particularly to certain 5-hydroxy-7-substituted-3,4-dihydro-2H-benzopyrans which are also substituted at the 3-position or the 4-position, the corresponding tetrahydroquinoline and tetralin analogs and derivatives thereof and pharmaceutically acceptable cationic and acid addition salts thereof, useful as CNS agents, especially as analgesic, antidiarrheals, and antiemetic agents for use in mammals, including man; methods for their use and pharmaceutical compositions containing them.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesics such as d-propoxyphene, codeine, and morphine, possess addictive liability. The need for improved and potent analgesics is, therefore, evident.

A series of analgesic dibenzo[b,d]pyrans, having at the 9-position substituents such as alkyl, hydroxy and oxo, are disclosed in U.S. Pat. Nos. 3,507,885; 3,636,058; 3,649,650; 3,856,821; 3,928,598; 3,944,673, 3,953,603 and 4,143,139. Particularly of interest is dl-trans-1-hydroxy-3-(1,1-dimethylheptyl)-6,6-dimethyl-6,6a,7,8,10,10a-hexahydro-9H-dibenzo[b,d]pyran-9-one, an antiemetic, antianxiety agent with analgesic properties in animals, now generally referred to as nabilone.

U.S. Pat. No. 4,152,450 discloses certain 3-alkyl-1-hydroxytetrahydro and hexahydrodibenzo[b,d]pyrans, having an amino or amido group at the 9-position, which are useful as analgesics, antidepressants, antianxiety agents and hypotensive agents.

U.S. Pat. No. 4,188,495 discloses analgesic 1,9-dihydroxyoctahydrophenanthrenes, 1-hydroxyoctahydrophenanthren-9-ones and derivatives thereof of the formula

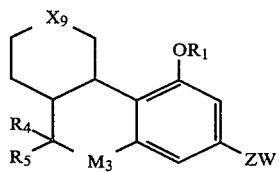

where $X_9$ is CHOH or C=O, $M_3$ is $CH_2$ and $R_1$, $R_4$, $R_5$, Z and W are as defined below.

U.S. Pat. No. 4,260,764, issued Apr. 7, 1981, discloses compounds of the above formula wherein $M_3$ is $NR_6$ and $X_9$, $R_1$, $R_4$, $R_5$, $R_6$, Z and W are as defined above. They are useful as analgesics, tranquilizers, hypotensives, diuretics and as agents for treatment of glaucoma.

U.S. Pat. No. 4,228,169, issued Oct. 14, 1980, discloses the same compounds to be useful as antiemetic agents.

Bergel et al., J. Chem. Soc., 286 (1943) investigated the replacement of the pentyl group at the 3-position of 7,8,9,10-tetrahydro-3-pentyl-6,6,9-trimethyl-6H-dibenzo[b,d]pyran-1-ol by alkoxy groups of four to eight carbon atoms and found that these compounds had little or no hashish activity at 10 to 20 mg/kg.

In a more recent study, Loev et al., J. Med. Chem., 16, 1200–1206 (1973) report a comparison of 7,8,9,10-tetrahydro-3-substituted-6,6,9-trimethyl-6H-dibenzo[b,d]-pyran-1-ols in which the 3-substituent is —OCH($CH_3$)$C_5H_{11}$; —$CH_2CH(CH_3)C_5H_{11}$; or —CH($CH_3$)$C_5H_{11}$. The ether side chain containing compound was 50% less active in central nervous system activity than the corresponding compound in which the alkyl side chain is directly attached to the aromatic ring, rather than through an intervening oxygen atom; and 5 times as active as the compound in which oxygen is replaced by methylene.

Mechoulam and Edery in "Marijuana", edited by Mechoulam, Academic Press, New York, 1973, page 127, observe that major structural changes in the tetrahydrocannabinol molecule seem to result in steep reductions in analgesic activity.

U.S. Pat. No. 4,087,545 discloses the antiemetic and antinausea properties of 1-hydroxy-3-alkyl-6,6a,7,8,10,-10a-hexahydro-9H-dibenzo[b,d]pyran-9-ones.

Sallan et al., N. E. J. Med. 293, 795 (1975) reported oral delta-9-tetrahydrocannabinol has antiemetic properties in patients receiving cancer chemotherapy.

Delta-9-tetrahydrocannibinol is reported by Shannon et al. (Life Sciences 23, 49–54, 1978) to lack antiemetic effects in apomorphine-induced emesis in the dog. Borison et al., N. England J. of Med. 298, 1480 (1978) report the use of unanesthetized cats as an animal model for determining the antiemetic effect of compounds especially in connection with emesis induced by cancer chemotherapy drugs. They found that pretreatment of unanesthetized cats with 1-hydroxy-3-(1',1'-dimethylheptyl)-6,6-dimethyl-6,6a,7,8,10,10a-hexahydro-9H-dibenzo[b,d]pyran-9(8H)-one (nabilone) affords pronounced protection against vomiting per se after injection of antineoplastic drugs.

Starting materials of the formulae below, useful for preparation of the invention compounds of formula (I) are known in the art.

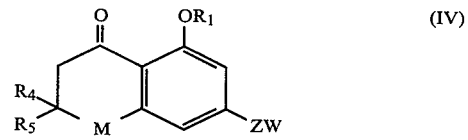

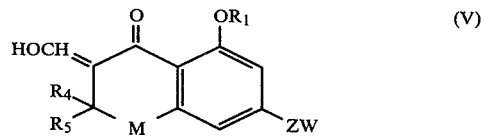

where $R_1$, $R_4$, $R_5$, M, Z and W are as defined below. Detailed procedures for the preparation of said starting compounds wherein M is O are set forth in U.S. Pat. No. 4,143,139, issued Mar. 6, 1979 and U.S. Pat. No. 4,235,913, issued Nov. 25, 1980, each of which is hereby incorporated by reference. Similarly, detailed procedures for preparation of the above starting materials wherein M is $CH_2$ are set forth in U.S. Pat. No. 4,188,495, issued Feb. 12, 1980; and wherein M is $NR_6$, and $R_6$ is as defined herein are set forth in U.S. Pat. No. 4,228,169, issued Oct. 14, 1980, and U.S. Pat. No. 4,260,764, issued Apr. 7, 1981, each of which are also hereby incorporated by reference.

SUMMARY OF THE INVENTION

It has now been found that certain 3,4-dihydro-2H-benzopyrans, 1,2,3,4-tetrahydroquinolines, corresponding tetralins and derivatives thereof of the formula (I) are effective agents, useful in mammals as tranquilizers, anticonvulsants, diuretics, antidiarrheals, antitussives and as agents for treatment of glaucoma. They are particularly effective in mammals, including man, as analgesics, antidiarrheals and as agents for treatment and prevention of emesis and nausea, especially that induced by antineoplastic drugs. Said invention compounds, which are nonnarcotic and free of addiction liability, are of the formula

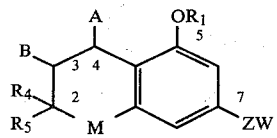

and pharmaceutically acceptable cationic and acid addition salts thereof;

wherein M is O, $CH_2$ or $NR_6$;

$R_6$ is a member selected from the group consisting of hydrogen, $—(CH_2)_y—$carbalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms; $—(CH_2)_xC_6H_5$ wherein x is an integer from 1 to 4; and $—CO(CH_2)_{x-1}C_6H_5$;

one of A and B is hydrogen and the other is

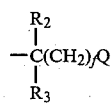

such that when A is hydrogen f is 1 or 2 and when B is hydrogen f is zero or 1; $R_2$ and $R_3$ are each hydrogen, methyl or ethyl; Q is selected from the group consisting of $CO_2R_7$, $COR_8$, $C(OH)R_8R_9$, CN, $CONR_{12}R_{13}$, $CH_2NR_{12}R_{13}$, $CH_2NHCOR_{14}$, $CH_2NHSO_2R_{17}$ and 5-tetrazolyl;

A and $OR_1$ when taken together form

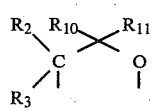

where $R_{10}$ is hydrogen and $R_{11}$ is hydroxy or alkoxy having from one to four carbon atoms or taken together $R_{10}$ and $R_{11}$ are an oxygen atom;

$R_1$ is a member selected from the group consisting of hydrogen, benzyl, benzoyl, alkanoyl having from one to five carbon atoms and $—CO—(CH_2)_p—NR_{15}R_{16}$ wherein p is 0 or an integer from 1 to 4; each of $R_{15}$ and $R_{16}$ when taken individually is selected from the group consisting of hydrogen and alkyl having from one to four carbon atoms; $R_{15}$ and $R_{16}$ when taken together with the nitrogen atom to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_4$ is hydrogen, alkyl having from 1 to 6 carbon atoms or $—(CH_2)_z—C_6H_5$ wherein z is an integer from 1 to 4;

$R_5$ is hydrogen, methyl or ethyl;

$R_7$ is hydrogen, alkyl having from one to four carbon atoms or benzyl;

$R_8$ and $R_9$ are each hydrogen, alkyl having from one to four carbon atoms, phenyl or benzyl;

when taken separately, $R_{12}$ and $R_{13}$ are each hydrogen, alkyl having from one to six carbon atoms, phenyl or benzyl; $R_{12}$ and $R_{13}$ when taken together with the nitrogen atom to which they are attached form a 5- or 6-membered heterocyclic ring selected from the group consisting of piperidino, pyrrolidino, morpholino and N-alkylpiperazino having from one to four carbon atoms in the alkyl group;

$R_{14}$ is hydrogen, alkyl having from one to four carbon atoms, trifluoromethyl, benzyl, furyl, thienyl, pyridyl or $R_{18}C_6H_4$ where $R_{18}$ is H, $NH_2$, F, Cl, Br, $CH_3$ or $OCH_3$;

$R_{17}$ is alkyl having from one to six carbon atoms, benzyl, or $R_{18}C_6H_4$;

Z is selected from the group consisting of
(a) alkylene having from one to nine carbon atoms;
(b) $—(alk_1)_m—X—(alk_2)_n—$ wherein each of $(alk_1)$ and $(alk_2)$ is alkylene having from one to nine carbon atoms, with the proviso that the summation of carbon atoms in $(alk_1)$ plus $(alk_2)$ is not greater than nine; each of m and n is 0 or 1; X is selected from the group consisting of O, S, SO and $SO_2$; and W is selected from the group consisting of hydrogen, methyl, pyridyl, piperidyl,

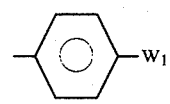

wherein $W_1$ is selected from the group consisting of hydrogen, fluoro and chloro; and

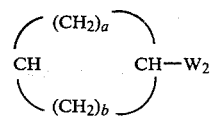

wherein $W_2$ is selected from the group consisting of hydrogen and

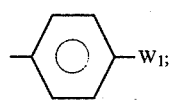

a is an integer from 1 to 5 and b is 0 or an integer from 1 to 5; with the proviso that the sum of a and b is not greater than 5.

Particularly preferred compounds of formula (I) are those wherein:
$R_1$ is hydrogen or alkanoyl, especially hydrogen or acetyl;
$R_4$ is hydrogen or said alkyl,
$R_5$ is hydrogen or methyl,
M is O, $CH_2$ or $NR_6$ where $R_6$ is hydrogen or said alkyl,
Z is said alkylene or —$(alk_1)_m$—O—$(alk_2)_n$— and W is hydrogen or phenyl.

When B is hydrogen and A is $R_2R_3C(CH_2)_fQ$, particularly preferred compounds of the invention are those wherein:
f is zero,
$R_2$ and $R_3$ are each hydrogen,
Q is $COOR_7$, especially those where $R_7$ is hydrogen, methyl or ethyl; $C(OH)R_8R_9$, especially where $R_8$ and $R_9$ are each hydrogen or methyl; CHO or $CH_2NHCOR_{14}$. Especially preferred are such compounds wherein $R_4$ and $R_5$ are each methyl, Z is alkylene and W is hydrogen or Z is O—$(alk_2)_n$— and W is hydrogen or phenyl. Particularly preferred values for ZW are $OCH(CH_3)(CH_2)_3C_6H_5$ and $C(CH_3)_2(CH_2)_5CH_3$. More particularly preferred such compounds are those wherein M is O, $R_1$ is hydrogen or acetyl and Q and ZW are as tabulated below.

| Q | ZW |
|---|---|
| $CH_2NHCOCH_3$ | $OCH(CH_3)(CH_2)_3C_6H_5$ |
| CHO | $OCH(CH_3)(CH_2)_3C_6H_5$ |
| $CH_2OH$ | $OCH(CH_3)(CH_2)_3C_6H_5$ |
| $COOCH_3$ | $C(CH_3)_2(CH_2)_5CH_3$ |
| CHO | $C(CH_3)_2(CH_2)_5CH_3$ |
| $C(CH_3)_2OH$ | $C(CH_3)_2(CH_2)_5CH_3$ |
| $CH(CH_3)OH$ | $C(CH_3)_2(CH_2)_5CH_3$ |
| $CH_2OH$ | $C(CH_3)_2(CH_2)_5CH_3$ |

Most particularly preferred are the above compounds wherein A is $CH_2CH_2NHCOCH_3$, $R_1$ is acetyl, $R_4$ and $R_5$ are each methyl and ZW is $OCH(CH_3)(CH_2)_3C_6H_5$; and the compound wherein A is $CH_2CH_2OH$, $R_1$ is hydrogen, $R_4$ and $R_5$ are each methyl and ZW is $C(CH_3)_2(CH_2)_5CH_3$.

When A is hydrogen and B is $R_2R_3C(CH_2)_fQ$, particularly preferred compounds of formula (I) are those wherein:
f is one,
$R_2$ and $R_3$ are each hydrogen,
Q is $COOR_7$, especially where $R_7$ is hydrogen, methyl or ethyl;
$C(OH)R_8R_9$, especially where $R_8$ and $R_9$ are each hydrogen or methyl.

Of the above group of compounds wherein A is hydrogen, particularly preferred values for the remaining substituents are: $R_1$ is hydrogen or acetyl, $R_4$ and $R_5$ are each methyl and ZW is $OCH(CH_3)(CH_2)_3C_6H_5$. More particularly preferred are such compounds wherein M is O and Q is $COOCH_3$ or $CH_2OH$; and most particularly the latter compound wherein $R_1$ is hydrogen, i.e., the compound of formula (I) where A is H, B is $CH_2CH_2OH$, $R_1$ is H, $R_4$ and $R_5$ are each methyl and ZW is $OCH(CH_3)(CH_2)_3C_6H_5$.

The scope of the present invention also includes valuable analgesic, antidiarrheals and antiemetic agents of the formulae below

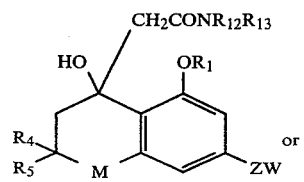

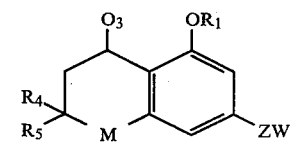

where $Q_3$ is 5-tetrazolyl, $COOR_7$, CONHOH, CONHCONH$_2$, $CONR_{12}R_{13}$, $CONHCOR_{19}$, $CONHSO_2R_{17}$, $CH_2CONHCOR_{19}$,

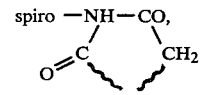

CONHAr or $COCH_2Q_4$ where Ar is

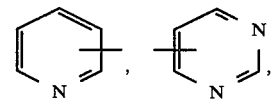

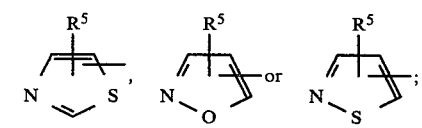

$Q_4$ is CN or $COOR_5$; $R_{19}$ is $R_7$, phenyl or phenylethyl; and M, $R_1$, $R_4$, $R_5$, $R_7$, $R_{12}$, $R_{13}$, $R_{17}$, Z and W are as previously defined.

The invention further provides compounds of the formulae below which are intermediates useful in preparation of the compounds of formula (I)

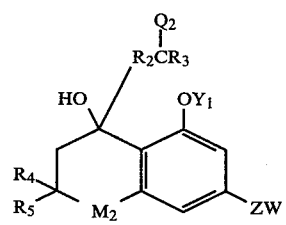

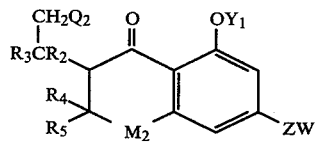

where $R_2$, $R_3$, $R_4$, $R_5$, Z and W are as defined above, $M_2$ is O, $CH_2$ or $NR_{60}$ where $R_{60}$ is formyl, alkanoyl having from two to five carbon atoms, alkyl having from one to six carbon atoms or benzyl; $Q_2$ is CN or $COOR_7$ where $R_7$ is as defined above; $Y_1$ is hydrogen, alkyl having from one to four carbon atoms, benzyl, benzoyl or alkanoyl having from one to five carbon atoms.

For the valuable intermediates of formula (VI) particularly preferred values are $Q_2$ is $COOR_7$, $Y_1$ is benzyl. The particularly preferred values for $R_2$–$R_5$, Z and W are as stated above for compounds of formula (I). A particularly preferred value for $M_2$ is O.

For the intermediates of formula (VII) a particularly preferred value for $Y_1$ is hydrogen. Particularly preferred values for $Q_2$, $M_2$, $R_2$–$R_5$, Z and W are as stated above for compounds (VI).

Also included in this invention are pharmaceutically acceptable cationic and acid addition salts of the compounds of formulae (I), (XVIII) and (XIX). By pharmaceutically acceptable cationic salts of the compounds of the invention is meant the salts of those compounds of formulae (I), (XVIII) and (XIX), where A or B contains a carboxylic acid group, said salts are formed by neutralization of the carboxylic acid by bases of pharmaceutically acceptable metals, ammonia and amines. Examples of such metals are sodium, potassium, calcium and magnesium. Examples of such amines are ethanolamine and N-methylglucamine.

By the term pharmaceutically acceptable acid addition salts is meant the addition salts formed between those compounds of formulae (I), (XVIII) and (XIX), having one or more basic nitrogen atoms in substituents M, $R_1$, A, B or $Q_3$ and a pharmaceutically acceptable acid. Examples of such acids are acetic, benzoic, hydrobromic, hydrochloric, citric, sulfosalicylic, tartaric, glycolic, malonic, maleic, fumaric, malic, 2-hydroxy-3-naphthoic, pamoic, salicylic, phthalic, succinic, gluconic, mandelic, lactic, sulfuric, phosphoric, nitric and methanesulfonic acids. Of course, when more than one basic nitrogen atom is present in the free base of formula (I), mono-, di- or higher addition salts may be obtained by employing one, two or more equivalents of acid to form the desired acid addition salt.

Compounds having the formulae (I), (XVIII) or (XIX) above, contain asymmetric centers at the 3- or 4-position (A, B or $Q_3$). There may be additional asymmetric centers at the 2-position ($R_4$, $R_5$), in the 7-position substituent (ZW), in the 1-position substituent ($R_6$) in compounds wherein M is $NR_6$, in substituent A or B and in the 2-position substituent ($R_4$). The present invention includes the racemates of formulae (I), (XVIII) and (XIX), the diastereomeric mixtures, pure enantiomers and diastereomers thereof. The utility of the racemic mixtures, the diastereomeric mixtures, as well as of the pure enantiomers and diastereomers is determined by the biological evaluations described below.

As mentioned above, the compounds of the invention are particularly useful as analgesics, antidiarrheals and as antiemetic and antinausea agents for use in mammals, including man. The invention further provides a method for producing analgesia in mammals and a method for prevention and treatment of nausea in a mammal subject to nausea, in each case by oral or parenteral administration of an effective amount of a compound of formula (I), (XVIII), (XIX) or their pharmaceutically acceptable salts.

Also provided are pharmaceutical compositions for use as analgesics, as well as those suitable for use in prevention and treatment of nausea, comprising an effective amount of compound of the invention and a pharmaceutically acceptable carrier.

DETAILED DESCRIPTION OF THE INVENTION

The compounds of the invention of formula (I) wherein B is hydrogen are defined by the formula below where f is zero or one;

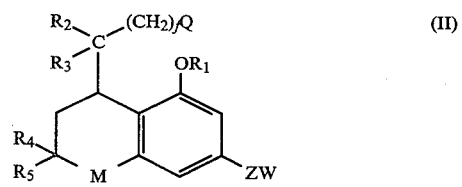

those wherein A is hydrogen by the formula

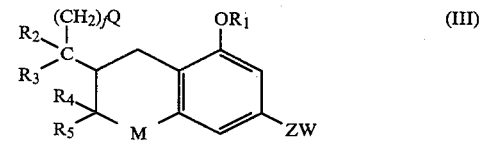

where f is 1 or 2; and $R_1$–$R_5$, M, Q, Z and W are as defined above, in each case.

The compounds of formula (II) wherein f is zero are prepared, for example, by methods outlined in Flow Charts A and B.

Flow Chart A illustrates methods which are employed to provide compounds of formula (II) wherein f is zero. The requisite starting ketones of formula (IVA) are provided in U.S. Pat. No. 4,143,139 ($M_2$=O), U.S. Pat. No. 4,188,495 ($M_2$=$CH_2$), U.S. Pat. No. 4,228,169 and U.S. Pat. No. 4,260,764 ($M_2$=$NR_{60}$), which, as noted above, are each incorporated by reference.

FLOW CHART A
For compounds of formula (II) wherein f is zero:

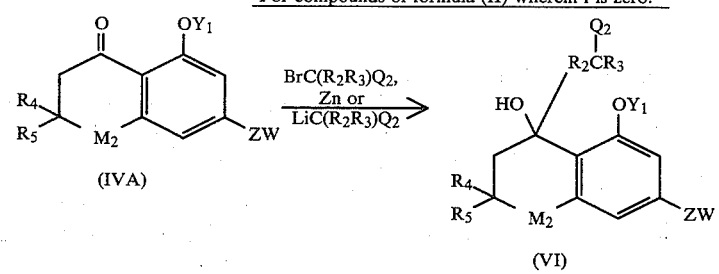

($M_2$ = O, $CH_2$ or $NR_{60}$, $R_{60}$, defined above)

FLOW CHART A
-continued
For compounds of formula (II) wherein f is zero:

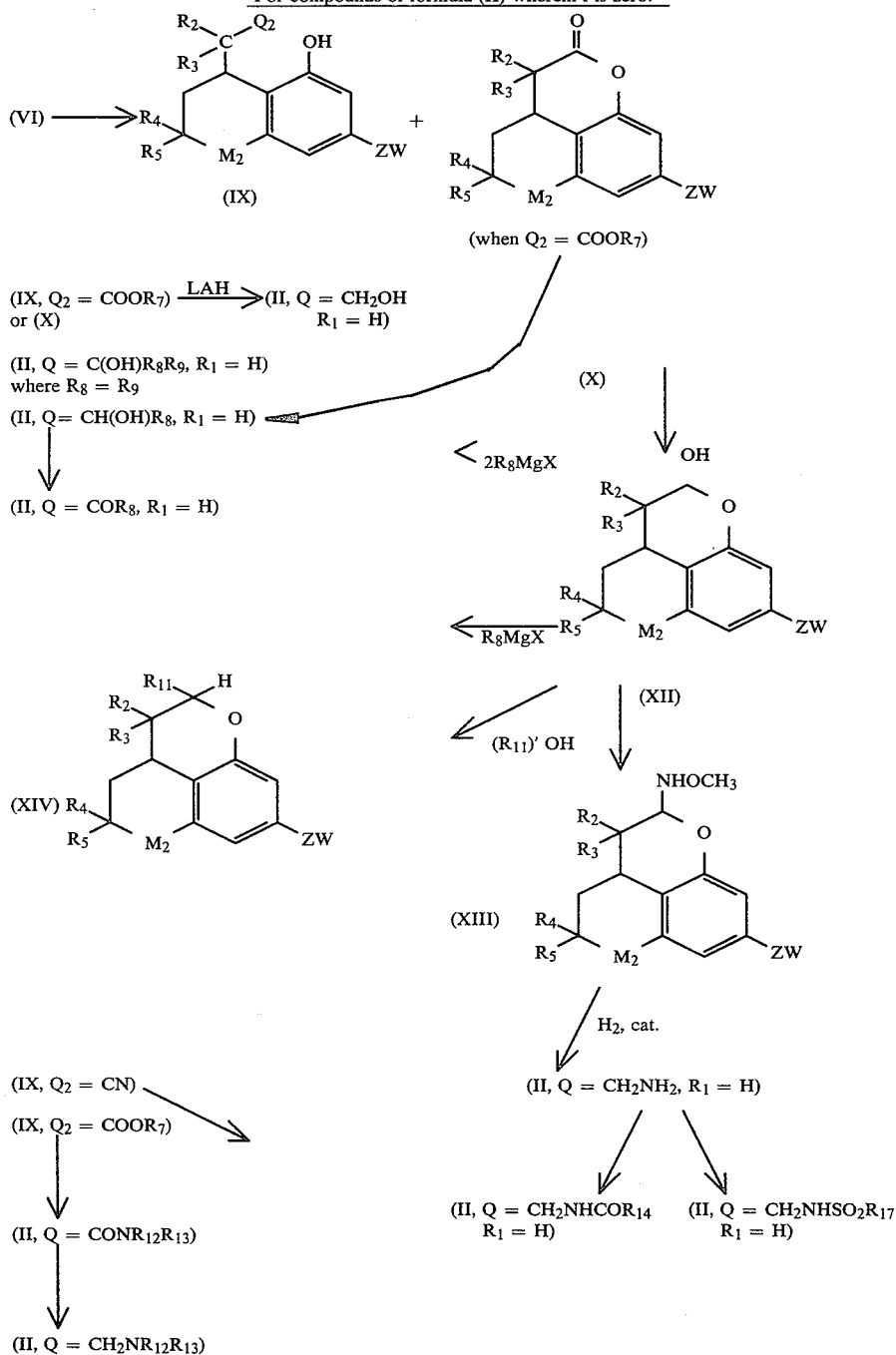

In said starting materials (IVA), $Y_1$ is an hydroxy protecting group, such as e.g., benzyl or methyl; $R_4$, $R_5$, $M_2$, Z and W are as previously defined. In the first step of the reaction sequence the compound of formula (IVA) is reacted with an alpha-haloester or alpha-halonitrile in the presence of zinc metal, the well known Reformatsky reaction, to provide the corresponding intermediates of formula (VI). Alternatively, this step is carried out by a modification of the Reformatsky reaction employing a lithio acetic acid ester or lithio acetonitrile reagent of formula $LiC(R_2R_3)Q_2$ where $Q_2$ is $COOR_7$ or CN and $R_2$, $R_3$ and $R_7$ are as previously defined. A recent extensive review of the Reformatsky reaction is that of Rathke in Organic Reactions, 22, 423–460 (1975).

When the above mentioned alpha-haloesters or alpha-halonitriles are employed, the preferred reagents are the bromo compounds of formula $BrC(R_2R_3)Q_2$, wherein $R_2$ and $R_3$ are each hydrogen, methyl or ethyl and $Q_2$ is CN or $COOR_7$ and $R_7$ is as previously defined. The reagent, $BrC(R_2R_3)Q_2$ is contacted, for example, with at least an equimolar amount of zinc metal in the presence of a reaction inert organic solvent to provide an organometallic intermediate, $BrZnC(R_2R_3)Q_2$, which is then reacted with the ketone of formula (IVA) to provide the desired intermediate of formula (VI) after hydrolysis of the reaction mixture with, e.g., ammonium hydroxide or acetic acid. Alternatively, the zinc metal, reagent, $BrC(R_2R_3)Q_2$ and starting ketone (IVA) may be contacted simultaneously in the presence of reaction inert organic solvent to provide the desired intermediate (VI).

Preferred temperatures for carrying out the above reaction between $BrC(R_2R_3)Q_2$ and starting material (IVA) are in the range of from about 0° C. up to the reflux temperature of said solvent. Examples of reaction inert solvents which may be employed are benzene, toluene, ethyl ether, tetrahydrofuran, dimethoxymethane, 1,2-dimethoxyethane, diethyleneglycol dimethylether, trimethylborate and mixtures thereof. Preferred such solvents are benzene, tetrahydrofuran, dimethoxymethane and 1,2-dimethoxyethane. The desired intermediate of formula (VI) is isolated by standard methods known in the art and exemplified herein. The crude intermediates are purified, if desired, by standard methods, e.g., recrystallization or column chromatography.

When lithio reagents $LiC(R_2R_3)Q_2$ are employed to prepare the intermediates of formula (VI), they may be prepared by any of several methods known in the art; see, for example, Fieser, "Reagents for Organic Chemistry", Wiley-Interscience, New York, Vol. 3, 1972. However, a preferred method, exemplified herein, employs a lithium dialkylamide and an acetic acid ester or nitrile of formula $CH(R_2R_3)Q_2$ in reaction inert solvent. A particularly preferred lithium dialkylamide is lithium dicyclohexylamide. The latter compound is prepared, for example, from equimolar amounts of n-butyl lithium and dicyclohexylamine in reaction inert solvent. In a typical reaction the two reagents are contacted under anhydrous conditions and in the presence of an inert atmosphere, e.g., nitrogen, at $-80°$ to $-70°$ C. in reaction inert solvent and to the resulting slurry is added an equimolar amount of reagent of formula $CH(R_2R_3)Q_2$ at the same temperature. The resulting lithio reagent, $LiC(R_2R_3)Q_2$ is then reacted immediately with the starting ketone (IVA) in reaction inert solvent also at a temperature of from about $-80°$ to $-70°$ C. The reaction is ordinarily completed in from about one to ten hours, after which the reaction mixture is quenched by addition of an equivalent amount of weak acid, e.g., acetic acid, to decompose the lithium salt of the desired product. The product is then isolated by standard methods and purified, if desired, as described above. Examples of the reaction inert solvents which may be employed and preferred such solvents are those mentioned above for the reaction employing haloester or halonitrile reagents.

The 4-hydroxy-4-$(R_2R_3CQ_2)$-substituted compounds of formula (VI), obtained as described above, are then subjected to hydrogenolysis and removal of hydroxy protecting group $Y_1$ to provide compounds of formula (IX), (X) or a mixture thereof. The hydrogenolysis of compounds of formula (VI) where $Q_2$ is $COOR_7$ is ordinarily carried out by means of hydrogen in the presence of a noble metal catalyst. Examples of noble metals which may be employed are nickel, palladium, platinum and rhodium. The catalyst is ordinarily employed in catalytic amounts, e.g., from about 0.01 to 10 weight-percent and preferably from about 0.1 to 2.5 weight-percent, based on the compound of formula (VI). It is often convenient to suspend the catalyst on an inert support, a particularly preferred catalyst is palladium suspended on an inert support such as carbon.

One convenient method of carrying out this transformation is to stir or shake a solution of the compound of formula (VI) under an atmosphere of hydrogen in the presence of one of the above noble metal catalysts. Suitable solvents for this hydrogenolysis reaction are those which substantially dissolve the starting compound of the formula (VI) but which do not themselves suffer hydrogenation or hydrogenolysis. Examples of such solvents include the lower alkanols such as methanol, ethanol and isopropanol; ethers such as diethyl ether, tetrahydrofuran, dioxan and 1,2-dimethoxyethane; low molecular weight esters such as ethyl acetate and butyl acetate; tertiary amides such as N,N-dimethylformamide, N,N-dimethylacetamide and N-methylpyrrolidone; and mixtures thereof. Introduction of the hydrogen gas into the reaction medium is usually accomplished by carrying out the reaction in a sealed vessel, containing the compound of formula (VI), the solvent, the catalyst and the hydrogen. The pressure inside the reaction vessel can vary from about 1 to about 100 kg/cm². The preferred pressure range, when the atmosphere inside the reaction vessel is substantially pure hydrogen, is from about 2 to about 5 kg/cm². The hydrogenolysis is generally run at a temperature of from about 0° to about 60° C., and preferably from about 25° to about 50° C. Utilizing the preferred temperature and pressure values, hydrogenolysis generally takes place in a few hours, e.g., from about 2 hours to about 24 hours.

The product is then isolated by standard methods known in the art, e.g., filtration to remove the catalyst and evaporation of solvent or partitioning between water and a water immiscible solvent and evaporation of the dried extract.

When the starting compound employed in the hydrogenolysis is of formula (VI) wherein $Y_1$ is hydrogen or benzyl and $Q_2$ is $COOR_7$, the product obtained is ordinarily a mixture of the corresponding carboxylic acid or ester of formula (IX) and the lactone of formula (X) formed by elimination of the elements of $R_7OH$ from (IX). The mixture thus obtained may be used as is or may be separated by well known methods, e.g., by crystallization and/or chromatography on silica gel.

Of course, when the starting compound for the hydrogenolysis is of formula (VI) wherein $Y_1$ is alkyl, benzoyl or alkanoyl as defined above and $Q_2$ is $COOR_7$, the only product obtained is the corresponding $Y_1$-substituted derivative of the compound of formula (IX). Removal of the hydroxy protecting group $Y_1$, e.g., by hydrolysis (when $Y_1$ is benzoyl or alkanoyl as defined above) or by methods known in the art for cleaving ethers (when $Y_1$ is alkyl as defined above), e.g., by means of HBr/acetic acid, then affords the desired compound of (IX) or its mixture with lactone (X).

In a preferred method for conversion of compounds of formula (VI) where $Q_2$ is CN to the corresponding compound of formula (IX), the compound (VI) is first dehydrated to form a 4-cyanomethylene derivative and this is hydrogenated by means of magnesium in methanol to form the hydroxy-protected derivative of (IX) from which the protecting group is then removed. This sequence is outlined below for the case wherein $Q_2=CN$, $R_2$ and $R_3=H$, $R_4$ and $R_5=CH_3$, $Y^1=CH_2C_6H_5$ and $M_2=O$.

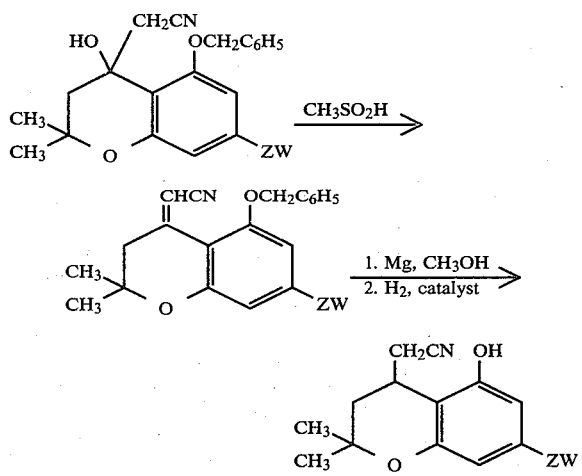

The dehydration step is carried out in a reaction inert solvent, e.g., benzene, toluene or ethyl ether. To the solution of the starting 4-hydroxy compound is added an absorbent for water, e.g., molecular sieves, and a catalytic amount of methanesulfonic acid and the mixture stirred at room temperature, typically overnight. The dehydrated product is isolated by standard methods and reduced in methanol in the presence of magnesium metal at $-10°$ to $30°$ C., typically this reaction is complete in from about 4 to 48 hours. The benzyl protecting group is then removed by catalytic hydrogenation as described above. Of course for compounds of formula (VI, $Q_2=CN$) wherein both of $R_2$ and $R_3$ are methyl or ethyl, the same method employed for conversion of compounds of formula (VI) where $Q_2=CO_2R_7$ to compounds of formula (IX), described above, is preferred.

The products of formula (IX, $Q_2=CO_2R_7$) and (X), as well as mixtures thereof, are useful intermediates for production of the corresponding hydroxy compounds of formula (II, $Q=CH_2OH$, $f=0$) by means of known reducing agents, e.g., hydrides such as lithium aluminum hydride or lithium borohydride, aluminum borohydride, borane, aluminum hydride and lithium triethylborohydride and by catalytic hydrogenation over noble metal catalysts. Preferred reducing agents are the above hydrides and especially preferred is lithium aluminum hydride for reasons of economy and efficiency. The reduction is carried out under anhydrous conditions and in the presence of a suitable reaction inert solvent e.g., ethyl ether, tetrahydrofuran, 1,2-dimethoxyethane and diethyleneglycol dimethylether. Typically, the compound of formula (IX, $Q_2=CO_2R_7$), the lactone (X) or mixture thereof dissolved in one of the above reaction inert solvents is added to a solution of an approximately equimolar amount of hydride, e.g., lithium aluminum hydride, in the same solvent and the mixture maintained at a temperature of from about $-50°$ to $50°$ C., and preferably from about $0°$ to $30°$ C. Under these conditions the reduction is substantially complete in from about 2 to 24 hours, after which the excess reducing agent is quenched, e.g., by cautious addition of wet solvent or ethyl acetate and the product isolated by known techniques, e.g., washing and reaction mixture with water and evaporation of the dried organic phase. Purification, if desired, is carried out, e.g., by recrystallization or column chromatography.

The lactones (X) are also useful as intermediates for production of the corresponding lactols of formula (XII) by means of reagents and conditions known to selectively reduce the lactone carbonyl group to a carbinol without ring cleavage. A preferred such reagent is diisobutylaluminum hydride (DIBALH). In a typical reaction, the lactone (X) is dissolved in a reaction inert solvent, such as an aromatic hydrocarbon solvent, preferably toluene, the solution is cooled to a temperature of from about $-90°$ to $-50°$ C., preferably about $-80°$ to $-60°$ C., under anhydrous conditions and in the presence of an inert atmosphere such as nitrogen or argon. An equimolar amount of DIBALH is then added slowly while maintaining the mixture within the preferred temperature range. After the addition is complete, the reaction is allowed to proceed under these conditions until substantially complete, which ordinarily requires from about one to ten hours. The reaction mixture is then quenched, for example, by addition of methanol, then allowed to warm to room temperature. The desired lactol (XII) is then isolated, e.g., by washing with water, drying and evaporation of solvent.

The esters of formula (IX) where $Q_2$ is $COOR_7$ and $R_7$ is alkyl having from one to four carbon atoms or benzyl and the lactones (X) also serve as starting materials for preparation of the tertiary alcohol compounds of the invention of formula (II, $f=0$) shown in Flow Chart A and below

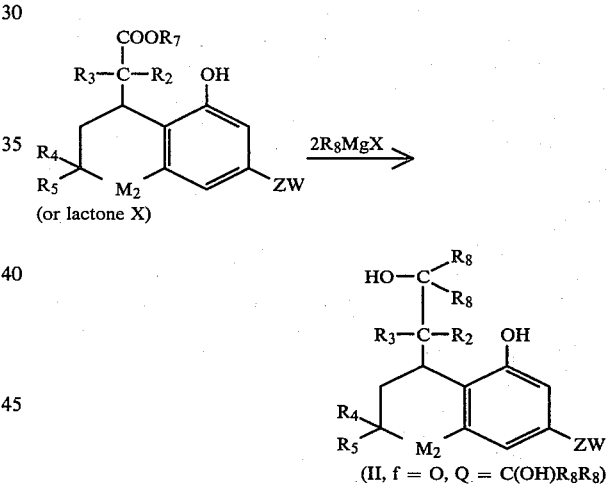

The ester, lactone or a mixture thereof dissolved in a reaction inert solvent, e.g., ethyl ether, isopropyl ether, tetrahydrofuran or 1,2-dimethoxyethane, is contacted under anhydrous conditions with at least two moles of the appropriate Grignard reagent $R_8MgX$, where $R_8$ is $C_1$-$C_4$alkyl, phenyl or benzyl and X is Cl, Br or I, at a temperature of from about $0°$ C. up to the reflux temperature of the solvent, preferably at room temperature. The reaction is ordinarily complete in from about 2-24 hours. The excess Grignard reagent is then decomposed and the product isolated by standard methods well known in the art. For example, water is added, the layers separated, the aqueous phase extracted with a water immiscible solvent, e.g., ethyl ether, and the product isolated from the combined extracts by evaporation of solvent. Purification, if desired, is accomplished by, e.g., recrystallization or column chromatography. Preferred reaction inert solvents for this reaction are ethyl ether and tetrahydrofuran.

Grignard reaction of the above described lactols of formula (XII) employing equimolar amounts of Grignard reagent and lactol under the above described conditions, similarly provides secondary alcohols of formula (II, f=O, Q=CH(OH)R$_8$, R$_1$=H).

Oxidation of the secondary alcohols or corresponding primary alcohols of formula (II, f=O) provided above, employing an oxidizing agent known to oxidize primary and secondary alcohols to aldehydes and ketones, respectively, provides the corresponding compounds of formula (II, f=O, Q=COR$_8$) where R$_8$ is hydrogen, C$_1$-C$_4$alkyl, phenyl or benzyl. Oxidizing agents which can be employed for this oxidation are well known in the art, see, e.g., Sandler and Karo, "Organic Functional Group Preparations", Academic Press, New York, 1968, pp. 147-173. Preferred oxidizing agents, however, are chromic acid, chromic anhydride, potassium dichromate, manganese dioxide and lead tetraacetate and particularly preferred is chromic anhydride in pyridine. While the oxidation with the preferred agents above may be carried out over a wide range of temperature, e.g., from about 0° to 100° C., a preferred temperature is from about 10° to 50° C. The alcohol and a molar excess of chromic anhydride, e.g., a 100% molar excess, are contacted in aqueous pyridine. The oxidation is ordinarily complete at a temperature in the preferred range, in from about one to eight hours. After which the product is isolated by pouring the mixture into water, extraction with a water immiscible solvent, e.g., ethyl ether, methylene chloride or chloroform, and evaporation of solvent.

Reaction of the lactols of formula (XII) with alcohols of formula (R$_{11}$)'OH, where (R$_{11}$)' is alkyl having from one to four carbon atoms, under acidic conditions known to convert lactols (hemiacetals) to acetals provides the invention compounds of formula (XIV) as shown in Flow Chart A, above. In a typical reaction, the lactol is dissolved in a large excess, e.g., a solvent amount of the alcohol of formula (R$_{11}$)'OH, dry hydrogen chloride or concentrated sulfuric acid added in from a catalytic amount up to an amount equimolar to the lactol and the mixture maintained at a temperature of from about 0° C. up to the boiling point of the alcohol, preferably room temperature, until acetal formation is complete. The time required for completion is ordinarily about 4-48 hours. After which the acetal is isolated by known methods, e.g., by pouring into water, extracting with ether, drying the extracts and evaporation of solvent. The product thus provided is ordinarily a mixture of the alpha- and beta-anomeric acetals which can be separated, e.g., by chromatography on silica gel.

The lactols of formula (XII) are also useful intermediates for preparation of amines of formula (II, f=O, Q=CH$_2$NH$_2$) via an alkoxyamino intermediate, e.g., the methoxyamino compounds for formula (XIII). The lactol is first reacted with an alkoxyamine, preferably methoxyamine. Equimolar amounts of the reactants are contacted in the presence of a suitable solvent such as, for example, methanol, ethanol, tetrahydrofuran, dimethylformamide, pyridine or mixtures thereof. Preferred solvents are ethanol, pyridine or their mixtures. The reaction can be carried out satisfactorily at a temperature in the range of from about −20° to 50° C.; however, a temperature of from about −10° to 25° C. is preferred. Under preferred conditions the reaction is ordinarily complete in from about one to six hours. The product of formula (XIII) is then isolated by standard means, e.g., by evaporation of solvent and partitioning the residue between water and a water immiscible solvent, e.g., ethyl ether.

Catalytic hydrogenolysis of the alkoxyamino intermediate affords the corresponding bicyclic compound of formula (II) where Q is CH$_2$NH$_2$, f=O and R$_1$ is H. The hydrogenolysis is carried out in the presence of hydrogen and a noble metal catalyst under conditions described above for hydrogenolysis of compounds of formula (VI). However, a particularly preferred method employs a nickel/aluminum alloy in the presence of aqueous alkali, e.g., sodium hydroxide or potassium hydroxide. The reaction of the aluminum with alkali produces the requisite hydrogen and continually provides fresh catalyst (nickel) for the reaction at the same time. In a particularly preferred embodiment of this reaction approximately equal weights of the methoxyamino compound (XIII) and Raney alloy (1:1 by weight nickel/aluminum) are contacted in the presence of dilute aqueous alkali, e.g., sodium hydroxide and in the presence of a suitable solvent, e.g., methanol or ethanol. The mixture is heated at a temperature of from about 40° C. up to the reflux temperature of the mixture. The reaction is substantially complete in from about 1 to 10 hours, after which the product (II, Q=CH$_2$NH$_2$, f=O, R$_1$=H) is isolated by known methods and purified, e.g., by column chromatography.

The compounds of formula (II, Q=CH$_2$NH$_2$, f=O, R$_1$=H) can also be prepared by reduction of the compounds of formula (IX, Q$_2$=CN) employing hydrogen in the presence of a noble metal catalyst or by means of hydride reducing agents such as e.g., borane, aluminum hydride, lithium aluminum hydride or lithium triethylborohydride. A particularly preferred method employs lithium aluminum hydride in the presence of a reaction inert solvent, e.g., ethyl ester or tetrahydrofuran under conditions set forth above for reduction of the corresponding esters (IX, Q$_2$=COOR$_7$) with the same reagent to form compounds (II, Q=CH$_2$OH, R$_1$=H).

The amides of formula (II, Q=CONR$_{12}$R$_{13}$) are prepared from the esters or acids of formula (IX, Q$_2$=COOR$_7$) by reaction with ammonia or the appropriate amine of formula R$_{12}$R$_{13}$NH employing standard methods known in the art. Typically, approximately equimolar amounts of the ester of formula (IX, Q$_2$=COOR$_7$) and the above amine or ammonia are contacted in the presence of solvent and at a temperature in the range of from about 0° to 100° C. Examples of solvents which may be successfully employed in this reaction are the lower alkanols such as methanol, ethanol, isopropanol and n-butanol; ethers such as diethylether, tetrahydrofuran, 1,2-dimethoxyethane and diethyleneglycol dimethylether; hydrocarbons such as hexane, benzene and toluene and mixtures thereof. Preferred solvents are methanol, ethanol, isopropanol, tetrahydrofuran, toluene and their mixtures.

When acids of formula (IX, Q$_2$=COOH) are employed to provide amides of formula (II, Q=CONR$_{12}$R$_{13}$), it is preferable to convert the acid to an activated derivative such as the acid halide or a mixed anhydride prior to reaction with the amine or ammonia of formula R$_{12}$R$_{13}$NH. Typically, the acid is first reacted with an equimolar amount of thionyl chloride to form the corresponding acid chloride by methods well known in the art, and the latter compound reacted with at least an equimolar amount of free base of formula R$_{12}$R$_{13}$NH, but preferably a molar excess of base, e.g., 2-3 moles, in the presence of a reaction inert organic solvent. The resulting amide is then isolated by filtration to remove precipitated amine hydrochloride salt and the product isolated by washing and evaporation of the filtrate. Preferred reaction inert solvents for this procedure are ethyl ether, tetrahydrofuran, chloroform or methylene chloride. It is also preferred that this reaction be carried out with 1-acyloxy compounds of formula (IX, $Q_2$=COOH) in order to prevent unwanted side reaction of the acid halide with the phenolic hydroxy group ($R_1$=H). A preferred acyloxy is acetoxy. The resulting acyloxyamide, e.g., (II, Q=CONR$_{12}$R$_{13}$, $R_1$=CH$_3$CO) may then be converted to the corresponding hydroxy compound ($R_1$=H) by contacting the product thus obtained with dilute aqueous alkali, e.g., sodium hydroxide, potassium hydroxide or sodium carbonate.

The amides of formula (II, Q=CONR$_{12}$R$_{13}$) can be reduced by either catalytic hydrogenation or metal hydrides to provide the corresponding amine derivatives (II, Q=CH$_2$NR$_{12}$R$_{13}$) as described above for reduction of nitriles (IX, $Q_2$=CN) to provide the primary amines, (II, Q=CH$_2$NH$_2$).

Reaction of the latter primary amine compounds with, e.g., an acid halide of formula R$_{14}$COCl, R$_{14}$COBr or a mixed anhydride of formula R$_{14}$COOCOalkyl where alkyl is $C_1$-$C_4$, employing the same methods and conditions described above for preparation of amides of formula (II, Q=CONR$_{12}$R$_{13}$), provides the desired amides of formula (II, Q=CH$_2$NHCOR$_{14}$). Similarly, use of a sulfonyl halide of formula R$_{17}$SO$_2$Cl or R$_{17}$SO$_2$Br affords the corresponding sulfonamide (II, Q=CH$_2$NHSO$_2$R$_{17}$) where R$_{17}$ is as previously defined.

Flow Chart B, below, illustrates the methods which can be employed to provide the invention compounds of formula (II) wherein f is 1.

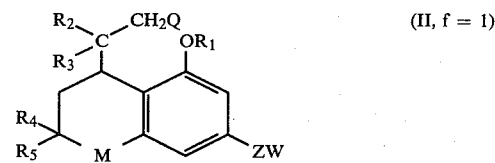

A primary alcohol of formula (II) wherein f=O, Q=CH$_2$OH, $R_1$=COCH$_3$ and $R_2$, $R_3$, $R_4$, $R_5$, Z and W are as previously defined is first converted to the corresponding alkylsulfonyl or arylsulfonyl ester wherein alkyl is, e.g., of from one to four carbon atoms and aryl is, e.g., phenyl or tolyl. An especially preferred sulfonyl ester is methylsulfonyl for reasons for economy and efficiency. In a typical such reaction the primary alcohol of formula (II), as defined above, and an equimolar amount of methanesulfonyl chloride are contacted in the presence of a solvent amount of pyridine or triethylamine which also acts as an acid acceptor. The resulting mixture is maintained at a temperature of from about −10° to 40° C., preferably from about 0° to 30° C., at which temperature the reaction is complete in from about 15 minutes to four hours. The methanesulfonyl ester is then isolated by standard techniques, e.g., by evaporation of volatiles and partitioning of the residue between water and a water immiscible solvent, washing and evaporation of solvent.

FLOW CHART B

For Compounds of formula (II) wherein f is 1:

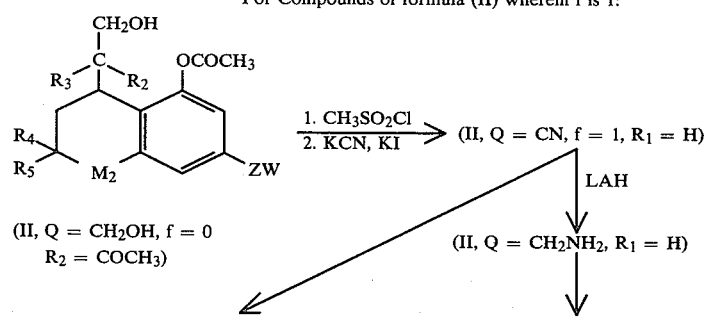

FLOW CHART B

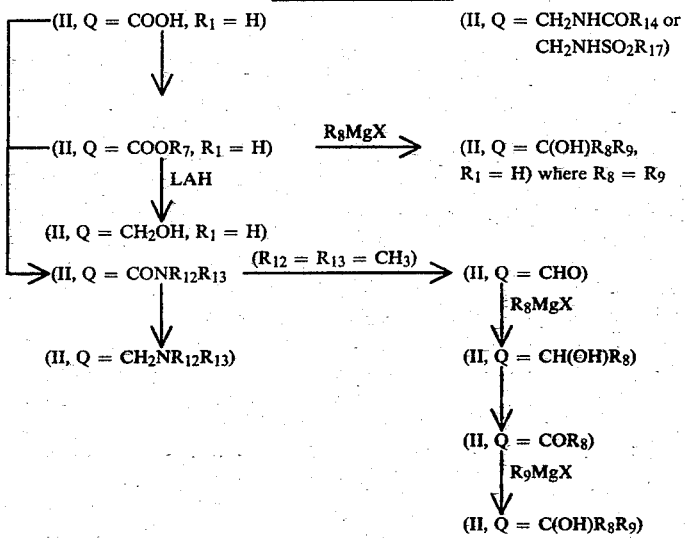

The mesylate ester thus provided is further reacted with a molar excess, e.g., a 2-20 molar excess, of an alkali metal cyanide, preferably potassium cyanide and preferably in the presence of a catalytic amount of potassium iodide to afford the desired compound of formula (II, f=1, Q=CN, $R_1$=H). This reaction is ordinarily carried out in the presence of a reaction inert polar solvent, preferably dimethylformamide, dimethylsulfoxide, diethyleneglycol dimethyl ether, or their mixtures with water; and at a temperature of from about 50° to 150° C., preferably 75° to 105° C. Under the above mentioned preferred conditions the formation of the desired nitrile is complete in from about one to six hours. The product is isolated by methods well known in the art, e.g., by evaporation of solvent, partitioning the residue between water and water immiscible solvent, e.g., chloroform or methylene chloride and evaporation of the solvent. The residue is purified, if desired, e.g., by chromatography. The nitrile, thus obtained, serves as precursor of the remaining compounds of formula (II, f=1) as shown in Flow Chart B.

Hydrolysis of the nitrile, employing methods and conditions well knoown in the art for conversion of nitriles to carboxylic acids, affords the acids of formula (II, f=1, Q=COOH). Typically, the nitrile in aqueous alcoholic alkali, e.g., sodium hydroxide is heated at reflux for about 4-24 hours and the product isolated by acidification of the mixture, extraction into a water immiscible solvent, e.g., ethyl ether or chloroform, and evaporation of solvent.

Esterification of the carboxylic acids obtained above with alcohols of the formula $R_7OH$ provides the corresponding esters of formula (II, f=1, Q=COOR$_7$) where $R_7$ is alkyl having from one to four carbon atoms. The esterification is typically carried out by contacting the carboxylic acid (II, f=1, Q=COOH) with a molar excess of alcohol, $R_7OH$, in the presence of a catalytic amount of a strong acid, e.g., hydrogen chloride or sulfuric acid, at a temperature of from about 25° C. up to the reflux temperature of the mixture, preferably 50° to 110° C., for about 4 to 24 hours. The ester is then isolated by neutralization of the mixture with, e.g., sodium hydroxide, filtration and evaporation of the filtrate.

Reduction of the compounds of formula (II, f=1, Q=COOR$_7$) by means of hydrogen and a noble metal catalyst or employing metal hydride reducing agents, e.g., lithium aluminum hydride, as described above for the corresponding compounds wherein f=O, provides the primary alcohols of formula (II, f=1, Q=CH$_2$OH).

The amides of formula (II, f=1, Q=CONR$_{12}$R$_{13}$) are obtained by reaction of the corresponding acids and esters wherein Q=COOR$_7$ by the methods previously described for the corresponding compounds wherein f=O. Similarly, the compounds of formula (II, f=1, Q=CH$_2$NR$_{12}$R$_{13}$) are obtained by reduction of the appropriate amide as described above for their counterparts wherein f=O.

The remaining compounds of formula (II, f=1) wherein Q is CH$_2$NH$_2$, CH$_2$NHCOR$_{14}$, CH$_2$NHSO$_2$R$_{17}$ and C(OH)R$_8$R$_9$ are also obtained by corresponding procedures previously defined for their counterparts wherein f=O.

The invention compounds of formula (II, Q=CHO) wherein f=O or 1 are preferably provided by reaction of the corresponding N,N-dialkylamide of formula (II, Q=CONR$_{12}$R$_{13}$) with disiamylborane [bis(1,2-dimethylpropyl)borane]. In a typical reaction the tertiary amide, e.g., N,N-dimethylamide, of formula (II) and a molar excess, e.g., a 100% molar excess, of disiamylborane are contacted in a reaction inert solvent, e.g., tetrahydrofuran at a temperature of from about 0° to 50° C., preferably room temperature until the formation of aldehyde is complete, typically from about 2 to 20 hours. The excess reducing reagent is then decomposed by cautious addition of water, the solvent evaporated, the residue isolated by partitioning between water and water immiscible solvent and the solvent evaporated.

Reaction of the aldehydes (II, Q=CHO) wherein f is O or 1 with an equimolar amount of Grignard reagent, R$_8$MgX, employing methods and conditions previously described for reaction of esters of formula (II, f=O, Q=COOR$_7$) or the corresponding lactones of formula (X), affords secondary alcohols of formula [II, Q=CH(OH)R$_8$] wherein f=O or 1.

Oxidation of the secondary alcohols of formula (II, Q=CH(OH)R$_8$) wherein f is O or 1 employing oxidizing agents and conditions known in the art to convert secondary alcohols to the corresponding ketones, provides the corresponding invention compounds of formula (II, Q=COR$_8$). Examples of oxidizing agents which can be employed in production of these ketones are potassium permanganate, potassium dichromate chromium trioxide and chromium trioxide in the presence of pyridine. In carrying out the oxidation to the starting secondary alcohol in a reaction inert solvent, e.g., dichloromethane, chloroform, benzene, pyridine, water or mixtures thereof, is added at least an equimolar amount, preferably a molar excess, e.g., 100–500% molar excess, of the oxidizing agent and the oxidation allowed to proceed to substantial completion. While this oxidation can be successfully carried out over a wide range of temperatures such as from 0° to 100° C., a preferred temperature when the preferred oxidizing agent is employed is in the range of from 10° to 30° C. Under these conditions the reaction is complete in from about one to six hours, typically two to four hours. A preferred solvent for the oxidation is aqueous pyridine when the oxidizing agent is chromium trioxide in the presence of pyridine. The product is isolated, for example, by pouring the reaction mixture into water, adjusting the mixture to an acidic pH and extraction with a water immiscible solvent, e.g., chloroform, methylene chloride or ethyl ether. Drying the extracts and evaporation of solvent affords the desired ketone.

Reaction of the ketones of formula (II, Q=COR$_8$) wherein f is zero or 1 with an equimolar amount of a Grignard reagent of formula R$_9$MgX, wherein R$_9$ is as previously defined and is the same or different than R$_8$, employing methods and conditions described above for the reaction of esters of formula (II, f=O, Q=COOR$_7$) or the lactones of formula (X), affords tertiary alcohols of the invention of formula (II, Q=C(OH)R$_8$R$_9$) wherein f is zero or 1.

The 4-hydroxy-4-acetamido compounds of formula (XVIII) are derived from the corresponding esters or nitriles of formula (VI) by methods analogous to those described above for preparing the corresponding amides of formula (II).

The 4-amido and 4-imido compounds of formula (XIX) are obtained, for example, by the reaction sequence below.

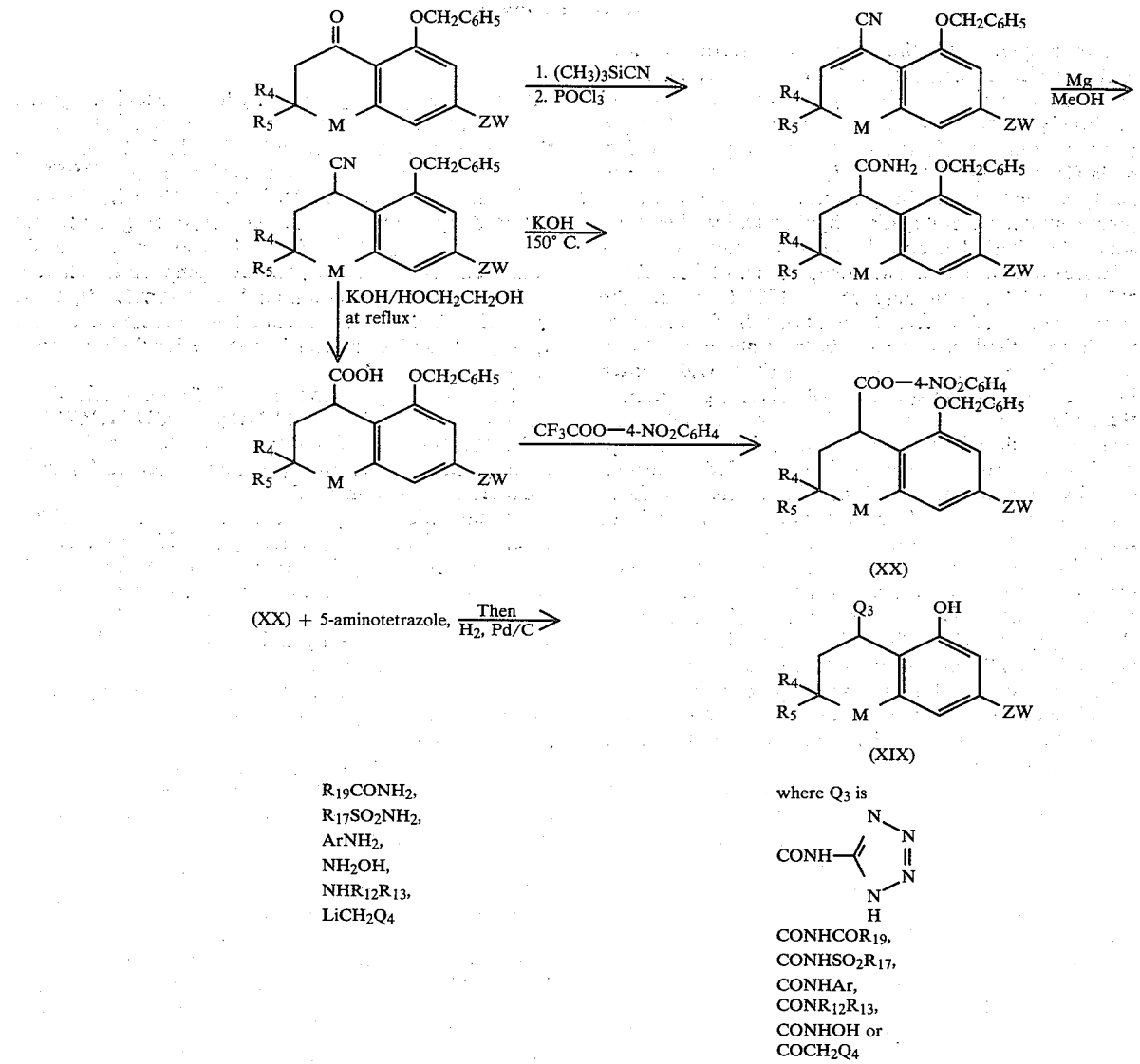

Hydrogenolysis of the benzyl group with palladium-on-carbon catalyst can likewise be carried out on any of the above intermediates, except the alpha,beta-unsaturated nitrile, to provide the corresponding 5-hydroxy compounds.

The spiro imides of formula (XIX) where $Q_3$ is

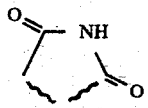

are provided by reacting the corresponding ester, (XIX, $Q_3$ is $COOR_7$) with e.g. ethyl lithioacetate at $-70°$ C., hydrolysis of the resulting diester, cyclization to form the spiro anhydride and heating this with ammonia or urea at $100°-250°$ C. to form the desired imide.

Flow Chart C outlines, for example, methods which can be employed to provide the invention compounds of formula (III) wherein f is 1 or 2. The requisite starting 3-hydroxymethylene-2,2-$R_4R_5$-4-keto-5-hydroxy-7-ZW-substituted compounds of formula (VA) where $M_1$ is e.g., O, $CH_2$, NCHO or $NCH_3$ and $R_4$, $R_5$, Z and W are as defined above, as well as its derivatives wherein the phenolic hydroxy group is protected, are provided in U.S. Pat. No. 4,143,139 ($M_1=O$), U.S. Pat. No. 4,188,495 ($M_1=CH_2$), U.S. Pat. No. 4,228,169 ($M_1=NCHO$ or $NCH_3$) and U.S. Pat. No. 4,260,764 ($M_1=NCHO$ or $NCH_3$), which, as previously stated, are incorporated herein by reference.

FLOW CHART C
(For compounds of formula (III), f = 1 and f = 2).

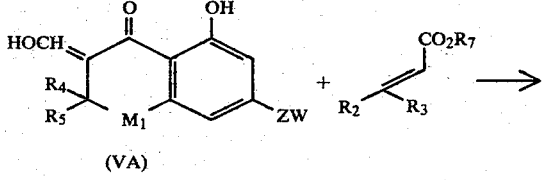

(VA)
$M_1 = O, CH_2, NCHO, NCH_3$

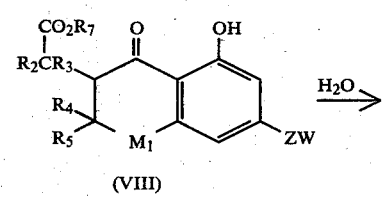

(VIII)

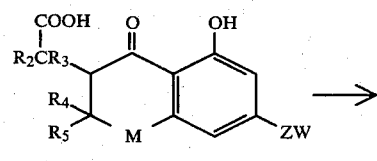

(XV)
(M = $M_1$ or NH)

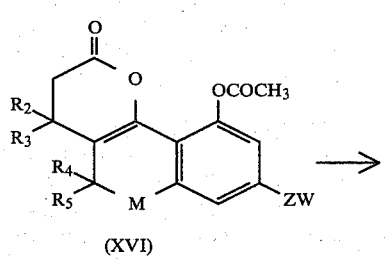

(XVI)

-continued
FLOW CHART C
(For compounds of formula (III), f = 1 and f = 2).

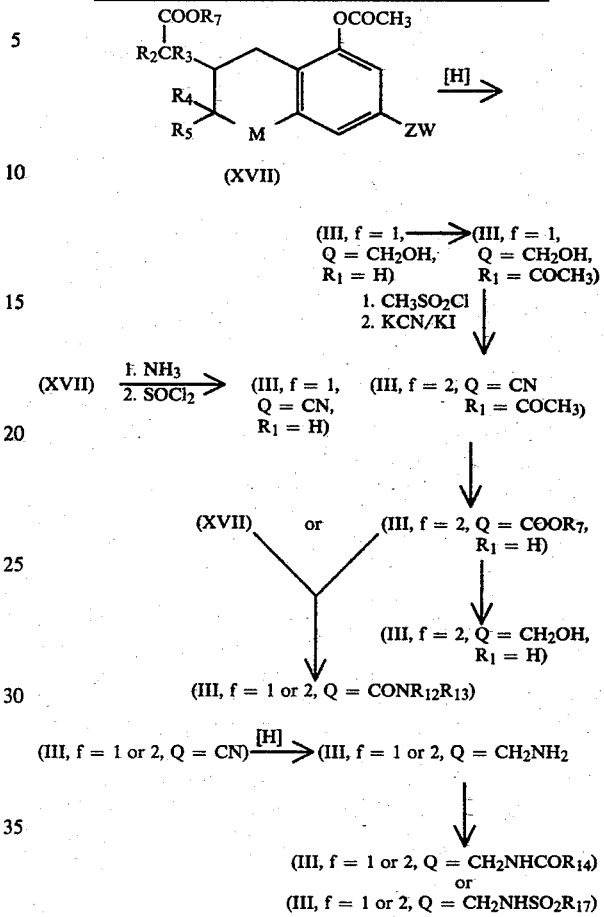

The starting compound of formula (VA) is initially reacted with at least an equimolar amount of acrylate ester of the formula $R_2R_3C=CHCO_2R_7$, where $R_2$ and $R_3$ are as previously defined and $R_7$ is alkyl having from one to four carbon atoms or benzyl, to provide intermediate ketoesters of formula (VIII). The reaction is carried out in the presence of a base, for example, an alkali metal hydroxide or alkoxide such as sodium hydroxide, potassium hydroxide, sodium methoxide or potassium ethoxide; or a tertiary organic base such as triethylamine, to effect Michael addition and decarboxylation. The reaction can be carried out in the presence or absence of solvent and at a temperature of from about 0° to 50° C. In a typical reaction, the starting material of formula (VA) and a molar excess, e.g., a 2-6 molar excess, of the above acrylate ester are contacted in the presence of about 1 to 10 moles of triethylamine as base. Under these conditions the reaction is complete in a few days and the product is then isolated and purified by standard techniques.

The ketoester intermediate (VIII) is then hydrolyzed to the corresponding ketoacid (XV). The hydrolysis is conveniently effected by, e.g., an alkali metal hydroxide such as sodium hydroxide at a temperature of from about 0° to 60° C., typically at room temperature. When the starting ester (VIII) is one wherein $M_1$ is NCHO, the hydrolyses can be carried out to provide either the corresponding acid (XV) wherein M is NCHO, or the free base where M is NH, by suitable selection of hydrolysis conditions. For example, hydrolysis at a low temperature within the above range, e.g., at about 15° C., affords the compound (XV) where M is NCHO. Use of higher temperatures favors hydrolysis of the N-formyl group as well as the ester group to afford the free base of formula (XV).

The ketoacid (XV) is then cyclized to provide the enolic lactone (XVI). This step is carried out under dehydrating conditions employing, for example, sodium acetate and acetic anhydride. In a typical such reaction, the ketoacid (XV) and an equimolar amount of sodium acetate are contacted with 2-200 fold molar excess of acetic anhydride and the mixture heated at about 100° C. in the presence of an inert gas such as argon or nitrogen for from 8 hours up to a few days, after which the reaction mixture is concentrated in vacuo and the residue purified by column chromatography.

Catalytic hydrogenation of the enol-lactones (XVI) provided above, under conditions which affects hydrogenolysis of the benzylic oxygen in the 4-position, is then carried out employing the same catalysts and conditions previously described for hydrogenolysis of compounds of formula (VI) to yield the carboxylic acids of formula (XVII) where $R_7$ is hydrogen. The corresponding esters, where $R_7$ is $C_1$–$C_4$alkyl or benzyl, are then prepared, if desired, by standard esterification methods.

The compounds of formula (XVII) are active CNS agents of the invention and are also useful as intermediates for other invention compounds of formula (III) as is shown in Flow Chart C. For example, they are reduced, e.g., by metal hydrides, to provide the compounds of formula (III, f=1, Q=$CH_2OH$, $R_1$=H) employing the same reagents and conditions described above for reduction of compounds of formulae (IX) or (X) to provide the compounds of formula (II, f=1, Q=$CH_2OH$, $R_1$=H).

Contacting the esters of formula (XVII) or an activated derivative of the acids of (XVII) wherein $R_7$ is hydrogen with an equimolar amount of anhydrous ammonia, affords the corresponding primary amide of formula (III, f=1, Q=$CONH_2$, $R_1$=H). Further reaction of this amide with thionyl chloride at the reflux temperature affords the corresponding nitrile of formula (III, f=1, Q=CN, $R_1$=H).

In a typical reaction to prepare the above primary amides, the ester of formula (XVII) in a suitable solvent, e.g., methanol, ethanol, isopropanol or acetone, is treated with a molar excess of anhydrous ammonia at or about room temperature. The mixture is then heated at a temperature up to the reflux temperature of the solvent while continuing to introduce ammonia for several hours. The mixture is then allowed to stand overnight at room temperature, the volatiles evaporated and the residue purified, if desired, e.g., by column chromatography.

The amide thus obtained is contacted with thionyl chloride, typically a solvent amount of the latter reagent is employed, and the mixture heated at reflux, typically overnight. The product is isolated by standard methods known in the art, for example, the reaction mixture is poured into water, made alkaline with a strong base, e.g., sodium hydroxide, and extracted with a water-immiscible solvent, e.g., ethyl ether, chloroform or methylene chloride. The nitrile of formula (III, f=1, Q=CN, $R_1$=H) is isolated by evaporation of solvent and, if desired, purified by column chromatography or recrystallization.

The 5-acetoxy alcohols of formula (III, f=1, Q=$CH_2OH$, $R_1$=$COCH_3$) and their counterparts of formula (II) are obtained by selective acylation of the corresponding dihydroxy compounds wherein $R_1$=H. In a preferred such method for selective acylation, the dihydroxy compound is mixed with equimolar amounts of a tertiary alkyl amine, e.g., triethylamine, and a dialkylaminopyridine, e.g., 4-dimethylaminopyridine in the presence of a reaction inert organic solvent. An equimolar amount of acetic anhydride is added at a temperature below room temperature, preferably at −10° to 20° C. and especially 0° to 10° C. The mixture is maintained at such temperature, typically for about one to four hours, then allowed to warm to room temperature and the product isolated, e.g., by extraction and evaporation of the extract to obtain a crude product which is purified by column chromatography. Preferred reaction inert solvents for this reaction include methylene chloride, chloroform and ethyl ether.

The homologous nitriles of formula (III, f=2, Q=CN, $R_1$=$COCH_3$) are obtained from the dihydroxy compounds of formula (III, Q=$CH_2OH$, $R_1$=H) by acetylation as described above to afford the corresponding monoacetyl compound wherein $R_1$=$COCH_3$. The latter compound is then converted to the corresponding alkylsulfonyl or arylsulfonyl ester and this product reacted further with an alkali metal cyanide such as potassium cyanide as employed methods and conditions previously described for the conversion of compounds of formula (II, Q=$CH_2OH$, f=0, $R_1$=$COCH_3$) to the corresponding nitriles wherein f=1.

Hydrolysis of the acetoxy nitrile (III, Q=CN, f=2, $R_1$=$COCH_3$) with a weak base, e.g., aqueous sodium carbonate, affords the corresponding hydroxy nitrile wherein $R_1$=H.

Hydrolysis of the nitriles (III, f=2, Q=CN, $R_1$=H or $COCH_3$) with a strong base, e.g., sodium hydroxide, provides the corresponding carboxylic acids of formula (III, f=2, Q=COOH, $R_1$=H). Esterification of the latter compounds with an alcohol of formula $R_7OH$, by methods described above for the corresponding compounds of formula (II), affords the esters (III, f=2, Q=$COOR_7$, $R_1$=H) where $R_7$ is $C_1$–$C_4$alkyl or benzyl.

Employing methods previously described for the corresponding invention compounds of formula (II), the remaining invention compounds of formula (III) are obtained wherein f=1 or 2 and Q is $CH_2OH$, $CONR_{12}R_{13}$, $CH_2NH_2$, $CH_2NHCOR_{14}$ and $CH_2NHSO_2R_{17}$ as outlined in Flow Chart C, above.

Compounds of formula (I) wherein —Z—W is —(alk$_1$)$_m$—X—(alk$_2$)$_n$—W and X is —SO— or —SO$_2$— are obtained by oxidation of the corresponding compounds in which X is —S—. Hydrogen peroxide is a convenient agent for oxidation of the thio ethers to sulfoxides. Oxidation of the thio ethers to corresponding sulfones is conveniently accomplished by means of a peracid such as perbenzoic, perphthalic or m-chloroperbenzoic acid. This latter peracid is especially useful since the by-product m-chlorobenzoic acid is easily removed.

Group $R_6$, if not already present in compounds of formula (I) where M is $NR_6$, can be introduced into said compounds by reaction of the free base ($R_6$=H) with the appropriate Cl-$R_6$ or Br-$R_6$ reactant according to known procedures. Of course, for such compounds wherein Q contains an hydroxy group, or a primary or secondary amino group, it is often preferred to introduce the group $R_6$ prior to formation of said hydroxy or amino group in Q.

Esters of compounds of formula (I) wherein $R_1$ is benzoyl, alkanoyl or —CO—$(CH_2)_p$—$NR_{15}R_{16}$ are readily prepared by reacting formula (I) compounds wherein $R_1$ is hydrogen with benzoic acid, the appropriate alkanoic acid or acid of formula HOOC—$(CH_2)_p$—$NR_{15}R_{16}$ in the presence of a condensing agent such as dicyclohexylcarbodiimide. Alternatively, they are prepared by reaction of the formula (I) ($R_1$=H) compound with the appropriate acid chloride or anhydride, e.g., benzoyl chloride, acetyl chloride or acetic anhydride, in the presence of a base such as pyridine.

The presence of a basic group in the ester moiety ($OR_1$) in the compounds of this invention permits formation of acid-addition salts involving said basic group. When the herein described basic esters are prepared via condensation of the appropriate amino acid hydrochloride (or other acid addition salt) with the appropriate compound of formula (I) in the presence of a condensing agent, the hydrochloride salt of the basic ester is produced. Careful neutralization affords the free base. The free base form can then be converted to other acid addition salts by known procedures.

Acid addition salts can, of course, as those skilled in the art will recognize, be formed with the nitrogen of the quinoline compounds of formula (I) wherein M is $NR_6$. Such salts are prepared by standard procedures. The basic ester derivatives of these quinoline compounds are, of course, able to form mono- or di-acid addition salts because of their dibasic functionality.

The analgesic properties of the compounds of this invention are determined by tests using thermal nociceptive stimuli, such as the mouse tail flick procedure, or chemical nociceptive stimuli, such as measuring the ability of a compound to suppress phenylbenzoquinone irritant-induced writhing in mice. These tests and others are described below.

Tests Using Thermal Nociceptive Stimuli (a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. At 0.5 and 2 hours after treatment with the test compound, the mouse is observed for the first "flicking" movements of one or both hind feet, or until 10 seconds elapse without such movements. Morphine has an $MPE_{50}$=4–5.6 mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941), using controlled high intensity heat applied to the tail. Each mouse is placed in a snugfitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptacle procedure developed by Benbasset, et. al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each tail is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Mittel Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD-strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack reported in seconds. The clamp is removed in 30 seconds if attacking has not yet occurred, and the latency of response is recorded as 30 seconds. Morphine is active 17.8 mg./kg. (i.p.).

Tests Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72, and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \ MPE = \frac{\text{test time} - \text{control time}}{\text{cutoff time} - \text{control time}} \times 100$$

As mentioned above, the compounds of the invention are especially useful as antiemetic and antinausea agents in mammals. They are particularly useful in preventing emesis and nausea induced by antineoplastic agents.

The antiemetic properties of the compounds of formula (I) are determined in unanesthetized unrestrained cats according to the procedure described in Proc. Soc. Exptl. Biol. and Med., 160, 437–440 (1979).

Antagonism of PGE$_2$* Diarrhea in Mice

*Prostaglandin E$_2$

The antidiarrheal activity of the invention compounds is determined by a modification of the method of Dajani et al., *European Jour. Pharmacol.*, 34, 105–113 (1975). This method reliably elicits diarrhea in otherwise untreated mice within 15 minutes. Pretreated animals in which no diarrhea occurs are considered protected by the test agent. The constipating effects of test agents are measured as an "all or none" response, diarrhea being defined as watery unformed stools, very different from normal fecal matter, which consists of well-formed boluses, firm and relatively dry.

Male albino mice of the Charles River CD-1 strain are used. They are kept in group cages and tested within one week following arrival. The weight range of the animals when tested is between 20–25 g. Pelleted rat chow is available ad libitum until 18 hours prior to testing, at which time food is withdrawn.

Animals are weighed and marked for identification. Five animals are normally used in each drug treatment group. Mice weighing 20–25 g. are housed in group cages, and fasted overnight prior to testing. Water is available ad libitum. Animals are challenged with PGE$_2$ (0.32 mg/kg i.p. in 5% ETOH) one hour after drug treatment, and immediately placed individually in transparent acrylic boxes of 15×15×18 cm. A disposable cardboard sheet on the bottom of the box is checked for diarrhea on an all or nothing basis at the end of 15 minutes. A vehicle +PGE$_2$ treatment group and a vehicle treatment gorup serve as controls in each day's testing.

The data are analyzed using weighted linear regression of probit-response onlog dose, employing the maximum likelihood procedure. A computer program prints results in an analysis of linear regression format, including degrees of freedom, sum of squares, mean squares and critical values of F$_{05}$ and Chi square. If the regression is significant, the ED$_{30}$, ED$_{50}$, ED$_{70}$, and ED$_{90}$ and then 95% confidence limits are calculated.

The compounds of the present invention are active analgesics, antidiarrheals, antiemetics or antinauseants via oral and parenteral administration and are conveniently administered for these uses in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

Suspensions and solutions of these drugs, particularly those wherein R$_1$ is hydroxy, are generally prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

The physician will determine the dosage which will be most suitable for an individual patient and it will vary with the age, weight and response of the particular patient and the route of administration. Generally, however, the initial analgesic dosage, as well as the initial dosage for prevention or treatment of nausea, in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 50 mg./day. The favored parenteral dose is from about 0.01 to about 100 mg./day; the preferred range from about 0.01 to about 20 mg./day.

EXAMPLE 1 dl-5-Hydroxy-2,2-dimethyl-7-(1,1-dimethylheptyl)-3,4-dihydro-2H-benzopyran-4-one A one liter, three-necked flask, fitted with mechanical stirrer, thermometer and ether condenser was flushed with dry nitrogen and 8.5 g (36 mmole) of 1,3-dihydroxy-5-(2,2-dimethylheptyl)benzene and 4.6 g (46.0 mmole) of 3,3-dimethylacrylic acid was added. The mixture was stirred vigorously while heating to 135° C. The thermometer was replaced by an addition funnel with condensor and 11.3 ml (107.4 mmole) of boron trifluoride etherate was added quickly via the addition funnel. Heating is continued for ten minutes, the mixture allowed to cool to room temperature and stirred for an additional ten minutes. To this was added 10 ml of cold water followed by 40 ml of 6N sodium hydroxide and the resulting mixture heated at 80° C. for five minutes. Heat was removed, the mixture acidified with five ml of concentrated hydrochloric acid and cooled to 30° C., at which temperature 200 ml of ethyl ether was added. After stirring for five minutes, the layers were separated and the aqueous phase extracted with 2×50 ml of ether. The combined ether layers were washed in succession with 2×80 ml water, 1×100 ml saturated sodium bicarbonate solution, 3×50 ml of 1N sodium hydroxide, 1×100 ml brine and 1×100 ml water, then dried over anhydrous magnesium sulfate. The ether was evaporated in vacuo to provide 11.8 g of residual oil of sufficient purity for use in the next step.

Alternatively, the crude product was chromatographed on a silica gel column, eluting with ether and hexane. Fractions were monitored by silica gel thin-layer chromatography, eluting with 9:1 hexane/ether by volume, (Rf 0.41) to afford 8.9 g (77.7%) of the desired product, $^1$H-NMR(CDCl$_3$)ppm(delta): 0.80-0.81 (m, 3H), 1.0-1.7 (m, 22H), 2.7 (s, 2H), 6.3-6.7 (m, 2H), 11.6 (s, 1, disappeared upon addition of D$_2$O); Infrared (KBr), cm$^{-1}$: 3400(OH), 2899(CH), 1639(C=O); Mass spectrum (m/e): M$^+$318.

Analysis: Calc'd for C$_{20}$H$_{30}$O$_3$: C, 75.43; H, 9.50. Found: C, 75.40; H, 9.54.

EXAMPLE 1A

The procedure of Example 1 is repeated but using the appropriate acid, R$_4$R$_5$C=CHCOOH, in place of dimethylacrylic acid and the appropriate 5-ZW-substituted-1,3-dihydroxybenzene (prepared as described in U.S. Pat. No. 4,143,139) to give the following compounds.

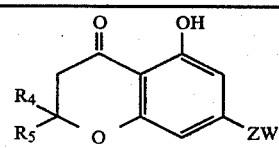

| R$_5$ | R$_4$ | Z | W |
|---|---|---|---|
| H | H | CH(CH$_3$)(CH$_2$)$_3$ | C$_6$H$_5$ |
| H | CH$_3$ | CH(CH$_3$)(CH$_2$)$_3$ | C$_6$H$_5$ |
| H | C$_2$H$_5$ | CH(CH$_3$)(CH$_2$)$_3$ | C$_6$H$_5$ |
| H | CH$_3$ | CH(CH$_3$)(CH$_2$)$_4$ | C$_6$H$_5$ |
| H | H | CH(CH$_3$)(CH$_2$)$_3$ | C$_6$H$_5$ |
| H | H | (CH$_2$)$_3$ | C$_6$H$_5$ |
| H | H | (CH$_2$)$_4$ | C$_6$H$_5$ |
| H | C$_2$H$_5$ | (CH$_2$)$_4$ | C$_6$H$_5$ |
| H | H | (CH$_2$)$_2$CH(C$_2$H$_5$) | C$_6$H$_5$ |
| H | CH$_3$ | CH(C$_2$H$_5$)(CH$_2$)$_3$ | C$_6$H$_5$ |
| H | H | C(CH$_3$)$_2$ | C$_6$H$_5$ |
| H | CH$_3$ | C(CH$_3$)$_2$(CH$_2$)$_3$ | C$_6$H$_5$ |
| H | H | (CH$_2$)$_6$ | C$_6$H$_5$ |
| H | CH$_3$ | (CH$_2$)$_8$ | C$_6$H$_5$ |
| H | H | CH(CH$_3$)(CH$_2$)$_7$ | C$_6$H$_5$ |
| H | H | CH$_2$ | C$_6$H$_5$ |
| H | H | CH(CH$_3$)(CH$_2$)$_3$ | 4-FC$_6$H$_4$ |
| H | CH$_3$ | CH(CH$_3$)(CH$_2$)$_3$ | 4-FC$_6$H$_4$ |
| H | H | CH(CH$_3$)CH$_2$ | 4-FC$_6$H$_4$ |
| H | C$_2$H$_5$ | CH(CH$_3$)CH$_2$ | 4-FC$_6$H$_4$ |
| H | C$_2$H$_5$ | CH(CH$_3$)(CH$_2$)$_2$ | 4-ClC$_6$H$_4$ |
| H | H | CH(CH$_3$)(CH$_2$)$_2$CH(CH$_3$) | C$_6$H$_5$ |
| H | CH$_3$ | CH$_2$ | C$_6$H$_5$ |
| H | H | (CH$_2$)$_3$ | C$_5$H$_9$ |
| CH$_3$ | CH$_3$ | CH(CH$_3$)(CH$_2$)$_3$ | C$_6$H$_5$ |
| H | CH$_3$ | CH(CH$_3$)CH$_2$ | C$_5$H$_9$ |
| H | H | CH(CH$_3$)(CH$_2$)$_2$ | C$_5$H$_9$ |
| H | H | CH(CH$_3$)(CH$_2$)$_4$ | C$_5$H$_9$ |
| H | H | CH(CH$_3$)CH$_2$ | C$_3$H$_5$ |
| H | H | CH(CH$_3$)CH(CH$_3$) | C$_6$H$_{11}$ |
| H | C$_2$H$_5$ | CH(CH$_3$)CH(CH$_3$) | C$_6$H$_{11}$ |
| H | H | CH(CH$_3$)(CH$_2$)$_5$ | C$_6$H$_{11}$ |
| H | CH$_3$ | CH(CH$_3$)(CH$_2$)$_5$ | C$_6$H$_{11}$ |
| H | H | (CH$_2$)$_4$ | C$_3$H$_5$ |
| H | H | (CH$_2$)$_8$ | C$_6$H$_{11}$ |
| H | C$_2$H$_5$ | (CH$_2$)$_8$ | C$_6$H$_{11}$ |
| H | H | (CH$_2$)$_3$CH(CH$_3$) | C$_6$H$_{11}$ |
| H | CH$_3$ | CH(CH$_3$)(CH$_2$)$_3$ | C$_6$H$_{11}$ |
| H | H | CH(CH$_3$)(CH$_2$)$_2$CH(CH$_3$) | C$_6$H$_{11}$ |
| H | CH$_3$ | CH(CH$_3$)CH(CH$_3$)CH$_2$ | C$_6$H$_{11}$ |
| H | H | (CH$_2$)$_3$ | 2-pyridyl |
| H | H | (CH$_2$)$_3$ | 4-pyridyl |
| H | H | (CH$_2$)$_4$ | 2-pyridyl |
| H | CH$_3$ | (CH$_2$)$_4$ | 4-pyridyl |
| H | C$_2$H$_5$ | (CH$_2$)$_4$ | 3-pyridyl |
| H | CH$_3$ | CH$_2$CH(CH$_3$)CH$_2$ | 4-pyridyl |
| H | C$_2$H$_5$ | CH(CH$_3$)(CH$_2$)$_2$ | 3-pyridyl |
| H | CH$_3$ | CH(CH$_3$)CH(C$_2$H$_5$)CH$_2$ | 4-pyridyl |
| H | H | CH(C$_2$H$_5$)(CH$_2$)$_3$ | 3-pyridyl |
| H | H | CH$_2$CH(C$_2$H$_5$)CH$_2$ | 3-pyridyl |
| H | H | CH(CH$_3$)(CH$_2$)$_2$ | 4-piperidyl |
| H | CH$_3$ | CH(C$_2$H$_5$)(CH$_2$)$_2$ | 2-piperidyl |
| H | CH$_3$ | CH(CH$_3$)(CH$_2$)$_2$CH(CH$_3$) | 4-piperidyl |

-continued

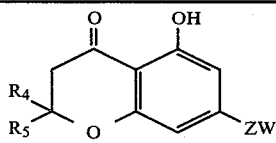

| R₅ | R₄ | Z | W |
|---|---|---|---|
| H | CH₃ | CH(CH₃)(CH₂)₂ | C₇H₁₃ |
| H | H | CH(CH₃)(CH₂)₂ | C₇H₁₃ |
| H | CH₃ | CH(CH₃)CH₂—O—(CH₂)₂ | C₆H₅ |
| H | H | (CH₂)₄ | CH₃ |
| H | CH₃ | CH(CH₃)CH(CH₃)(CH₂)₅ | H |
| H | H | CH(CH₃)CH(CH₃)(CH₂)₅ | H |
| H | H | CH₂ | H |
| H | CH₃ | CH₂ | CH₃ |
| H | H | (CH₂)₃ | CH₃ |
| H | H | (CH₂)₆ | CH₃ |
| H | CH₃ | (CH₂)₆ | CH₃ |
| H | H | CH(CH₃) | CH₃ |
| H | CH₃ | (CH₂)₃ | H |
| H | H | CH(CH₃) | C₆H₁₁ |
| H | C₂H₅ | CH(CH₃)(CH₂)₄ | CH₃ |
| H | H | (CH₂)₃—O— | C₆H₅ |
| H | CH₃ | (CH₂)₃—O— | 4-FC₆H₄ |
| H | CH₃ | (CH₂)₃—O— | C₆H₁₁ |
| H | C₂H₅ | (CH₂)₃—O— | C₄H₇ |
| H | H | (CH₂)₃—O— | CH₃ |
| H | CH₃ | (CH₂)₃—O— | 4-(4-FC₆H₄)C₆H₁₀ |
| H | C₂H₅ | (CH₂)₃—O—(CH₂)₂ | 4-ClC₆H₄ |
| H | H | (CH₂)₃—O—(CH₂)₂ | C₆H₅ |
| H | CH₃ | (CH₂)₃—O—CH(CH₃) | 4-piperidyl |
| H | CH₃ | (CH₂)₃—O—CH(CH₃)(CH₂)₂ | C₆H₅ |
| H | H | (CH₂)₃—O—CH(CH₃)(CH₂)₂ | CH₃ |
| H | H | CH(CH₃)(CH₂)₂—O— | C₆H₅ |
| H | CH₃ | CH(CH₃)(CH₂)₂—O—CH₂ | CH₃ |
| H | CH₃ | CH(CH₃)(CH₂)₂—O—(CH₂)₂ | C₆H₅ |
| H | CH₃ | CH(CH₃)(CH₂)₂—O—(CH₂)₄ | C₆H₅ |
| H | CH₃ | CH(CH₃)(CH₂)₂—O—CH(CH₃) | C₇H₁₃ |
| H | H | CH(CH₃)(CH₂)₂—O—CH₂CH—(C₂H₅) | CH₃ |
| H | CH₃ | (CH₂)₄—O— | C₆H₅ |
| H | H | (CH₂)₄—O—CH(CH₃)CH₂ | 3-piperidyl |
| H | C₂H₅ | (CH₂)₄—O—(CH₂)₅— | 4-pyridyl |
| H | C₂H₅ | (CH₂)₄—O—CH₂ | 4-FC₆H₄ |
| H | H | CH(CH₃)(CH₂)₃—O— | 2-(4-FC₆H₅)C₂H₈ |
| H | CH₃ | CH(CH₃)(CH₂)₃—O—(CH₂)₂ | C₆H₅ |
| H | C₂H₅ | CH(CH₃)(CH₂)₃—O—(CH₂)₂ | CH₃ |
| H | H | CH(C₂H₅)(CH₂)₂—O—(CH₂)₄ | C₆H₅ |
| H | CH₃ | CH(C₂H₅)(CH₂)₂—O—CH(CH₃) | 4-piperidyl |
| H | H | CH(C₂H₅)(CH₂)₂—O—(CH₂)₂—CH(CH₃) | C₇H₁₃ |
| H | CH₃ | CH(CH₃)—O—CH₂ | C₅H₉ |
| H | CH₃ | CH(C₂H₅)(CH₂)₂—O— | C₃H₅ |
| H | H | CH(C₂H₅)(CH₂)₂—O— | 2-(4-FC₆H₁₁)C₇H₁₂ |
| H | H | (CH₂)₃—S— | C₆H₅ |
| H | C₂H₅ | (CH₂)₃—S—CH₂ | 4-FC₆H₄ |
| H | CH₃ | (CH₂)₃—S— | C₅H₉ |
| H | C₂H₅ | (CH₂)₃—S—(CH₂)₂ | CH₃ |
| H | H | (CH₂)₃—S—(CH₂)₄ | C₆H₅ |
| H | CH₃ | CH(CH₃)(CH₂)₂—S— | 4-piperidyl |
| H | CH₃ | CH(CH₃)(CH₂)₂—S— | 4-(C₆H₅)C₆H₁₀ |
| H | CH₃ | CH(CH₃)(CH₂)₂—S—(CH₂)₄ | 4-pyridyl |
| H | CH₃ | CH(CH₃)(CH₂)₂—S—(CH₂)₄ | C₆H₅ |
| H | C₂H₅ | CH(C₂H₅)(CH₂)₂—S— | C₆H₁₁ |
| H | CH₃ | CH(C₂H₅)(CH₂)₂—S—(CH₂)₂—CH(CH₃) | CH₃ |
| H | H | CH(C₂H₅)(CH₂)₂—S—CH(CH₃) | 4-ClC₆H₄ |
| H | H | CH(CH₃)(CH₂)₃—S—(CH₂)₄ | 4-FC₆H₄ |
| H | CH₃ | CH(CH₃)(CH₂)₃—S—(CH₂)₄ | 4-pyridyl |
| H | H | CH(CH₃)CH₂—O—(CH₂)₆ | CH₃ |
| H | CH₃ | CH(CH₃)CH₂—O—(CH₂)₆ | C₆H₅ |
| H | H | CH(CH₃)CH₂—O—(CH₂)₄ | CH₃ |
| H | H | CH(CH₃)CH₂—O—CH(CH₃)CH₂ | C₆H₅ |
| H | CH₃ | CH(CH₃)CH₂—O—CH(CH₃)CH₂ | C₆H₅ |
| H | C₂H₅ | CH(CH₃)CH₂—O—CH(CH₃)CH₂ | C₆H₅ |
| H | CH₃ | CH(CH₃)CH₂—O—CH₂ | 4-FC₆H₄ |
| H | CH₃ | CH(CH₃)CH₂—O—(CH₂)₂ | 4-pyridyl |
| H | H | CH(CH₃)CH₂—O—CH(CH₃) | CH₃ |
| H | H | CH₂CH(CH₃)—O—CH₂ | CH₃ |
| H | C₂H₅ | CH₂CH(CH₃)—O—CH₂ | CH₃ |
| H | CH₃ | CH₂CH(CH₃)—O—(CH₂)₆ | CH₃ |
| H | CH₃ | CH₂CH(CH₃)—O—CH(CH₃)CH₂ | C₆H₅ |
| H | H | CH₂CH(CH₃)—O—(CH₂)₂ | 4-FC₆H₄ |
| H | CH₃ | C(CH₃)₂(CH₂)₆ | H |

-continued

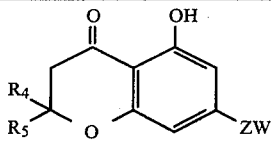

| R5 | R4 | Z | W |
|---|---|---|---|
| H | C2H5 | C(CH3)2(CH2)6 | H |
| CH3 | CH3 | CH(CH3)(CH2)3 | C6H5 |
| C2H5 | C2H5 | CH(CH3)(CH2)3 | C6H5 |
| C2H5 | CH3 | CH(CH3)(CH2)4 | C6H5 |
| CH3 | CH3 | CH(CH3)(CH2)3 | C6H5 |
| H | CH2C6H5 | (CH2)3 | C6H5 |
| H | n-C6H13 | (CH2)4 | C6H5 |
| CH3 | C2H5 | (CH2)4 | C6H5 |
| H | (CH2)4C6H5 | (CH2)2CH(C2H5) | C6H5 |
| CH3 | CH3 | C(CH3)2 | C6H5 |
| CH3 | CH3 | C(CH3)2(CH2)3 | C6H5 |
| C2H5 | C2H5 | (CH2)6 | C6H5 |
| CH3 | CH3 | (CH2)8 | C6H5 |
| CH3 | CH3 | CH(CH3)(CH2)7 | C6H5 |
| H | n-C4H9 | CH2 | C6H5 |
| CH3 | CH3 | CH(CH3)(CH2)3 | 4-FC6H4 |
| CH3 | n-C6H13 | CH(CH3)CH2 | 4-FC6H4 |
| H | (CH2)2C6H5 | CH(CH3)(CH2)2CH(CH3) | C6H5 |
| H | CH3 | CH2 | C6H5 |
| H | CH2C6H5 | (CH2)3 | C5H9 |
| CH3 | CH3 | CH(CH3)CH2 | C5H9 |
| CH3 | CH2C6H5 | CH(CH3)(CH2)2 | C5H9 |
| CH3 | CH3 | CH(CH3)CH2 | C3H5 |
| H | (CH2)3C6H5 | CH(CH3)(CH2)5 | C6H11 |
| CH3 | CH3 | CH(CH3)(CH2)5 | C6H11 |
| CH3 | n-C4H9 | (CH2)4 | C3H5 |
| CH3 | CH3 | (CH2)9 | C6H11 |
| CH3 | CH3 | (CH2)3 | 2-pyridyl |
| CH3 | CH2C6H5 | (CH2)3 | 4-pyridyl |
| CH3 | CH3 | (CH2)4 | 4-pyridyl |
| C2H5 | C2H5 | (CH2)4 | 3-pyridyl |
| CH3 | CH3 | CH(CH3)CH(C2H5)CH2 | 4-pyridyl |
| H | n-C5H11 | CH(C2H5)(CH2)3 | 3-pyridyl |
| H | i-C3H7 | CH(CH3)(CH2)2 | 4-piperidyl |
| CH3 | CH3 | CH(C2H5)(CH2)2 | 2-piperidyl |
| CH3 | CH3 | CH(CH3)(CH2)2CH(CH3) | 4-piperidyl |
| CH3 | CH3 | CH(CH3)(CH2)2 | C7H13 |
| H | n-C4H9 | CH(CH3)(CH2)2 | C7H13 |
| CH3 | CH3 | CH(CH3)CH2—O—(CH2)2 | C6H5 |
| CH3 | CH2C6H5 | (CH2)4 | CH3 |
| CH3 | CH3 | CH(CH3)CH(CH3)—(CH2)5 | H |
| C2H5 | C2H5 | CH(CH3)CH(CH3)—(CH2)5 | H |
| CH3 | CH3 | CH2 | H |
| CH3 | C2H5 | (CH2)3 | CH3 |
| H | n-C6H13 | (CH2)6 | CH3 |
| CH3 | (CH2)3C6H5 | CH(CH3) | CH3 |
| CH3 | CH3 | (CH2)3 | H |
| H | n-C4H9 | CH(CH3) | C6H11 |
| CH3 | CH3 | (CH2)3—O— | C6H5 |
| CH3 | CH3 | (CH2)3—O— | 4-FC6H4 |
| CH3 | CH3 | (CH2)3—O— | C6H11 |
| C2H5 | C2H5 | (CH2)3—O— | C4H7 |
| H | CH2C6H5 | (CH2)3—O— | CH3 |
| CH3 | CH3 | (CH2)3—O— | 4-(4-FC6H4)C6H10 |
| C2H5 | C2H5 | (CH2)3—O—(CH2)2 | 4-ClC6H4 |
| CH3 | CH3 | (CH2)3—O—CH(CH3) | 4-piperidyl |
| H | n-C5H11 | CH(CH3)(CH2)2—O— | C6H5 |
| CH3 | CH3 | CH(CH3)(CH2)2—O—CH2 | CH3 |
| CH3 | CH3 | CH(CH3)(CH2)2—O—(CH2)4 | C6H5 |
| CH3 | CH3 | CH(CH3)(CH2)2—O—CH—(CH3) | C7H13 |
| CH3 | CH3 | CH(CH3)(CH2)2—O—CH2—CH(C2H5) | CH3 |
| CH3 | CH3 | (CH2)4—O— | C6H5 |
| C2H5 | C2H5 | (CH2)4—O—CH(CH3)CH2 | 3-piperidyl |
| CH3 | C2H5 | (CH2)4—O—CH2 | 4-FC6H4 |
| H | n-C3H7 | CH(CH3)(CH2)3—O— | 2-(4-FC6H5)C2H8 |
| CH3 | CH3 | CH(CH3)(CH2)3—O—(CH2)2 | C6H5 |
| CH3 | CH3 | CH(C2H5)(CH2)2—O—CH(CH3) | 4-piperdyl |
| CH3 | CH3 | CH(C2H5)(CH2)2—O— | C3H5 |
| CH3 | CH3 | CH(C2H5)(CH2)2—O— | 2-(4-FC6H11)C7H12 |
| CH3 | CH3 | (CH2)3—S | C6H5 |
| C2H5 | C2H5 | (CH2)3—S—CH2 | 4-FC6H4 |
| CH3 | CH3 | (CH2)3—S— | C5H9 |
| CH3 | CH2C6H5 | (CH2)3—S—(CH2)4 | C6H5 |

-continued

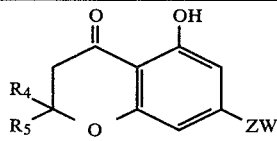

| R5 | R4 | Z | W |
|---|---|---|---|
| CH3 | CH3 | CH(CH3)(CH2)2—S— | 4-piperidyl |
| CH3 | CH3 | CH(CH3)(CH2)2—S—(CH2)4 | 4-pyridyl |
| CH3 | CH3 | CH(CH3)(CH2)2—S—(CH2)4 | C6H5 |
| C2H5 | C2H5 | CH(C2H5)(CH2)2—SO | C6H11 |
| H | n-C6H13 | CH(C2H5)(CH2)2—S—CH(CH3) | 4-ClC6H4 |
| CH3 | n-C4H9 | CH(CH3)(CH2)3—S—(CH2)4 | 4-FC6H4 |
| CH3 | CH3 | CH(CH3)(CH2)3—S—(CH2)4 | 4-pyridyl |
| CH3 | CH3 | CH(CH3)CH2—O—(CH2)6 | C6H5 |
| CH3 | CH3 | C(CH3)2(CH2)6 | H |
| C2H5 | C2H5 | C(CH3)2(CH2)6 | H |

Alternate methods for preparing the above compounds are described in U.S. Pat. No. 4,143,139.

EXAMPLE 1B dl-5-Hydroxy-2,2-dimethyl-7-(5-phenyl-2-pentyloxy)-3,4-dihydro-2H-benzopyran-4-one A mixture of 5-phenyl-2-pentanol (16.4 g, 100 mM), triethylamine (28 ml, 200 mM) and dry tetrahydrofuran (80 ml) under a nitrogen atmosphere is cooled in an ice/water bath. Methanesulfonyl chloride (8.5 ml, 110 mM) in dry tetrahydrofuran (20 ml) is added dropwise at such a rate that the temperature holds essentially constant. The mixture is allowed to warm to room temperature and is then filtered to remove triethylamine hydrochloride. The filter cake is washed with dry tetrahydrofuran and the combined wash and filtrate evaporated under reduced pressure to give the product as an oil. The oil is dissolved in chloroform (100 ml) and the solution washed with water (2×100 ml) and then with saturated brine (1×20 ml). Evaporation of the solvent affords 21.7 g (89.7%) yield of 5-phenyl-2-pentanol mesylate which is used in the next step without further purification.

A mixture of 2,2-dimethyl-5,7-dihydroxy-4-chromanone (2.08 g, 10 mM), potassium carbonate (2.76 g, 20 mM), N,N-dimethylformamide (10 ml) and 5-phenyl-2-pentanol mesylate (2.64 g, 11 mM), under a nitrogen atmosphere, is heated to 80°-82° C. in an oil bath for 1.75 hours. The mixture is cooled to room temperature and then poured into ice/water (100 ml). The aqueous solution is extracted with ethyl acetate (2×25 ml) and the combined extracts washed successively with water (3×25 ml) and saturated brine (1×25 ml). The extract is then dried (MgSO4), decolorized with charcoal and evaporated to give the product as an oil which crystallizes upon seeding with pure product; m.p. 83°-84° C. Yield=quantitative.

In like manner, the following compounds are prepared from appropriate 2,2-R4R5-5,7-dihydroxy-4-chromanones and appropriate alkanols. The necessary alkanol reactants not previously described in the literature are prepared from appropriate aldehydes or ketones via the Wittig reaction as described in U.S. Pat. No. 4,143,139. The same reference describes the preparation of the above 4-chromanone starting materials.

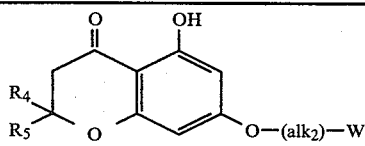

| R4 | R5 | alk2 | W |
|---|---|---|---|
| CH3 | CH3 | CH2C(CH3)2)4 | CH3 |
| CH3 | CH3 | CH2CH(CH3)(CH2)2CH(CH3)CH2 | CH3 |
| CH3 | H | CH(CH3)CH2CH(CH3)CH2CH(CH3) | CH3 |
| CH3 | H | (CH2)2CH(CH3)CH2CH(CH3) | CH3 |
| H | H | CH(CH3)(CH2)2C(CH3)2 | CH3 |
| C2H5 | C2H5 | CH2CH(C2H5) | C6H5 |
| CH3 | C2H5 | CH2CH2CH(CH3) | C6H5 |
| CH3 | CH3 | (CH2)4 | C6H5 |
| H | H | (CH2)4CH(C2H5) | C6H5 |
| H | CH3 | (CH2)7 | C6H5 |
| H | H | CH(CH3)(CH2)5 | C6H5 |
| C2H5 | H | (CH2)9 | C6H5 |
| CH3 | CH3 | (CH2)9 | CH3 |
| H | CH3 | CH(CH3)CH2 | 2-pyridyl |
| H | C2H5 | CH2C(CH3)2 | 2-pyridyl |
| H | CH3 | (CH2)3 | 2-pyridyl |
| C2H5 | CH3 | (CH2)2 | 2-pyridyl |
| H | H | (CH2)2 | 4-pyridyl |
| CH3 | CH3 | (CH2)3 | 3-pyridyl |
| CH3 | H | (CH2)3 | 4-pyridyl |
| CH3 | C2H5 | (CH2)4 | 2-pyridyl |
| H | H | (CH2)3 | 2-piperidyl |
| CH3 | H | (CH2)3 | 4-piperidyl |
| CH3 | CH3 | (CH2)3 | 4-FC6H4 |
| H | H | (CH2)3 | 4-ClC6H4 |
| C2H5 | H | (CH2)4 | C6H5 |
| C2H5 | H | (CH2)4 | 4-FC6H4 |
| H | H | CH(CH3)(CH2)2 | 2-pyridyl |
| C2H5 | C2H5 | CH(CH3)(CH2)2 | 3-pyridyl |
| CH3 | CH3 | CH(CH3)(CH2)3 | 4-pyridyl |
| CH3 | CH3 | CH(CH3)(CH2)2 | 4-piperidyl |
| H | CH3 | CH(C2H5)(CH2)2 | 2-pyridyl |
| CH3 | CH3 | CH(C2H5)(CH2)2 | 4-pyridyl |
| C2H5 | CH3 | CH(C2H5)(CH2)2 | 4-piperidyl |
| H | C2H5 | CH(CH3)(CH2)2 | 4-FC6H4 |
| CH3 | H | CH(CH3)(CH2)2 | 4-ClC6H4 |
| CH3 | CH3 | CH2 | C6H5 |
| H | H | CH2 | C6H5 |
| CH3 | CH3 | CH2 | 4-FC6H4 |
| CH3 | CH3 | — | C6H5 |
| CH3 | CH3 | — | 4-FC6H4 |
| C2H5 | H | — | 4-ClC6H4 |
| C2H5 | C2H5 | — | C6H5 |
| H | H | — | 4-FC6H4 |
| CH3 | CH3 | — | C3H5 |
| H | H | — | C3H5 |
| CH3 | CH3 | — | C4H7 |
| CH3 | H | — | C4H7 |
| C2H5 | C2H5 | — | C5H9 |
| CH3 | CH3 | — | C5H9 |

-continued

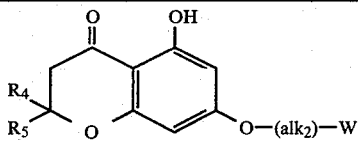

| R4 | R5 | alk2 | W |
|---|---|---|---|
| CH3 | H | — | C6H11 |
| CH3 | H | — | C7H13 |
| CH3 | CH3 | — | 2-(C6H5)C3H4 |
| CH3 | CH3 | — | 1-(C6H5)C4H6 |
| CH3 | CH3 | — | 2-(C6H5)C5H8 |
| CH3 | H | — | 2-(C6H5)C5H8 |
| CH3 | CH3 | — | 2-(C6H5)C6H10 |
| C2H5 | C2H5 | — | 3-(C6H5)C6H10 |
| CH3 | CH3 | — | 4-pyridyl |
| CH3 | CH3 | — | 4-piperidyl |
| CH3 | H | — | 2-(C6H5)C6H10 |
| H | H | — | 4-(C6H5)C6H10 |
| CH3 | CH3 | — | 3-(C6H5)7H12 |
| CH3 | CH3 | —CH2— | CH3 |
| CH3 | CH3 | —(CH2)3— | CH3 |
| CH3 | CH3 | —(CH2)6— | CH3 |
| CH3 | CH3 | —(CH2)9— | CH3 |
| CH3 | H | —(CH2)6— | CH3 |
| C2H5 | C2H5 | —(CH2)3— | CH3 |
| CH3 | CH3 | —C(CH3)2(CH2)5— | CH3 |
| CH3 | H | —C(CH3)2(CH2)5— | CH3 |
| CH3 | CH3 | —CH(CH3)CH(CH3)(CH2)4— | CH3 |

EXAMPLE 1C dl-5-Hydroxy-2,2-dimethyl-7-(2-heptylmercapto)-3,4-dihydro-2H-benzopyran-4-one To a solution of 5-hydroxy-7-mercapto-2,2-dimethyl-4-chromanone (19.7 g, 87.1 mM) and potassium hydroxide (2.44 g, 43.5 mM) in N,N-dimethylformamide (58 ml) is added with stirring 2-bromoheptane (15.77 g, 88.0 mM). The mixture is heated for four days at 100° C., cooled to room temperature and then added to a mixture of aqueous sodium hydroxide (110 ml of 1N), water (45 ml) and chloroform (150 ml). The mixture is agitated, the phases separated and the aqueous layer extracted with more chloroform (150 ml). The combined chloroform layers are washed with 1N sodium hydroxide (2×100 ml), dried over sodium sulfate and concentrated to an oil. The unreacted 2-bromoheptane is removed by distillation and the residue purified by silica gel chromatography to give the title product.

The following compounds are similarly prepared from appropriate reactants of the formula Br-(alk2)n-W from the appropriate 5-hydroxy-7-mercapto-2,2-R4R5-substituted-4-chromanone, preparation of which is described in U.S. Pat. No. 4,143,139.

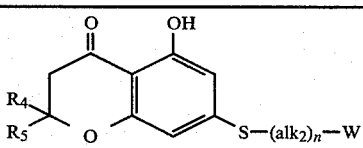

| R4 | R5 | n | (alk2) | W |
|---|---|---|---|---|
| H | CH3 | 1 | —CH(CH3)(CH2)4— | CH3 |
| C2H5 | C2H5 | 1 | —CH(CH3)(CH2)4— | CH3 |
| CH3 | CH3 | 1 | —CH(CH3)(CH2)3— | C6H5 |
| H | CH3 | 1 | —CH(CH3)(CH2)3— | C6H5 |
| CH3 | CH3 | 1 | —CH(CH3)(CH2)2— | C6H5 |
| CH3 | CH3 | 1 | —CH(CH3)(CH2)3— | 4-pyridyl |
| H | H | 1 | —CH(CH3)(CH2)3— | 4-pyridyl |
| CH3 | CH3 | 1 | —CH2— | C6H5 |

-continued

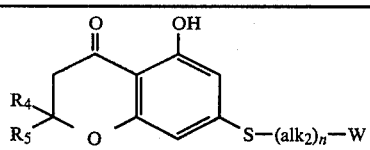

| R4 | R5 | n | (alk2) | W |
|---|---|---|---|---|
| CH3 | CH3 | 1 | —(CH2)4— | C6H5 |
| CH3 | C2H5 | 1 | —(CH2)7— | C6H5 |
| CH3 | CH3 | 1 | —C(CH3)2(CH2)5— | CH3 |
| CH3 | H | 1 | —C(CH3)2(CH2)5— | CH3 |
| CH3 | CH3 | 1 | —CH(CH3)CH(CH3)(CH2)4— | CH3 |
| H | CH3 | 1 | —CH(CH3)CH(CH3)(CH2)4— | CH3 |
| CH3 | CH3 | 1 | —(CH2)3— | 3-pyridyl |
| CH3 | H | 1 | —(CH2)3— | 4-pyridyl |
| H | CH3 | 1 | —CH(CH3)CH2— | 2-pyridyl |
| H | H | 1 | —(CH2)2— | 4-pyridyl |
| C2H5 | CH3 | 1 | —CH(CH3)(CH2)2 | 4-piperidyl |
| CH3 | CH3 | 0 | — | C6H5 |
| CH3 | CH3 | 0 | — | C6H11 |
| H | CH3 | 0 | — | 4-FC6H4 |
| C2H5 | H | 0 | — | 4-ClC6H4 |
| C2H5 | C2H5 | 0 | — | C6H5 |
| CH3 | CH3 | 0 | — | C3H5 |
| H | H | 0 | — | C3H5 |
| CH3 | CH3 | 0 | — | C4H7 |
| CH3 | CH3 | 0 | — | C5H9 |
| CH3 | CH3 | 0 | — | C7H13 |
| CH3 | H | 0 | — | C7H13 |
| CH3 | CH3 | 0 | — | 2-(C6H5)C3H4 |
| CH3 | CH3 | 0 | — | 2-(C6H5)C5H8 |
| CH3 | CH3 | 0 | — | 4-(C6H5)C6H10 |
| CH3 | CH3 | 0 | — | 3-(C6H5)C7H12 |
| H | H | 0 | — | 4-(C6H5)C6H10 |
| CH3 | CH3 | 0 | — | 4-pyridyl |
| CH3 | CH3 | 0 | — | 4-piperidyl |

EXAMPLE 2 dl-5-Benzyloxy-2,2-dimethyl-7-(1,1-dimethylheptyl)-3,4-dihydro-2H-benzopyran-4-one To a flask containing 3.52 g (45 mmole) of potassium hydride, 50% oil suspension, which had been washed five times with pentane to remove the oil by decantation was added 50 ml of N,N-dimethylformamide (DMF) which had been purified by stirring overnight with calcium hydride and distillation. The mixture was stirred and cooled to 0° C., 11.8 g (36 mmole) of crude 5-hydroxy-2,2-dimethyl-7-(1,1-dimethylheptyl)-3,4-dihydro-2H-benzopyran-4-one in 100 ml of purified DMF was added dropwise at such a rate that the temperature of the reaction mixture did not exceed 6° C. (about 20 minutes). The mixture was then allowed to warm to room temperature and stirred for one hour. The reaction mixture was cooled to 3° C., a solution of 4.4 ml (37 mmole) benzyl bromide in 50 ml of DMF was added dropwise over ten minutes while maintaining the mixture below 8° C. The mixture was allowed to warm to room temperature and stirred for four hours. The reaction was quenched by slow, dropwise addition of 10 ml of water, diluted with 500 ml of ethyl ether, washed with 1×150 ml water, 3×150 ml 0.1N hydrochloric acid, 1×100 ml water, 1×150 ml saturated sodium bicarbonate solution, 1×150 ml brine and 1×150 ml water. The washed ethereal solution was dried over anhydrous magnesium sulfate, the solvent evaporated in vacuo and the residual oil (15 g) purified by chromatography on 200 g of silica gel (40–63 microns) eluting with pentane and ethyl acetate. Evaporation of the product containing fractions afforded 8.8 g (60%) of solid material. Recrystallization from hexane or pentane afforded crystals, m.p. 52°-52.5° C. ¹H-NMR(CDCl₃)ppm(delta): 0.85 (s, 3H), 1.0–1.8 (m, 22H), 2.7 (s, 2H), 6.5 (s, 2H), 7.2–7.8 (m, 5H); Mass spectrum (m/e): M+ 408.

Analysis: Calc'd for $C_{27}H_{30}O_3$: C, 79.37; H, 8.88. Found: C, 79.22; H, 8.74.

EXAMPLE 3 dl-5-Benzyloxy-4-ethoxycarbonylmethyl-4-hydroxy-2,2-dimethyl-7-(1,1-dimethylheptyl)-3,4-dihydro-2H-benzopyran A. To a 200 ml, three-necked flask equipped with a magnetic stirrer, addition funnel and nitrogen inlet, was charged 11.36 ml (25 mmole) of 2.2 molar n-butyl lithium in hexane at −78° C. The solution was diluted with 12 ml of tetrahydrofuran (THF) which had been treated with sodium metal and distilled. A solution of 4.52 g (25 mmole) of dicyclohexylamine in 12 ml of the same THF was added dropwise via the addition funnel. To the resulting slurry was added dropwise 2.44 ml (25 mmole) of ethyl acetate and the resulting mixture stirred at −78° C. for 15 minutes. To this was added dropwise 10.01 g (24.5 mmole) of 5-benzyloxy-2,2-dimethyl-7-(1,1-dimethylheptyl)-3,4-dihydro-2H-benzopyran-4-one dissolved in 30 ml of the same THF. The resulting mixture was stirred at −78° C. for three hours after which the reaction was quenched by addition of 2 ml (35 mmole) of glacial acetic acid. The mixture was allowed to warm to room temperature, 50 ml of saturated sodium bicarbonate solution followed by 50 ml of ethyl ether was added. The layers were separated, the organic layer washed with 3×35 ml of cold 1N hydrochloric acid, 1×30 ml of saturated sodium bicarbonate solution, 1×30 ml of water and the organic layer dried over anhydrous magnesium sulfate. Evaporation of solvent afforded 12.5 g of residual oil. This was purified by chromatography on 200 g of silica gel (40–63 microns), eluting with 4 liters of ethyl ether/low boiling petroleum ether (2:23 by volume) and 2 liters of the same solvents mixed in a ratio of 5:20 by volume. The combined product fractions were evaporated to afford 9.0 g (74.5%) of purified product. Rf 0.22 on silica gel TLC using a 1:1 by volume ether/hexane solvent system. ¹H-NMR(CDCl₃)ppm(delta): 0.72 (s, 3H), 0.90 (t, 3H), 1.03 (s, 6H), 1.12 (s, 3H), 1.18 (s, 3H), 1.70 (d, 1H), 2.05 (d, 1H), 2.42 (d, 1H), 2.57 (d, 1H), 3.07 (s, 1H), 3.30 (q, 2H), 4.28 (s, 2H), 5.42 (s, 2H), 5.42 (s, 2H), 6.08–6.38 (m, 5H); Infrared spectrum (film), cm⁻¹: 3560(OH), 3030(CH, aromatic), 2925 (CH, aliphatic), 1710(C=O); Mass spectrum (m/e): M+ 496, 478 (M-18, base peak).

B. Alternatively, this product is made by the following procedure.

Zinc metal (13 g, 0.2 mole) is covered with a small amount of dimethoxymethane. The mixture is heated at reflux and a solution of 16.7 g (0.1 mole) ethyl bromoacetate in 75 ml of dimethoxymethane is added over 20 minutes. After refluxing for 30 minutes, the mixture is cooled to 0°–5° C. and 40.85 g (0.10 mole) dl-5-benzyloxy-2,2-dimethyl-7-(1,1-dimethylheptyl)-3,4-dihydro-2H-benzopyran-4-one is added dropwise. The mixture is stirred at 0°–5° C. for one hour, allowed to warm to room temperature and stirred overnight. Ammonium hydroxide, 25 ml, is added, the mixture extracted with ethyl ether and isolated as described in Part A above, to afford the desired product.

Use of the appropriate acetate ester in place of ethylacetate in the above procedures affords the following compounds in like manner.

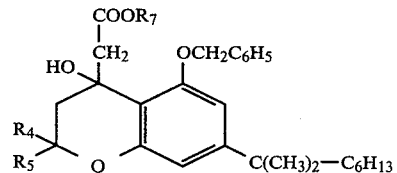

where R₇ is methyl, isopropyl, n-propyl, n-butyl or isobutyl.

EXAMPLE 3A dl-4,5-Dihydroxy-4-methoxycarbonylmethyl-2,2-dimethyl-7-(1,1-dimethylheptyl)-3,4-dihydro-2H-benzopyran A mixture of 655 mg (1.37 mmole) 5-benzyloxy-4-ethoxycarbonylmethyl-4-hydroxy-2,2-dimethyl-7(1,1-dimethylheptyl)-3,4-dihydro-2H-benzopyran, 133 mg 5% palladium-on-calcium carbonate and 50 ml methanol was hydrogenated at 38 psi (2.7 kg/cm²) until hydrogen uptake ceased. The mixture was filtered, the filtrate evaporated in vacuo and the residual oil taken up in hexane. Upon cooling, crystals formed which were collected by filtration, 66 mg. The mother liquor was evaporated in vacuo to an oil, pentane added and the mixture refrigerated overnight. Filtration gave an additional 179 mg of product. ¹H-NMR(CDCl₃)ppm(delta): 3.00 (dd, 2H), 3.20 (s, 2H), 3.70 (s, 3H), 4.90 (s, 1H), 6.35 (m, 2H), 7.65 (s, 1H).

EXAMPLE 4 dl-5-Hydroxy-4-methoxycarbonylmethyl-2,2-dimethyl-7-(1,1-dimethylheptyl)-3,4-dihydro-2H-benzopyran and its corresponding lactone

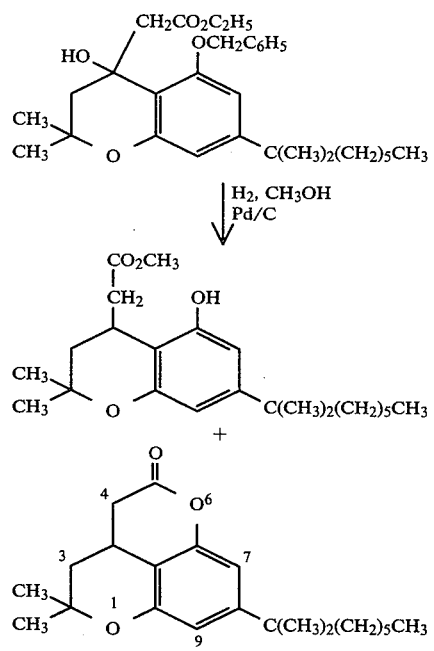

In a 500 ml pressure bottle was placed a solution of 8.55 g (17.2 mmole) of 5-benzyloxy-4-ethoxycarbonylmethyl-4-hydroxy-2,2-dimethyl-7-(1,1-dimethylheptyl)-3,4-dihydro-2H-benzopyran in 250 ml of methanol. One gram of 5% palladium-on-carbon catalyst was added and the mixture was shaken under hydrogen at 40 psi. (2.8 kg/cm$^2$) for 17 hours. The reaction mixture was filtered through anhydrous magnesium sulfate and the solvent evaporated in vacuo. The residue was partitioned between 100 ml of ethyl ether and 50 ml of water, the aqueous layer extracted again with 50 ml of ether and the combined ether extracts washed with 30 ml saturated sodium bicarbonate solution and 30 ml water. The ether was dried over anhydrous magnesium sulfate and the solvent evaporated in vacuo to obtain a mixture of methyl ester and lactone from which the former product crystallizes upon standing. After recrystallization from low boiling petroleum ether, purified methyl ester was obtained, m.p. 72°–73° C. $^1$H-NMR(CDCl$_3$)ppm(delta): 0.82 (s, 3H), 1.0–1.5 (m, 20H), 1.53–2.6 (m, 4H), 3.1–3.6 (m, 3H), 3.68 (s, 3H), 5.8 (s, 1H), 6.2–6.4 (m, 2H); Infrared spectrum (KBr), cm$^{-1}$: 3390(OH), 2924(CH, aliphatic), 1745(C=O); Mass spectrum (m/e): M$^+$ 376, base peak 260.

Analysis: Calc'd for $C_{23}H_{36}O_4$: C, 73.36; H, 9.64. Found: C, 73.38; H, 9.51.

Purification of the mother liquors by silica gel chromatography afforded the lactone: 2,2-dimethyl-8-(1,1-dimethylheptyl)-3,3a,4,5-tetrahydro-2H-pyrano[4,3,2-de]benzopyran-5-one.

$^1$H-NMR(CDCl$_3$)ppm(delta): 0.85 (s, 3H), 1.03–1.83 (m, 20H), 1.87–3.17 (m, 5H), 3.2–3.7 (m, 2H), 6.4 (s, 1H), 6.6 (s, 1H); Infrared spectrum (film), cm$^{-1}$: 3025(CH, aromatic), 2925(CH, aliphatic), 1660(C=O); Mass spectrum (m/e): 343 M$^+$, base peak 260.

Analysis: Calc'd for $C_{22}H_{32}O_3$: C, 76.70; H, 9.31. Found: C, 76.38; H, 9.54.

The remaining homologous esters provided in Example 3 are employed to obtain the following compounds in like manner when the above hydrogenation is carried out in the corresponding alcohol, R$_7$OH, where R$_7$ has the values given in Example 3.

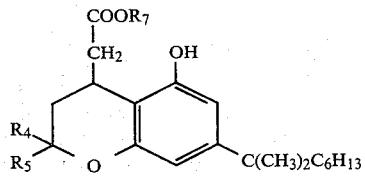

EXAMPLE 4A

By employing the procedure of Example 2, but with the appropriate benzopyran-4-one selected from those provided in Examples 1A, 1B and 1C, and carrying the product thus obtained through the procedure of Example 3, but employing an ester R$_2$R$_3$CHCOOR$_7$ in place of ethyl acetate, followed by hydrogenolysis of the hydroxyester in an alcohol of formula R$_7$OH in place of methanol in the procedure of Example 4, compounds of the formulae below are similarly obtained from each of the starting benzopyran-4-ones.

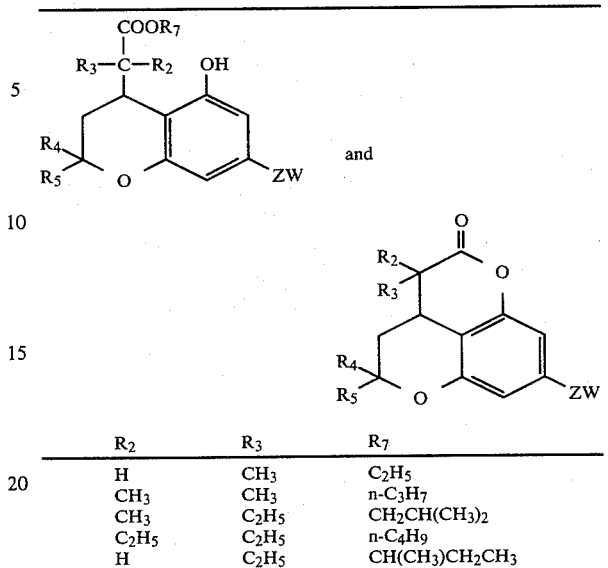

| R$_2$ | R$_3$ | R$_7$ |
|---|---|---|
| H | CH$_3$ | C$_2$H$_5$ |
| CH$_3$ | CH$_3$ | n-C$_3$H$_7$ |
| CH$_3$ | C$_2$H$_5$ | CH$_2$CH(CH$_3$)$_2$ |
| C$_2$H$_5$ | C$_2$H$_5$ | n-C$_4$H$_9$ |
| H | C$_2$H$_5$ | CH(CH$_3$)CH$_2$CH$_3$ |

EXAMPLE 5 dl-5-Hydroxy-4-(2-hydroxyethyl)-2,2-dimethyl-7-(1,1-dimethylheptyl)-3,4-dihydro-2H-benzopyran A 125 ml, round-bottomed flask equipped with a magnetic stirrer and nitrogen inlet was thoroughly flushed with dry nitrogen. Lithium aluminum hydride, 158 mg (4.2 mmole) and 50 ml of dry ethyl ether were added and the suspension stirred and cooled in an ice bath. To the cooled mixture was added slowly 1.44 g (4.2 mmole) of 5-hydroxy-4-methoxycarbonylmethyl-2,2-dimethyl-7-(1,1-dimethylheptyl)-3,4-dihydro-2H-benzopyran dissolved in 20 ml of ether. The cooling bath was removed and the reaction mixture stirred at room temperature for 12 hours. Ethyl acetate, 50 ml, was cautiously added to quench the reaction. The resulting mixture was washed with 50 ml each of saturated sodium bicarbonate solution, brine and water. The organic layer was dried over anhydrous magnesium sulfate, solvent evaporated in vacuo and the crude oil (1.5 g) was purified by chromatography on 25 g of silica gel (48–63 microns), eluting with pentane and ethyl acetate. The desired product, Rf 0.125 on silica gel TLC employing 1:1 ether/toluene by volume, amounted to 1.0 g (69%). $^1$H-NMR(CDCl$_3$)ppm(delta): 0.83 (s, 3H), 1.0–1.67 (m, 23H), 1.7–2.1 (m, 2H), 2.7–3.3 (m, 2H), 3.83 (t, 2H), 6.4 (s, 2H), 7.4–7.9 (s, broad, 1H); Infrared spectrum (film), cm$^1$: 3333(OH), 2545(CH); Mass spectrum (m/e): M$^+$ 348, 264, base peak.

Analysis: Calc'd for $C_{22}H_{36}O_3$: C, 76.70; H, 9.36. Found: C, 77.36; H, 9.67.

When the lactone: 5,5-dimethyl-8-(1,1-dimethylheptyl)-3,3a,4,5-tetrahydro-2H-pyrano[4,3,2-de]benzopyran-2-one or its mixtures with the methyl ester employed above were reduced by the above procedure the title compound was obtained in a like manner.

When 1,3-dihydroxy-5-(5-phenyl-2-pentyloxy) benzene is used in place of 1,3-dihydroxy-5-(2,2-dimethylheptyl) benzene in the procedure of Example 1 and the resulting product treated accordingly to the procedures of Examples 2–5, dl-5-hydroxy-4-(2-hydroxyethyl)-2,2-dimethyl-7-(5-phenyl-2-pentyloxy)-3,4-dihydro-2H-benzopyran is similarly obtained.

$^1$H-NMR(CDCl$_3$)ppm(delta): 1.2–1.5 (m, 9H), 1.52–2.3 (m, 8H), 2.4–2.8 (m, 2H), 2.9–3.2 (m, 1H), 3.8 (t, 2H), 4.1–4.5 (m, 1H), 6.0 (s, 2H), 7.2 (s, 5H); Infrared spectrum (film) cm$^{-1}$: 3400(OH), 2980(CH); Mass spectrum: M+ 384, base peak 191.

EXAMPLE 5A

Employing the procedure of Example 5, but starting with the appropriate 7-ZW-substituted-5-hydroxy-4-(R$_2$R$_3$-substituted-alkoxycarbonyl)-2,2-R$_4$R$_5$-substituted-3,4-dihydro-2H-benzopyran provided in Example 4A, the following compounds are obtained in like manner:

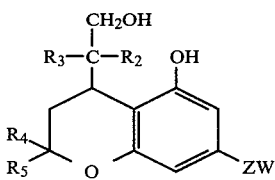

where R$_2$, R$_3$, R$_4$, R$_5$, Z and W are as defined in Example 4A.

EXAMPLE 6 dl-2-Hydroxy-5,5-dimethyl-8-(1,1-dimethylheptyl)-3,3a,4,5-tetrahydro-2H-pyrano[4,3,2-de]benzopyran A solution of 1.80 g (5.2 mmole) 5,5-dimethyl-8-(1,1-dimethylheptyl)-3,3a,4,5-tetrahydro-2H-pyrano-[4,3,2-de]benzopyran-2-one in 25 ml of dry toluene is cooled to −78° C. with stirring. To this was added dropwise 5.2 ml of 1.0M diisobutyl aluminum hydride at such a rate that the temperature of the mixture did not exceed −60° C. (ca. 20 minutes). The resulting mixture was stirred at −78° C. for one hour, after which 4 ml of methanol was added and the mixture allowed to warm to room temperature. Ethyl ether, 75 ml, was added and the mixture was washed with 3×30 ml of sodium potassium tartarate solution, 30 ml of brine and 30 ml of water. The organic phase was dried (MgSO$_4$) and the solvent evaporated in vacuo to afford 1.80 g (100%) of the title hemiacetal.

$^1$H-NMR(CDCl$_3$)ppm(delta): 0.83 (s, 3H), 1.0–1.4 (m, 22H), 1.6–2.3 (m, 4H), 2.8–3.3 (m, 1H), 3.5 (s, broad, 1H), 5.4–5.8 (m, 1H), 6.4 (s, broad, 2H); Infrared spectrum (film), cm$^{-1}$: 3450(OH), 2925(CH); Mass spectrum (m/e): M+ 346, 146 base peak.

Analysis: Calc'd for C$_{22}$H$_{34}$O$_3$: C, 76.26; H, 9.89. Found: C, 75.40; H, 9.45.

When 5,5-dimethyl-8-(5-phenyl-2-pentyloxy)-3,3a,4,5-tetrahydro-2H-pyrano[4,3,2-de]benzopyran-2-one was reduced by the above procedure, 2-hydroxy-5,5-dimethyl-8-(5-phenyl-2-pentyloxy)-3,3a,4,5-tetrahydro-2H-pyrano[4,3,2-de]benzopyran was obtained in 95% yield as an oil. It was identified by $^1$H-NMR spectroscopy; Rf 0.47 upon chromatography on a silica gel plate, solvent system: cyclohexane/ethyl ether, 1:1 v/v, vanillin spray.

In like manner compounds of the following formula are obtained from the corresponding lactones provided in Example 4A.

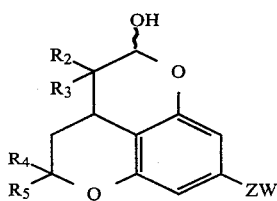

where R$_4$, R$_5$, Z and W have the values given in Examples 1, 1A, 1B and 1C.

EXAMPLE 6A

2-Methoxyamino-5,5-dimethyl-8-(5-phenyl-2-pentyloxy)-3,3a,4,5-tetrahydro-2H-pyrano[4,3,2-de]benzopyran In a stirred flask, under nitrogen, was placed (0.045 mole) 2-hydroxy-5,5-dimethyl-8-(5-phenyl-2-pentyloxy)-3,3a,4,5-tetrahydro-2H-pyrano[4,3,2-de]benzopyran, 250 ml ethanol and 250 ml pyridine. The solution was cooled to 0° C. and 3.94 g (0.047 mole) methoxyamine was added. The resulting mixture was stirred at 0° C. for 2.5 hours, the solvent evaporated in vacuo, the residue taken up in 500 ml ethyl ether and washed twice with water. The aqueous phase was backwashed with ether and the combined ether layers washed with brine and dried over anhydrous magnesium sulfate. The solvent was evaporated in vacuo to obtain 19 g of residual oil. The structure of the product was verified by $^1$H-NMR. Mass spectrum (m/e): 411 (M+), 380 (M-OCH$_3$), 364 (M-NH$_2$OCH$_3$).

A portion of the crude product was purified by column chromatography on silica gel, eluting with ethyl ether. The product-containing fractions were combined and evaporated to afford purified product which showed only one spot on silica gel TLC, Rf 0.58, isopropyl ether solvent, vanillin spray.

EXAMPLE 6B 4-(2-Aminoethyl)-5-hydroxy-2,2-dimethyl-7-(5-phenyl-2-pentyloxy)-3,4-dihydro-2H-benzopyran In a stirred flask, under nitrogen, was placed 17.5 g (0.043 mole) 2-methoxyamino-5,5-dimethyl-8-(5-phenyl-2-pentyloxy)-3,3a,4,5-tetrahydro-2H-pyrano[4,3,2-de]benzopyran in 1800 ml methanol. The mixture was warmed to 40° C. and 1080 ml 1N sodium hydroxide was added in portions over ten minutes. The mixture was heated to 55° C. and 20.4 g Raney Alloy (nickel/aluminum 1:1 by weight) was added in portions over ten minutes (foaming!). The resulting mixture was stirred at 55° C. for one hour, allowed to cool to room temperature and the catalyst removed by filtration. The filtrate was evaporated in vacuo to an oil which was combined with water and 6N hydrochloric acid added to adjust the mixture of pH 6–7. The neutralized mixture was extracted with ethyl acetate, the organic layer backwashed with brine, dried (MgSO$_4$), filtered and the solvent evaporated at reduced pressure to provide 16.4 g crude product as an oil.

The crude product was purified by column chromatography on silica gel, 150 g, eluting with two column volumes of chloroform, then with ethyl acetate/triethylamine, 95:5 v/v. Fractions no. 8 through 20 were combined and evaporated to dryness to provide 6.5 g of starting material. Fractions no. 2 through 5 were evaporated to provide 1.2 g of the desired product, Rf 0.79 on silica gel TLC, ethylacetate/triethylamine, 95:1 v/v, FastBlue spray. $^1$H-NMR(CDCl$_3$)ppm(delta): 7.2 (m, 5H, aromatic), 6.0 (s, 2H, aromatic), 4.8 (s, broad, 3H, NH$_2$ and OH), 4.4 (m, 1H) 1–3 (aliphatic protons).

EXAMPLE 6C

Acylation of the product obtained in Example 6B with a 100% molar excess of 2-furoyl chloride in dichloromethane in the presence of a molar excess of triethylamine at 0° C. for 1.5 hours, followed by evaporation of solvent, dissolving the residue in ethylacetate, washing with water and aqueous sodium bicarbonate solution, drying and evaporation to dryness afforded a crude product. This was stirred at room temperature in methanol containing 1.5 equivalents (based on starting hydroxyamine) of 1N sodium hydroxide for 24 hours. The solvent was evaporated, the residue partitioned between ethyl acetate and water, the organic layer dried (MgSO$_4$) and solvent evaporated to provide 4-[2-(2-furoylamino)ethyl]-5-hydroxy-2,2-dimethyl-7-(5-phenyl-2-pentyloxy)-3,4-dihydro-2H-benzopyran as an oil in 66% yield; Rf 0.58; Mass spectrum (m/e) parent peak 487.

In like manner the following 4-acylaminoethyl analogs were obtained as oils.

| | | (CH$_2$)$_2$NHCOR$_{14}$ structure with OH, CH$_3$, CH$_3$, O, OCH(CH$_3$)(CH$_2$)$_3$C$_6$H$_5$ |

| R$_{14}$ | R$_f$ | Comment |
|---|---|---|
| CH$_3$* | 0.43 | 55% yield, $^1$H—NMR(CDCl$_3$),ppm(delta): 7.0 (5H—aromatic), 6.0 (2H—aromatic), 4.2 (1H). |
| CF$_3$ | — | 28% yield, $^1$H—NMR(CDCl$_3$), ppm(delta): 7.2 (6H, 5-aromatic plus OH), 6.5 (broad, NH), 6.0 (2H—aromatic). |
| C$_6$H$_5$* | 0.63 | 63% yield, Mass spectrum (m/e): 477 (parent). |
| OC$_2$H$_5$ | 0.77 | 78% yield, Mass spectrum (m/e): 455 (M$^+$), 404 (M—HOC$_2$H$_5$). |

*Prepared from acid anhydride rather than acid chloride and employed pyridine in place of triethylamine.

EXAMPLE 7 dl-5-Hydroxy-4-(2-hydroxy-2-methylpropyl)-2,2-dimethyl-7-(1,1-dimethylheptyl)-3,4-dihydro-2H-benzopyran A solution of 344 mg (1 mmole) of 2,2-dimethyl-8-(1,1-dimethylheptyl)-3,3a,4,5-tetrahydro-2-H-pyrano[4,3,2-de]benzopyran-5-one in 10 ml of ethyl ether was cooled in an ice bath for 15 minutes. To the cold solution was added slowly by injection 0.80 ml of 2.9 molar methylmagnesium iodide in ethyl ether. The resulting mixture was allowed to warm to room temperature and stirred for 14 hours. Crystalline ammonium chloride (ca. 100 mg) was added, the mixture stirred for 20 minutes, water (5 ml) added and the layers separated. The aqueous layer was extracted with 10 ml of ether and the combined ether layers were washed with 30 ml of saturated sodium bicarbonate solution, 30 ml of brine and 30 ml of water. The washed organic layer was dried (MgSO$_4$) and solvent separated in vacuo to afford 348 mg of an oil which crystallized upon standing. Recrystallization from pentane afforded 250 mg (66.5%) of purified product, m.p. 101°–103° C.

$^1$H-NMR(CDCl$_3$)ppm(delta): 0.83 (s, 3H), 1.0–1.5 (m, 28H), 1.53–2.5 (m, 5H), 2.9–3.2 (m, 1H), 6.3 (d, 1H), 6.4 (d, 1H), 7.8–8.6 (m, 1H); Infrared spectrum (KBr), cm$^{-1}$: 3333(OH), 2899(CH); Mass spectrum (m/e): M$^+$ 376, base peak 274.

Analysis: Calc'd for C$_{24}$H$_{40}$O$_3$: C, 76.55; H, 10.71. Found: C, 76.61; H, 10.45.

EXAMPLE 7A

By the procedure of Example 7, but employing one of the esters, lactones or mixtures thereof provided in Examples 4 and 4A as starting material and use of the appropriate Grignard reagent of formula R$_8$MgHal where Hal is Cl, Br or I in place of methylmagnesium iodide, the following compounds are obtained in like manner.

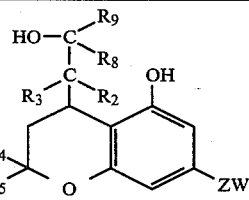

| R$_2$ | R$_3$ | R$_8$ | R$_9$ |
|---|---|---|---|
| H | H | C$_6$H$_5$ | C$_6$H$_5$ |
| H | H | C$_6$H$_5$CH$_2$ | C$_6$H$_5$CH$_2$ |
| H | H | n-C$_4$H$_9$ | n-C$_4$H$_9$ |
| H | CH$_3$ | CH$_3$ | CH$_3$ |
| H | CH$_3$ | C$_2$H$_5$ | C$_2$H$_5$ |
| CH$_3$ | CH$_3$ | CH$_3$ | CH$_3$ |
| CH$_3$ | CH$_3$ | n-C$_3$H$_7$ | n-C$_3$H$_7$ |
| CH$_3$ | CH$_3$ | C$_6$H$_5$ | C$_6$H$_5$ |
| CH$_3$ | C$_2$H$_5$ | CH$_2$CH(CH$_3$)$_2$ | CH$_2$CH(CH$_3$)$_2$ |
| CH$_3$ | C$_2$H$_5$ | C$_6$H$_5$CH$_2$ | C$_6$H$_5$CH$_2$ |
| C$_2$H$_5$ | C$_2$H$_5$ | C$_2$H$_5$ | C$_2$H$_5$ |
| C$_2$H$_5$ | C$_2$H$_5$ | CH(CH$_3$)$_2$ | CH(CH$_3$)$_2$ |
| H | C$_2$H$_5$ | C$_2$H$_5$ | C$_2$H$_5$ |
| H | C$_2$H$_5$ | C$_6$H$_5$ | C$_6$H$_5$ |
| H | C$_2$H$_5$ | CH$_3$ | CH$_3$ |
| H | C$_2$H$_5$ | CH(CH$_3$)$_2$ | CH(CH$_3$)$_2$ |

EXAMPLE 8 dl-5-Hydroxy-4-(2-hydroxypropyl)-2,2-dimethyl-7-(1,1-dimethylheptyl)-3,4-dihydro-2H-benzopyran The hemiacetal obtained in Example 6, dl-5-hydroxy-2,2-dimethyl-8-(1,1-dimethylheptyl)-3,3a,4,5-tetrahydro-2H-pyrano[4,3,2-de]benzopyran, (491 mg, 1.42 mmole) was dissolved in 10 ml of diethyl ether and cooled in an ice bath for 15 minutes. From a syringe 1.58 ml of 2.9M methylmagnesium iodide was added slowly with stirring. The reaction mixture was allowed to warm to room temperature and stirred for three hours. Ammonium chloride crystals (ca. 100 mg) was added to consume the unreacted Grignard reagent and the mixture stirred for 20 minutes. Ethyl acetate, 75 ml, and water, 50 ml, were added, the mixture stirred for a few minutes, and the layers separated. The aqueous layer was extracted with 50 ml of ethyl acetate and the combined organic layers washed with 50 ml each of water, brine and water again. The organic layer was dried over anhydrous magnesium sulfate and solvent evaporated in vacuo to provide 525 mg of crude oil. The oil was chromatographed on a pair of 2 mm thickness silica gel plates employing an ethyl acetate/pentane (1:3 by volume) solvent system. The region with Rf 0.09–0.21 was extracted with 200 ml of ethyl acetate for 2–3 hours to afford 300 mg of product (58.3%).

$^1$H-NMR(CDCl$_3$)ppm(delta): 0.70 (s, 3H), 0.78–1.35 (m, 25H), 1.40–1.87 (m, 4H), 2.41–2.77 (m, 1H), 2.85–3.50 (m, 1H), 6.44–6.60 (m, 2H), 7.52–8.35 (broad 1H); Infrared spectrum (film), cm$^{-1}$: 3350(OH, very broad), 2925(CH); Mass spectrum (m/e): M+ 362, base peak 44.

Analysis: Calc'd for C$_{23}$H$_{38}$O$_3$: C, 76.19; H, 10.57. Found: C, 75.97; H, 10.16.

EXAMPLE 8A

Employing the appropriate lactol provided in Example 6 as starting material in each case, compounds of the formula shown below are obtained by the procedure of Example 8 but employing the appropriate Grignard reagent, R$_8$MgHal where Hal is Cl, Br or I.

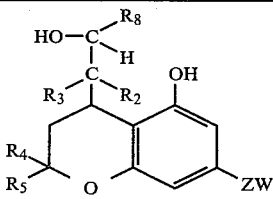

| R$_2$ | R$_3$ | R$_8$ |
|---|---|---|
| H | H | C$_2$H$_5$ |
| H | H | C$_6$H$_5$CH$_2$ |
| H | H | CH(CH$_3$)CH$_2$CH$_3$ |
| H | CH$_3$ | n-C$_3$H$_7$ |
| H | CH$_3$ | CH(CH$_3$)$_2$ |
| H | CH$_3$ | C$_6$H$_5$ |
| CH$_3$ | CH$_3$ | C$_6$H$_5$ |
| CH$_3$ | CH$_3$ | n-C$_4$H$_9$ |
| CH$_3$ | CH$_3$ | CH$_3$ |
| CH$_3$ | C$_2$H$_5$ | C$_2$H$_5$ |
| CH$_3$ | C$_2$H$_5$ | C$_6$H$_5$CH$_2$ |
| C$_2$H$_5$ | C$_2$H$_5$ | CH$_2$CH(CH$_3$)$_2$ |
| C$_2$H$_5$ | C$_2$H$_5$ | C$_2$H$_5$ |
| H | C$_2$H$_5$ | C$_6$H$_5$ |
| H | C$_2$H$_5$ | n-C$_4$H$_9$ |
| H | C$_2$H$_5$ | C$_2$H$_5$ |
| H | C$_2$H$_5$ | C$_6$H$_5$CH$_2$ |

EXAMPLE 9

5-Methoxy-2,2-dimethyl-8-(1,1-dimethylheptyl)-3,3a,4,5-tetrahydro-2H-pyrano[4,3,2-de]benzopyran, the 5-alpha-methoxy and 5-beta-methoxy diastereomers thereof In a 500 ml pressure bottle was placed 346 mg (1 mmole) of dl-5-hydroxy-2,2-dimethyl-8-(1,1-dimethylheptyl)-3,3a,4,5-tetrahydro-2H-pyrano[4,3,2-de]benzopyran, 700 mg (13 mmole) of ammonium chloride, 250 ml of methanol and 350 mg of 5% palladium-on-carbon catalyst. The mixture was shaken with hydrogen at 40 psi (2.8 kg/cm$^2$) for 14 hours, filtered through anhydrous magnesium sulfate and solvent evaporated in vacuo. The residue was partitioned between 25 ml each of ethyl ether and water, the layers separated and the aqueous layer extracted with 2×25 ml of ether. The combined ether layers were dried (MgSO$_4$) and solvent evaporated in vacuo to afford 270 mg of oil which contained a mixture of diastereomeric products. The oil was purified by column chromatography on 10 g of silica gel (48–60 micron) eluting with 100 ml of pentane followed by 300 ml of 99:1 (by volume) pentane/ethyl acetate. The first product eluted was the 5-alpha-methoxy diastereomer (115 mg) followed by a mixture of diastereomers (111 mg) and the 5-beta-methoxy diastereomer (25 mg). Combined yield 251 mg (69.7%). The Rf of the 5-alpha and 5-beta isomers on silica gel TLC using ethyl acetate/pentane (3:22 by volume) were 0.71 and 0.61, respectively. Physical properties were determined for the 5-alpha-methoxy diastereomer as follows:

$^1$H-NMR(CDCl$_3$)ppm(delta): 0.7–1.0 (m, 3H), 1.1–1.5 (m, 22H), 1.6–2.4 (m, 4H), 2.7–3.4 (m, 1H), 3.6 (s, 3H), 5.1–5.3 (m, 1H), 6.4 (s, 2H); Infrared spectrum (KBr), cm$^{-1}$: 3333(OH), 2930(CH); Mass spectrum (m/e): M+ 360, base peak 329.

Analysis: Calc'd for C$_{23}$H$_{36}$O$_3$: C, 76.62; H, 10.07. Found: C, 76.41; H, 10.09. Physical properties of the 5-beta-methoxy diastereomer were:

$^1$H-NMR(CDCl$_3$)ppm(delta): 0.86–1.0 (m, 3H), 1.1–1.4 (m, 22H), 1.6–2.5 (m, 4H), 2.67–3.4 (m, 1H), 3.67 (s, 3H), 5.3 (q, 1H, J=10, J=4), 6.4–6.6 (m, 2H).

When the above procedure is repeated but without the use of hydrogen, catalyst or pressure and addition of a catalytic amount of anhydrous hydrogen chloride, and the resulting mixture stirred at room temperature and pressure overnight, the same products are obtained in like manner.

EXAMPLE 9A

In a similar manner the compounds below are obtained from the appropriate alkanol, R$_{11}$OH, and the appropriate lactone by the procedure of Example 9.

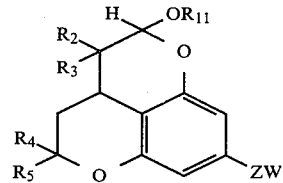

where R$_4$, R$_5$, Z and W have the values assigned in Examples 1, 1A, 1B and 1C and R$_2$,R$_3$ and R$_{11}$ are as shown below.

| R$_2$ | R$_3$ | R$_{11}$ |
|---|---|---|
| H | H | C$_2$H$_5$ |
| H | H | n-C$_4$H$_9$ |
| H | CH$_3$ | CH$_3$ |
| H | CH$_3$ | CH$_2$CH(CH$_3$)$_2$ |
| CH$_3$ | CH$_3$ | n-C$_3$H$_7$ |
| CH$_3$ | CH$_3$ | CH$_3$ |
| CH$_3$ | C$_2$H$_5$ | C$_2$H$_5$ |
| CH$_3$ | C$_2$H$_5$ | CH(CH$_3$)$_2$ |
| C$_2$H$_5$ | C$_2$H$_5$ | C$_2$H$_5$ |
| C$_2$H$_5$ | C$_2$H$_5$ | n-C$_4$H$_9$ |
| H | C$_2$H$_5$ | CH$_3$ |
| H | C$_2$H$_5$ | n-C$_3$H$_7$ |

EXAMPLE 10 dl-5-Benzyloxy-4-cyanomethyl-4-hydroxy-2,2-dimethyl-7-(1,1-dimethylheptyl)-3,4-dihydro-2H-benzopyran n-Butyl lithium, 0.68 ml of 2.2M in hexane, (1.48 mmole) was mixed with 0.68 ml of tetrahydrofuran (THF) which had been distilled from sodium metal. The resulting solution was cooled to −78° C. with stirring and 0.077 ml (1.48 mmole) of acetonitrile added. The resulting slurry was stirred for one hour at −78° C., then a solution of 604 mg (1.48 mmole) of 5-benzyloxy- 2,2-dimethyl-7-(1,1-dimethylheptyl-3,4-dihydro-2H-benzopyran-4-one in 4 ml of the same THF was added dropwise to the stirred suspension by a syringe. When the addition was completed, the resulting mixture was stirred for 5 minutes, allowed to warm to room temperature, stirred 10 minutes and the reaction quenched by addition of 0.1 ml of acetic acid. The mixture was diluted with ethyl ether, washed with 2×20 ml of saturated sodium bicarbonate solution, 20 ml water, dried (MgSO$_4$) and the solvent removed in vacuo to provide 660 mg of the desired product as an oil.

$^1$H-NMR(CDCl$_3$)ppm(delta): 0.83–1.0 (m, 3H), 1.1–1.6 (m, 22H), 2.1 (s, broad, 2H), 2.8 (d, 1H, J=15), 3.4 (d, 1H, J=15), 5.16 (s, 2H), 6.54 (s, 2H), 7.4 (s, 5H); Infrared spectrum (film) cm$^{-1}$: 2941(CH).

In the same manner dl-5-benzyloxy-4-cyanomethyl-4-hydroxy-2,2-dimethyl-7-(5-phenyl-2-pentyloxy)3,4-dihydro-2H-benzopyran was obtained from the appropriate starting material by the above procedure. A quantitative yield of crude product was obtained as a yellow oil. It was used in the next step without purification.

EXAMPLE 11 dl-5-Hydroxy-4-cyanomethyl-2,2-dimethyl-7-(5-phenyl-2-pentyloxy)-3,4-dihydro-2H-benzopyran A. dl-5-Benzyloxy-4-cyanomethylene-2,2-dimethyl-7-(5-phenyl-2-pentyloxy)-3,4-dihydro-2H-benzopyran To a solution of 11.5 g (23.7 mmole) dl-5-benzyloxy-4-cyanomethyl-4-hydroxy-2,2-dimethyl-7-(5-phenyl-2-pentyloxy)-3,4-dihydro-2H-benzopyran in 100 ml dry toluene was added a few grams of molecular sieves and 5 drops of methanesulfonic acid. The mixture was stirred for 16 hours at room temperature, washed with 30 ml water, 2×30 ml saturated sodium bicarbonate solution, dried (MgSO$_4$), filtered and the filtrate evaporated in vacuo to afford a yellow oil. Trituration with ethyl ether, filtration gave 2.60 g colorless solid. Evaporation of the mother liquor to half-volume and addition of petroleum ether afforded a second crop, 3.75 g. Total yield: 6.35 g (60.4%).

$^1$H-NMR(CDCl$_3$)ppm(delta): 5.10 (s, 2H, OCH$_2$C$_6$H$_5$), 6.10 (m, 2H, aromatic), 6.43 (1H, NCCH═C), 7.25 (s, 5H phenyl), 7.45 (s, 5H, —CH$_2$C$_6$H$_5$).

B. dl-5-Benzyloxy-4-cyanomethyl-2,2-dimethyl-7-(5-phenyl-2-pentyloxy)-3,4-dihydro-2H-benzopyran In a flask equipped with magnetic stirrer, thermometer and nitrogen inlet capillary, 1.0 g of the product of Part A, above, 20 ml anhydrous methanol and 2.08 g magnesium turnings were combined. Three crystals of iodine was added at ambient temperature and the mixture stirred until the temperature reached 30° C. It was then cooled to 4° C. and stirred at this temperature for 1.5 hours, then overnight at room temperature. An NMR spectrum of a sample at this time showed the reaction to be incomplete. An additional 2.0 g of magnesium turnings and 20 ml methanol were added. After adding an iodine crystal, the reaction mixture was stirred until the temperature reached 20° C. and gas evolution was well underway. After cooling to −10° C., stirring was continued at −10° to −4° C. for one hour. The cooling bath was removed, the temperature allowed to reach 40° C., then cooled to 20° C. and stirred for four hours. The reaction mixture was cooled to −4° C., 40 ml of 6N hydrochloric acid and 20 ml methanol were added over 20 minutes while maintaining the temperature below 10° C. When the bulk of the magnesium was consumed, the temperature was allowed to rise to ambient temperature and 20 ml ethyl ether added. The mixture was poured into a separatory funnel, 250 ml ether added and after shaking, the layers were separated. The aqueous phase was extracted again with 125 ml ether and the combined ether layers were washed successively with water (100 ml), saturated sodium bicarbonate solution (100 ml) and water (100 ml). The extracts were dried (MgSO$_4$) and solvent evaporated to afford 0.95 g of the product as an oil.

$^1$H-NMR(CDCl$_3$)ppm(delta): 5.10 (s, 2H, OCH$_2$C$_6$H$_5$), 6.10 (m, 2H, aromatic), 7.23 (s, 5H, phenyl), 7.42 (s, 5H, OCH$_2$C$_6$H$_5$).

C. The product of Part B, above, 1.6 g (3.4 mmole) was dissolved in 150 ml anhydrous ethanol and 1.1 g 5% Pd/C was added. The mixture was hydrogenated at 45 psi (3.1 kg/cm$^2$) for 16 hours, filtered and the filtrate evaporated in vacuo to afford 1.0 g of an oily foam. This was taken up in 100 ml methylene chloride, 5 g of silica gel was added and the slurry evaporated. The residual solid was placed on top of a column of 100 g silica gel and eluted with 1.7 liters 4:1 hexane/ethyl ether (v/v) then with 2 liters of 3:1 hexane/ethyl ether. Like fractions were combined and evaporated to dryness in vacuo to provide 590 mg of the desired product.

$^1$H-NMR(CDCl$_3$)ppm(delta): 5.98 (m, 2H, aromatic), 7.23 (5H, phenyl).

EXAMPLE 12 dl-5-Acetoxy-4-(2-hydroxyethyl)-2,2-dimethyl-7-(1,1-dimethylheptyl)-3,4-dihydro-2H-benzopyran A solution of 3.48 g (0.01 mole) dl-5-hydroxy-4-(2-hydroxyethyl)-2,2-dimethyl-7-(1,1-dimethylheptyl)-3,4-dihydro-2H-benzopyran in 50 ml methylene chloride and containing 1.01 g (0.01 mole) triethylamine is cooled to 0° C. while stirring in a nitrogen atmosphere. To this is added a solution of 1.22 g (0.01 mole) 4-dimethylaminopyridine in 5 ml of methylene chloride followed by 1.02 g (0.01 mole) acetic anhydride. After stirring at 0°–5° C. for one hour, the mixture is allowed to warm to room temperature, extracted with methylene chloride and the extracts washed with sodium bicarbonate. After drying over anhydrous magnesium sulfate and evaporation of solvent, the desired product is obtained. It can be purified by column chromatography on silica gel if desired.

The dihydroxy compounds provided in Examples 5A, 7, 7A, 8 and 8A are converted to the corresponding 5-acetoxy derivatives of the following formula in like manner.

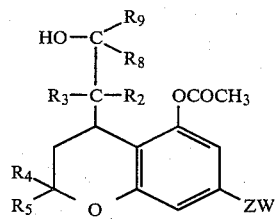

The substituents R$_2$, R$_3$, R$_4$, R$_5$, R$_8$, R$_9$, Z and W are as defined in Examples 5A, 7, 7A, 8 and 8A.

Substitution of acetic anhydride by benzoic anhydride, propionic anhydride, butyric anhydride or valeryl anhydride in this procedure affords the corresponding 5-benzoyloxy, 5-propionyloxy, 5-butyryloxy and 5-valeryloxy derivatives.

EXAMPLE 13 dl-5-Hydroxy-4-(1-methyl-2-cyanoethyl)-2-methyl-7-(5-phenyl-2-pentyl)-3,4-dihydro-2H-benzopyran A. dl-5-Acetoxy-4-(1-methyl-2-methanesulfonyloxyethyl)-2-methyl-7-(5-phenyl-2-pentyl)-3,4-dihydro-2H-benzopyran To 4.11 g (0.01 mole) dl-5-acetoxy-4-(1-methyl-2-hydroxyethyl)-2-methyl-7-(5-phenyl-2-pentyl)-3,4-dihydro-2H-benzopyran dissolved in 45 ml pyridine under a nitrogen atmosphere at 0°–5° C. is added with stirring 1.25 g (0.011 mole) methanesulfonyl chloride. The resulting mixture is stirred at 5° C. for 30 minutes, warmed to room temperature and stirred for an additional hour. The reaction mixture is concentrated in vacuo, the residue taken up in ethyl acetate, washed with water, brine and dried over anhydrous magnesium sulfate. Evaporation of solvent gives the desired mesylate of sufficient purity for use in the next step.

B. A mixture of 4.57 g (0.01 mole) of the mesylate obtained in Part A, above, 6.5 g (0.01 mole) potassium cyanide, 800 mg potassium iodide, 90 g dimethylformamide and 10 ml water is heated at 85°–95° C. for two hours. The solvent is evaporated in vacuo, the residue extracted with chloroform, the extracts washed with water, brine and dried (MgSO$_4$). Evaporation of solvent affords the desired nitrile which is purified by chromatography on a silica gel column.

In like manner the remaining dihydroxy compounds provided in Examples 5 and 5A are converted to the 5-acetoxy derivatives by the procedure of Example 12 and the 5-acetoxy derivative, in turn, converted to a nitrile of the formula shown below.

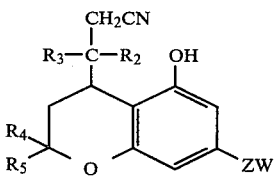

where R$_2$, R$_3$, R$_4$, R$_5$, Z and W are as defined in Examples 5 and 5A.

EXAMPLE 14 dl-3-[5-Hydroxy-2-methyl-7-(5-phenyl-2-pentyl)-3,4-dihydro-2H-benzopyran-4-yl]butyric acid To a mixture of 125 ml of methanol and 75 ml 1N sodium hydroxide is added 3.77 g (0.01 mole) dl-5-hydroxy-4-(1-methyl-2-cyanoethyl)-2-methyl-7-(5-phenyl-2-pentyl)-3,4-dihydro-2H-benzopyran and the resulting mixture is heated at reflux overnight. The methanol is evaporated and the residue is extracted between chloroform, backwashing with dilute sodium hydroxide solution. The aqueous alkaline layers are combined, acidified with hydrochloric acid and extracted with chloroform. The extracts are dried over anhydrous magnesium sulfate and the solvent evaporated to provide the desired product.

In like manner the remaining nitriles provided in Examples 11 and 13 are hydrolyzed to the corresponding acid of the formula

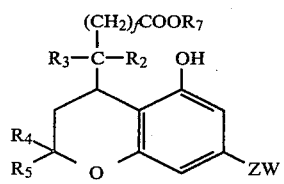

where f is 0 or 1, R$_7$ is hydrogen, R$_2$, R$_3$, R$_4$, R$_5$, Z and W are as defined in Examples 5, 5A and 11.

Heating the above acids, dissolved in a molar excess of alkanol, R$_7$OH, at 50°–110° C. for 4–24 hours in the presence of a catalytic amount of hydrogen chloride or concentrated sulfuric acid provides the corresponding esters of the above formula wherein R$_7$ is methyl, ethyl, n-propyl, isobutyl, n-butyl or benzyl.

Acetylation of the above 5-hydroxy-carboxylic acids and esters by the Example 12 affords the corresponding 5-acetoxy derivatives.

EXAMPLE 14A

Lithium aluminum hydride reduction of the 4-[C(R$_2$R$_3$)CH$_2$COOR$_7$]benzopyran esters provided in Example 14 by the procedure of Example 5 affords the following primary alcohols:

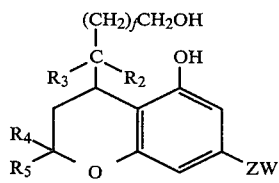

where f is 0 or 1 and R$_2$, R$_3$, R$_4$, R$_5$, Z and W are as defined in Examples 5, 5A and 11.

EXAMPLE 14B

Reaction of the 4-[C(R$_2$R$_3$)CH$_2$COOR$_7$]benzopyran esters provided in Example 14 with Grignard reagents (R$_8$MgCl or R$_8$MgBr) by the procedure of Example 7 affords the following tertiary alcohols:

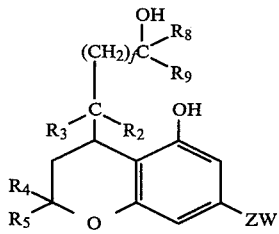

where f is 0 or 1 and R$_2$, R$_3$, R$_4$, R$_5$, Z and W are as defined in Examples 5, 5A and 11 and R$_8$ and R$_9$ are as defined in Example 7A.

EXAMPLE 15 dl-4-(4-Amino-2-butyl)-5-hydroxy-2-methyl-7-(5-phenyl-2-pentyl)-3,4-dihydro-2H-benzopyran Under anhydrous conditions and a nitrogen atmosphere, to a solution of 190 mg (5 mmole) lithium aluminum hydride in 50 ml tetrahydrofuran at 10° C. is added dropwise a solution of 1.885 g (5 mmole) dl-5-hydroxy-4-(1-methyl-2-cyanoethyl)-2-methyl-7-(5-phenyl-2-pentyl)-3,4-dihydro-2H-benzopyran in 25 ml of tetrahydrofuran. After the addition is complete, the mixture is stirred at room temperature for 6 hours. Ethyl acetate is added to consume the unreacted hydride. The reaction mixture is evaporated to dryness, the residue partitioned between water and methylene chloride and the organic layer dried over anhydrous magnesium sulfate. The solvent is evaporated to provide the title compound as the free base.

The hydrochloride salt of the title compound is obtained by adding an ethereal solution of hydrogen chloride to a solution of the free base in anhydrous ethanol. The precipitated salt is collected by filtration, washing with ether and air drying.

When the above procedure is repeated, but using dl-5-hydroxy-4-cyanomethyl-2,2-dimethyl-7-(1,1-dimethylheptyl)-3,4-dihydro-2H-benzopyran as starting material, the product obtained is dl-4-(2-aminoethyl)-5-hydroxy-2,2-dimethyl-7-(1,1-dimethylheptyl-3,4-dihydro-2H-benzopyran.

In like manner the remaining nitriles provided in Example 11 are converted to amines of the formula shown below wherein f is zero. Similarly, the remaining compounds of Example 13 are reduced to amines of the formula below wherein f is 1.

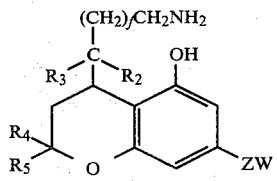

$R_2$, $R_3$, $R_4$, $R_5$, Z and W are as defined in Examples 11 and 13.

EXAMPLE 16 dl-5-Acetoxy-4-(4-acetylamino-2-butyl)-2-methyl-7-(5-phenyl-2-pentyl)-3,4-dihydro-2H-benzopyran To a solution of 3.81 g (0.01 mole) dl-4-(amino-2-butyl)-5-hydroxy-2-methyl-7-(5-phenyl-2-pentyl)-3,4-dihydro-2H-benzopyran in 25 ml of chloroform and 18 ml dry pyridine at 10° C. is added 2.36 ml (0.032 mole) acetyl chloride which is dissolved in 10 ml chloroform. The resulting solution is stirred overnight at room temperature, poured onto ice/water, the organic layer separated and the aqueous phase extracted with chloroform. The combined organic layers are washed with saturated sodium bicarbonate, water, brine and dried over anhydrous magnesium sulfate. Evaporation of solvent affords the title compound which is purified, if desired, by column chromatography on silica gel.

When the above procedure is repeated, but using dl-4-(2-aminoethyl)-5-hydroxy-2,2-dimethyl-7-(1,1-dimethylheptyl)-3,4-dihydro-2H-benzopyran, the product obtained is dl-5-acetoxy-4-(2-acetylaminoethyl)-2,2-dimethyl-7-(1,1-dimethylheptyl)-3,4-dihydro-2H-benzopyran.

When acetyl chloride is replaced by an equimolar amount of benzoyl chloride, propionyl chloride, isobutyryl chloride, valeryl chloride, 2-phenylacetyl bromide, trifluoroacetic anhydride or 2-furoyl chloride, the corresponding amido ester compounds are obtained.

In like manner the remaining compounds provided in Example 15 are converted to compounds of the formula shown below.

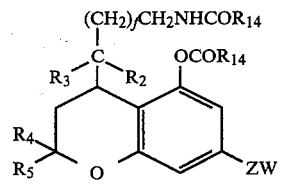

wherein f is zero or one, $R_2$, $R_3$, $R_4$, $R_5$, Z and W are as defined in Examples 1A, 1B, 1C and 4A, and $R_{14}$ is as shown below.

$R_{14}$ $CH_3$
$C_2H_5$
$i-C_4H_9$
$n-C_5H_{11}$
$CF_3$
$C_6H_5CH_2$
2-furyl
3-thienyl
4-pyridyl
3-furyl
2-thienyl
$C_6H_5$
$4-NH_2C_6H_4$
$2-ClC_6H_4$
$3-BrC_6H_4$
$3-CH_3C_6H_4$
$4-CH_3OC_6H_4$
$4-FC_6H_4$

EXAMPLE 17 dl-4-(4-Acetylamino-2-butyl)-5-hydroxy-2-methyl-7-(5-phenyl-2-pentyl)-3,4-dihydro-2H-benzopyran A solution of 156 mg (0.335 mmole) dl-5-acetoxy-4-(4-acetylamino-2-butyl)-2-methyl-7-(5-phenyl-2-pentyl)-3,4-dihydro-2H-benzopyran and 46 mg (0.333 mmole) potassium carbonate in 40 ml of methanol is stirred at room temperature for two hours. After neutralization with acetic acid the mixture is evaporated in vacuo and the residue taken up in ethyl ether. The ether solution is washed successively with water, saturated sodium bicarbonate, brine and dried over magnesium sulfate. Evaporation of ether affords the title amide.

In like manner the remaining 5-acyloxy amides provided in Example 16 are hydrolyzed to the corresponding 5-hydroxy amides of the formula

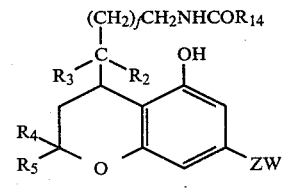

where f, $R_2$, $R_3$, $R_4$, $R_5$, $R_{14}$, Z and W are as defined in Example 16.

EXAMPLE 18 dl-4-(4-Acetylamino-2-butyl)-2-methyl-7-(5-phenyl-2-pentyl)-5-(4-N-piperidylbutyryloxy)-3,4-dihydro-2H-benzopyran hydrochloride To a solution of 1.06 g (2.5 mmole) dl-4-(4-acetylamino-2-butyl)-5-hydroxy-2-methyl-7-(5-phenyl-2-pentyl)-3,4-dihydro-2H-benzopyran in 20 ml methylene chloride is added 0.52 g (2.5 mmole) 4-N-piperidylbutyric acid hydrochloride, 0.573 g (2.78 mmole) of dicyclohexylcarbodiimide and the mixture stirred at room temperature for six hours. It is cooled at 0° C. overnight, filtered, the filtrate evaporated and the residue triturated with ethyl ether to afford the desired hydrochloride salt.

Alternatively, the above filtrate is extracted with dilute hydrochloric acid. The aqueous phase is washed with ether, then neutralized with potassium hydroxide solution and extracted with ether. Evaporation affords the free base of the title compound.

Repetition of this procedure but using the appropriate 5-hydroxy compound selected from those of Example 17 and the appropriate alkanoic acid or acid of formula $R_{15}R_{16}N(CH_2)_p$—COOH.HCl affords the following compounds

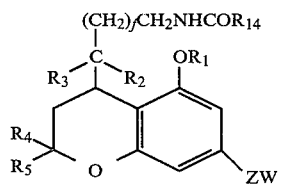

wherein f, $R_2$, $R_3$, $R_4$, $R_5$, $R_{14}$, Z and W are as defined in Example 17 and $R_1$ is as defined below.

$R_1$

COCH$_2$CH$_3$
CO(CH$_2$)$_2$CH$_3$
CO(CH$_2$)$_3$CH$_3$
COCH$_2$NH$_2$
CO(CH$_2$)$_2$NH$_2$
CO(CH$_2$)$_4$NH$_2$
CO(CH$_2$)N(CH$_3$)$_2$
CO(CH$_2$)$_2$NH(C$_2$H$_5$)
CO(CH$_2$)$_4$NHCH$_3$
CONH$_2$
CON(C$_2$H$_5$)$_2$
CON(C$_4$H$_9$)$_2$
CO(CH$_2$)$_3$NH(C$_3$H$_7$)
CO(CH$_2$)$_2$N(C$_4$H$_9$)$_2$
COCH$_2$-piperidino
COCH$_2$-pyrrolo
CO(CH$_2$)$_2$-morpholino
CO(CH$_2$)$_2$-N-butylpiperazino
CO(CH$_2$)$_3$-pyrrolidino
CO-piperidino
CO-morpholino
CO-pyrrolo
CO-N-(methyl)piperazino
CO-C$_6$H$_5$
COCH(CH$_3$)(CH$_2$)$_2$-piperidino
CHO Basic esters are obtained as their hydrochloride salts. Careful neutralization with sodium hydroxide affords the free basic esters.

EXAMPLE 19 dl-4-(4-Methanesulfonylamino-2-butyl)-5-hydroxy-2-methyl-7-(5-phenyl-2-pentyl)-3,4-dihydro-2H-benzopyran Sulfonylation employing the procedure of Example 16, but replacing the acetyl chloride used therein with an equimolar amount of methanesulfonyl chloride and hydrolysis of the product thus obtained by the procedure of Example 17 provides the title compound.

In like manner the remaining amino compounds provided in Example 15 are sulfonylated with acid chlorides or acid bromides of formula $R_{17}SO_2Cl$(or Br) to provide compounds of the formula

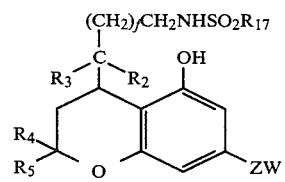

where f, $R_2$, $R_3$, $R_4$, $R_5$, Z and W are as defined in Example 15 and $R_{17}$ is methyl, ethyl, n-propyl, isopropyl, n-butyl, isoamyl, phenyl, p-tolyl or benzyl.

Esterification of the above 5-hydroxy compounds by the procedure of Example 18 affords the corresponding 5-OR$_1$ compounds where $R_1$ is as defined in Example 18.

EXAMPLE 20 dl-5-Hydroxy-4-carboxamidomethyl-2,2-dimethyl-7-(1,1-dimethylheptyl)-3,4-dihydro-2H-benzopyran A solution of 3.76 g (0.01 mole) dl-5-hydroxy-4-methoxycarbonylmethyl-2,2-dimethyl-7-(1,1-dimethylheptyl)-3,4-dihydro-2H-benzopyran (or its mixture with the corresponding lactone as obtained in Example 4) in 100 ml toluene is saturated with anhydrous ammonia at 10° C. The resulting mixture is placed in a sealed tube and heated at 95°-100° C. for 6 hours. The reaction mixture is cooled in ice, the tube opened and the mixture evaporated to dryness under reduced pressure to obtain the crude title compound which is purified by chromatography on silica gel.

When the above procedure is repeated but employing methylamine, ethylamine, isopropylamine, n-butylamine, 2-ethylbutylamine aniline or benzylamine in place of ammonia and/or one of the ester compounds provided in Example 14 as starting material in place of the above methyl ester, the following amides are obtained in like manner.

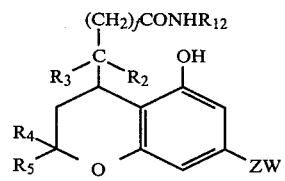

where $R_2$, $R_3$, $R_4$, $R_5$, Z and W are as defined in Examples 4 and 14, and f is zero or one and $R_{12}$ is methyl, ethyl, isopropyl, n-butyl, isobutyl, n-hexyl or benzyl.

Esterification of the 5-hydroxyamides, thus obtained, by the procedure of Example 18 affords the corresponding 5-$OR_1$-substituted compounds wherein $R_1$ is as defined in Example 18.

EXAMPLE 21 dl-5-Acetoxy-4-(N,N-dimethylaminocarboxamidomethyl)-2,2-dimethyl-7-(1,1-dimethylheptyl)-3,4-dihydro-2H-benzopyran To a solution of 2.01 g (5 mmole) dl-2-[5-acetoxy-2,2-dimethyl-7-(1,1-dimethylheptyl)-3,4-dihydro-2H-benzopyran-4-yl]acetic acid in 50 ml of chloroform is added dropwise with stirring 0.83 g (7 mmole) thionyl chloride in 10 ml of the same solvent. The resulting mixture is stirred at room temperature for one hour, evaporated to dryness at reduced pressure and the residue taken up in 35 ml ethyl ether. The ethereal solution of acid chloride is added dropwise to a cold solution of 1 gram of dimethylamine in 50 ml of ethyl ether. The resulting mixture is stirred for 30 minutes at 10° C., then filtered with suction. The filtrate is washed successively with dilute hydrochloric acid, water, sodium bicarbonate, water, brine and dried over magnesium sulfate. Evaporation of solvent affords the desired amide.

Hydrolysis of the 5-acetoxy amide thus obtained by procedure of Example 17 affords the corresponding 5-hydroxyamide in like manner.

When the remaining 5-acetoxy carboxylic acids provided in Example 14 are reacted with dimethylamine or other amine of the formula $R_{12}R_{13}NH$ by the above procedure, compounds of the following formula are obtained in like manner:

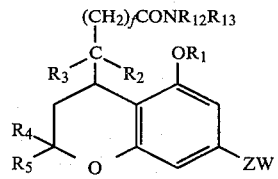

where f is zero or 1, $R_1$ is H or acetyl, $R_2$, $R_3$, $R_4$, $R_5$, Z and W are as defined in Example 14 and $R_{12}$ and $R_{13}$ are as defined below.

| $R_{12}$ | $R_{13}$ |
|---|---|
| $CH_3$ | $CH_3$ |
| $(C_2H_5)_2CHCH_2$ | $C_6H_5$ |
| $C_2H_5$ | $C_2H_5$ |
| $i-C_3H_7$ | $i-C_3H_7$ |
| $n-C_3H_7$ | $CH_3$ |
| $n-C_6H_{13}$ | $n-C_4H_9$ |
| $n-C_6H_{13}$ | $n-C_6H_{13}$ |
| $C_6H_5$ | H |
| $C_6H_5$ | $CH_3$ |
| $C_6H_5$ | $C_6H_5$ |
| $C_6H_5CH_2$ | $C_6H_5CH_2$ |
| $C_6H_5CH_2$ | $CH_3$ | or alternatively, $NR_{12}R_{13}$ taken together form:

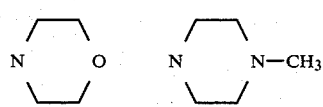

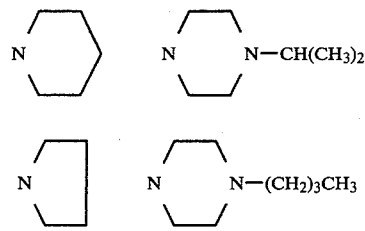

EXAMPLE 21A

Lithium aluminum hydride reduction of the amides provided in Examples 20 and 21 by the procedure of Example 15 provides the corresponding amine of the formula below in like manner:

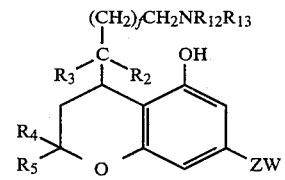

where f is zero or 1, $R_2$, $R_3$, $R_4$, $R_5$, $R_{12}$, $R_{13}$, Z and W are as defined in Examples 20 and 21.

EXAMPLE 22 dl-5-Hydroxy-4-formylmethyl-2,2-dimethyl-7-(1,1-dimethylheptyl)-3,4-dihydro-2H-benzopyran To a solution of 80 ml 0.5M disiamylborane (40 mmole) in tetrahydrofuran under dry nitrogen is added dropwise a solution of 7.78 g (0.02 mole) N,N-dimethyl-2-[5-hydroxy-2,2-dimethyl-7-(1,1-dimethylheptyl)-3,4-dihydro-2H-benzopyran-4-yl]acetamide in 50 ml tetrahydrofuran and the resulting mixture stirred at ambient temperature for six hours. A mixture of 50 ml each of glycerine and water is added and stirring continued until gas evolution is complete. The tetrahydrofuran is evaporated in vacuo, the residue extracted with ethyl ether, the extracts washed with water, dried ($MgSO_4$) and evaporated to provide the title compound. The product is purified by chromatography on silica gel.

In like manner compounds of the following formula are obtained from the corresponding N,N-dimethylamide obtained as described in Example 21:

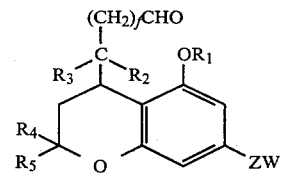

where f, $R_1$, $R_2$, $R_3$, $R_4$, $R_5$, Z and W are as defined in Example 21.

EXAMPLE 23

Treatment of the aldehydes provided in Example 22 with a molar excess of Grignard reagent by the procedures of Examples 8 and 8A provides secondary alcohols of the formula below.

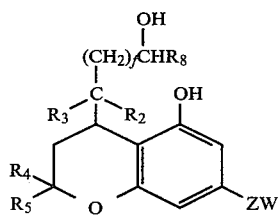

wherein f is zero or 1 and $R_2$, $R_3$, $R_4$, $R_5$, Z and W are as defined in Examples 5, 5A and 11 and $R_8$ is as defined in Example 8A.

Alternatively, the starting aldehyde is converted to its 5-acetoxy derivative prior to reaction with the Grignard reagent as described above.

EXAMPLE 24 dl-5-Hydroxy-2,2-dimethyl-7-(1,1-dimethylheptyl)-4-(2-oxopropyl)-3,4-dihydro-2H-benzopyran A solution of 5.0 g (0.02 mole) chromic anhydride in 5.0 ml water is added with stirring and ice cooling to 50 ml pyridine. To this is added at 10° C. 4.04 g (0.01 mole) dl-5-acetoxy-4-(2-hydroxypropyl)-2,2-dimethyl-7-(1,1-dimethylheptyl)-3,4-dihydro-2H-benzopyran and the resulting mixture stirred at room temperature for three hours. The reaction mixture is poured into water, made alkaline (pH 8.5-9.0) with sodium carbonate, stirred for 20 minutes then acidified with dilute hydrochloric acid and extracted with methylene chloride. The organic layer is washed with sodium bicarbonate solution, water, brine, dried over magnesium sulfate and the solvent evaporated, the last of the solvent being removed in vacuo. The residue is purified by column chromatography on silica gel to obtain the desired ketone.

In like manner the secondary alcohols provided in Examples 8A and 23 are converted to their 5-acetoxy derivatives by the procedure of Example 12 and oxidized by the above method to provide compounds of the formula

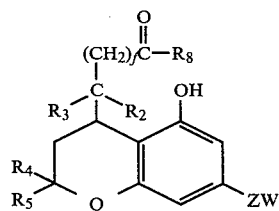

wherein f is zero or 1, $R_2$, $R_3$, $R_4$, $R_5$, $R_8$, Z and W are as defined in Example 23.

EXAMPLE 25

The 5-hydroxy ketones provided in Example 24 are converted to the corresponding 5-acetyl ketones by the procedure of Example 12, the products thus obtained are reacted with 3-4 moles of Grignard reagent, $R_9MgCl$ or $R_9MgBr$, by the procedure of Example 7 to provide 5-hydroxy-tertiary alcohols of the formula

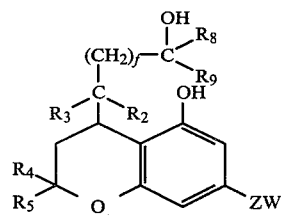

where $R_2$, $R_3$, $R_4$, $R_5$, Z and W are as defined in Examples 5A and 11, and f, $R_8$ and $R_9$ are as defined below.

| f | $R_8$ | $R_9$ |
|---|---|---|
| 0 | $CH_3$ | $C_2H_5$ |
| 0 | $C_2H_5$ | $C_6H_5CH_2$ |
| 0 | $n-C_4H_9$ | $CH_3$ |
| 0 | $CH_2CH(CH_3)_2$ | $C_6H_5$ |
| 0 | $n-C_4H_9$ | $n-C_4H_9$ |
| 1 | $CH_3$ | $C_6H_5$ |
| 1 | $n-C_3H_7$ | $i-C_4H_9$ |
| 1 | $C_2H_5$ | $C_6H_5$ |
| 1 | $n-C_4H_9$ | $C_6H_5CH_2$ |
| 1 | $C_6H_5CH_2$ | $C_6H_5$ |

EXAMPLE 26 dl-1-Benzyl-5-benzyloxy-2-methyl-7-(5-phenyl-2-pentyloxy)-4-oxo-1,2,3,4-tetrahydroquinoline To a mixture of 0.30 mole of potassium hydride and 500 ml freshly distilled N,N-dimethylformamide (DMF) cooled to 0° C. under nitrogen and anhydrous conditions, is added dropwise a solution of 33.9 g (0.10 mole) dl-5-hydroxy-2-methyl-7-(5-phenyl-2-pentyloxy)-4-oxo-1,2,3,4-tetrahydroquinoline in 350 ml of purified DMF at 0°-10° C. When the addition is complete, the mixture is allowed to warm to room temperature and stirred for one hour. The mixture is then cooled to 0° C., a solution of 18.81 g (0.11 mole) benzylbromide in 150 ml DMF is added slowly at 0°-10° C., the resulting mixture stirred at 5° C. for 30 minutes, then allowed to warm to room temperature and stirred overnight. The reaction is quenched by cautious addition of water, diluted with five liters ethyl ether, washed with water, brine, dried over anhydrous magnesium sulfate and the solvent evaporated in vacuo to obtain the crude product. It is purified, if desired, by column chromatography on silica gel.

EXAMPLE 27

Ethyl dl-2-[1-benzyl-5-benzyloxy-4-hydroxy-2-methyl-7-(5-phenyl-2-pentyloxy)-1,2,3,4-tetrahydroquinolin-4-yl]-2-methylpropionate

[VI, $Q_2=COOC_2H_5$, $R_2$, $R_3$; $R_4=CH_3$; $R_5=H$; $M=NCH_2C_6H_5$; $Y_1=CH_2C_6H_5$; $ZW=OCH(CH_3)(CH_2)_3C_6H_5$].

A. Under a nitrogen atmosphere at −78° C. to 45.5 ml (0.10 mole) of 2.2M n-butyl lithium in hexane is added 45 ml of dry tetrahydrofuran (THF). A solution of 18.08 g (0.10 mole) dicyclohexylamine in 45 ml THF is added dropwise, followed by 11.6 g (0.01 mole) ethyl 2-methylpropionate and the resulting mixture stirred at −78° C. for 30 minutes. A solution of 51.9 g (0.10 mole) dl-1-benzyl-5-benzyloxy-2-methyl-7-(5-phenyl-2-pentyloxy)-4-oxo-1,2,3,4-tetrahydroquinoline in 200 ml THF is slowly added and the resulting mixture is stirred five hours at −78° C. The reaction is quenched by addition of 8 ml acetic acid, allowed to warm to room temperature and 200 ml saturated sodium bicarbonate is added followed by 200 ml ethyl ether. The layers are separated, the ether layer washed with dilute hydrochloric acid, bicarbonate solution, water and dried (MgSO$_4$). Evaporation of solvent provides the crude product which is purified by silica gel chromatography.

B. A mixture of 4.2 g (0.065 mole) activated zinc, a small crystal of iodine and 50 ml of tetrahydrofuran is stirred and heated to reflux. A solution of 18.7 g (0.036 mole) dl-1-benzyl-5-benzyloxy-2-methyl-7-(5-phenyl-2-pentyloxy)-4-oxo-1,2,3,4-tetrahydroquinoline and 10.7 g (0.055 mole) ethyl 2-bromo-2-methylpropionate in 250 ml tetrahydrofuran is added slowly (about 30 minutes) and the resulting mixture refluxed for an additional hour. The tetrahydrofuran is removed by evaporation in vacuo, the residue partitioned between 0.1N hydrochloric acid and ethyl ether. The ether is discarded, the aqueous phase made alkaline with sodium hydroxide and extracted with ether. The ether extracts are washed with water, dried (MgSO$_4$) and evaporated to dryness to afford the desired product.

EXAMPLE 28

Ethyl dl-2-[5-hydroxy-2-methyl-7-(5-phenyl-2-pentyloxy)-1,2,3,4-tetrahydroquinolin-4-yl]-2-methylpropionate and its corresponding lactone

[IX, Q$_2$=COOC$_2$H$_5$, R$_2$, R$_3$; R$_4$=CH$_3$; R$_5$=H; M=NH; ZW=OCH(CH$_3$)(CH$_2$)$_3$C$_6$H$_5$]

A mixture of 6.35 g (0.01 mole) ethyl dl-2-[1-benzyl-5-benzyloxy-4-hydroxy-2-methyl-7-(5-phenyl-2-pentyloxy)-1,2,3,4-tetrahydroquinolin-4-yl]-2-methylpropionate, 250 ml ethanol and 2 g 5% palladium-on-carbon is hydrogenated at 50 psi (3.52 kg/cm$^2$) overnight. The resulting mixture is filtered and the filtrate evaporated in vacuo. The residue is taken up in ethyl ether, washed with water, the water wash extracted with ether and the combined ether layers washed with saturated sodium bicarbonate, brine, and dried over magnesium sulfate. Evaporation of solvent affords a mixture of the title compounds which is separated by crystallization and the products purified by chromatography on silica gel by the procedure of Example 4.

EXAMPLE 29

When 3,3-dimethyl-6-(5-phenyl-2-pentyloxy)-8-benzyloxy-1-tetralone (prepared as described in U.S. Pat. No. 4,188,495) is employed in place of the tetrahydroquinoline used as starting material in the procedures of Example 27A or 27B, ethyl dl-2-[8-benzyloxy-1-hydroxy-3,3-dimethyl-6-(5-phenyl-2-pentyloxy)-tetralin-1-yl]-2-methylpropionate is obtained in like manner. Hydrogenolysis of the product thus obtained by the method of Example 28 affords ethyl dl-2-[8-hydroxy-3,3-dimethyl-6-(5-phenyl-2-pentyloxy)-tetralin-1-yl]-2-methylpropionate in admixture with the corresponding lactone of the formula below.

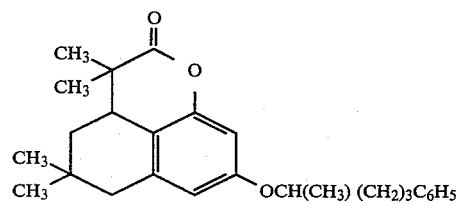

EXAMPLE 30

When the procedures of Examples 26–28 or Example 29 are repeated with the appropriate starting material in each case, products of the formulae below where M is NH or CH$_2$, respectively, are obtained in like manner.

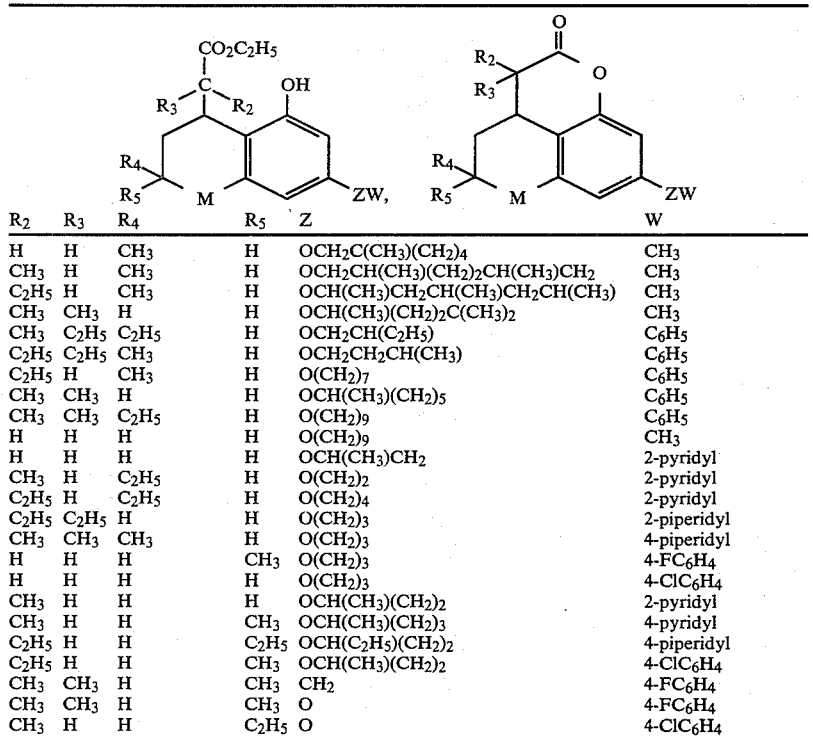

| R$_2$ | R$_3$ | R$_4$ | R$_5$ | Z | W |
|---|---|---|---|---|---|
| H | H | CH$_3$ | H | OCH$_2$C(CH$_3$)(CH$_2$)$_4$ | CH$_3$ |
| CH$_3$ | H | CH$_3$ | H | OCH$_2$CH(CH$_3$)(CH$_2$)$_2$CH(CH$_3$)CH$_2$ | CH$_3$ |
| C$_2$H$_5$ | H | CH$_3$ | H | OCH(CH$_3$)CH$_2$CH(CH$_3$)CH$_2$CH(CH$_3$) | CH$_3$ |
| CH$_3$ | CH$_3$ | H | H | OCH(CH$_3$)(CH$_2$)$_2$C(CH$_3$)$_2$ | CH$_3$ |
| CH$_3$ | C$_2$H$_5$ | C$_2$H$_5$ | H | OCH$_2$CH(C$_2$H$_5$) | C$_6$H$_5$ |
| C$_2$H$_5$ | C$_2$H$_5$ | CH$_3$ | H | OCH$_2$CH$_2$CH(CH$_3$) | C$_6$H$_5$ |
| C$_2$H$_5$ | H | CH$_3$ | H | O(CH$_2$)$_7$ | C$_6$H$_5$ |
| CH$_3$ | CH$_3$ | H | H | OCH(CH$_3$)(CH$_2$)$_5$ | C$_6$H$_5$ |
| CH$_3$ | CH$_3$ | C$_2$H$_5$ | H | O(CH$_2$)$_9$ | C$_6$H$_5$ |
| H | H | H | H | O(CH$_2$)$_9$ | CH$_3$ |
| H | H | H | H | OCH(CH$_3$)CH$_2$ | 2-pyridyl |
| CH$_3$ | H | C$_2$H$_5$ | H | O(CH$_2$)$_2$ | 2-pyridyl |
| C$_2$H$_5$ | H | C$_2$H$_5$ | H | O(CH$_2$)$_4$ | 2-pyridyl |
| C$_2$H$_5$ | C$_2$H$_5$ | H | H | O(CH$_2$)$_3$ | 2-piperidyl |
| CH$_3$ | CH$_3$ | CH$_3$ | H | O(CH$_2$)$_3$ | 4-piperidyl |
| H | H | H | CH$_3$ | O(CH$_2$)$_3$ | 4-FC$_6$H$_4$ |
| H | H | H | H | O(CH$_2$)$_3$ | 4-ClC$_6$H$_4$ |
| CH$_3$ | H | H | H | OCH(CH$_3$)(CH$_2$)$_2$ | 2-pyridyl |
| CH$_3$ | H | H | CH$_3$ | OCH(CH$_3$)(CH$_2$)$_3$ | 4-pyridyl |
| C$_2$H$_5$ | H | H | C$_2$H$_5$ | OCH(C$_2$H$_5$)(CH$_2$)$_2$ | 4-piperidyl |
| C$_2$H$_5$ | H | H | CH$_3$ | OCH(CH$_3$)(CH$_2$)$_2$ | 4-ClC$_6$H$_4$ |
| CH$_3$ | CH$_3$ | H | CH$_3$ | CH$_2$ | 4-FC$_6$H$_4$ |
| CH$_3$ | CH$_3$ | H | CH$_3$ | O | 4-FC$_6$H$_4$ |
| CH$_3$ | H | H | C$_2$H$_5$ | O | 4-ClC$_6$H$_4$ |

-continued

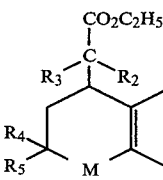

| R2 | R3 | R4 | R5 | Z | W |
|---|---|---|---|---|---|
| CH3 | H | H | CH3 | O | C3H5 |
| C2H5 | C2H5 | H | CH3 | O | C4H7 |
| C2H5 | C2H5 | H | C2H5 | O | C5H9 |
| H | H | H | CH3 | O | C6H11 |
| H | H | H | CH3 | O | C7H13 |
| H | H | H | CH3 | O | 2-(C6H5)C3H4 |
| H | H | H | CH3 | O | 1-(C6H5)C4H6 |
| H | H | H | CH3 | O | 2-(C6H5)C5H8 |
| CH3 | H | H | CH3 | O | 4-(C6H5)C6H10 |
| CH3 | H | H | CH3 | O | 2-(C6H5)C6H10 |
| CH3 | H | H | CH3 | O | 3-(C6H5)C7H12 |
| CH3 | H | H | CH3 | OCH2— | CH3 |
| CH3 | H | H | CH3 | O(CH2)3— | CH3 |
| CH3 | H | H | CH3 | O(CH2)6— | CH3 |
| CH3 | H | H | CH3 | O(CH2)9— | CH3 |
| CH3 | H | H | C2H5 | O(CH2)3— | CH3 |
| CH3 | H | H | CH3 | OC(CH3)2(CH2)5— | CH3 |
| CH3 | H | H | CH3 | OCH(CH3)CH(CH3)(CH2)4— | CH3 |
| CH3 | H | CH3 | CH3 | O(CH2)4— | C6H5 |
| CH3 | H | CH3 | CH3 | OC(CH3)2(CH2)6— | H |
| CH3 | H | CH3 | CH3 | O | C6H5 |
| H | H | H | H | O(CH2)9 | H |
| H | H | CH2C6H5 | CH3 | OCH(CH3)(CH2)3 | 3-pyridyl |
| CH3 | CH3 | n-C4H9 | CH3 | O | C6H5 |
| CH3 | H | (CH2)3C6H5 | CH3 | O | 4-FC6H4 |
| CH3 | H | CH3 | CH3 | OC(CH3)2(CH2)5 | CH3 |
| CH3 | CH3 | H | H | CH(CH3)(CH2)3 | C6H5 |
| CH3 | CH3 | CH3 | H | CH(CH3)(CH2)4 | C6H5 |
| H | H | H | H | (CH2)3 | C6H5 |
| H | H | C2H5 | H | (CH2)4 | C6H5 |
| H | H | CH3 | H | CH(C2H5)(CH2)3 | C6H5 |
| H | H | H | H | C(CH3)2 | C6H5 |
| H | H | CH3 | H | C(CH3)2(CH2)3 | C6H5 |
| H | H | CH3 | H | (CH2)8 | C6H5 |
| H | H | H | H | CH(CH3)(CH2)7 | C6H5 |
| CH3 | CH3 | H | H | CH2 | C6H5 |
| CH3 | CH3 | H | H | CH(CH3)(CH2)3 | 4-FC6H4 |
| C2H5 | C2H5 | C2H5 | H | CH(CH3)CH2 | 4-FC6H4 |
| C2H5 | C2H5 | C2H5 | H | CH(CH3)(CH2)2 | 4-ClC6H4 |
| CH3 | CH3 | H | H | (CH2)3 | C5H9 |
| CH3 | CH3 | CH3 | CH3 | CH(CH3)(CH2)3 | C6H5 |
| H | H | H | H | CH(CH3)(CH2)3 | C5H9 |
| H | H | H | H | CH(CH3)CH2 | C3H5 |
| H | H | H | H | OH(CH3)CH(CH3) | C6H11 |
| CH3 | H | CH3 | H | CH(CH3)(CH2)5 | C6H11 |
| CH3 | CH3 | H | H | (CH2)8 | C6H11 |
| CH3 | CH3 | H | H | (CH2)4 | 2-pyridyl |
| CH3 | H | CH3 | H | CH2CH(CH3)CH2 | 4-pyridyl |
| C2H5 | H | C2H5 | H | CH(CH3)(CH2)2 | 3-pyridyl |
| C2H5 | H | CH3 | H | CH(CH3)CH(C2H5)CH2 | 4-pyridyl |
| H | H | H | H | CH(CH3)(CH2)2 | 4-piperidyl |
| CH3 | H | CH3 | H | CH(C2H5)(CH2)2 | 2-piperidyl |
| CH3 | H | CH3 | H | CH(CH3)(CH2)2 | C7H13 |
| H | H | H | H | CH(CH3)(CH2)2 | C7H13 |
| CH3 | H | CH3 | H | CH(CH3)CH2O(CH2)2 | C6H5 |
| H | H | H | H | (CH2)4 | CH3 |
| H | H | CH3 | H | CH(CH3)CH(CH3)(C2H5) | H |
| H | H | H | H | CH2 | H |
| H | H | CH3 | H | CH2 | CH3 |
| H | H | H | H | (CH2)6 | CH3 |
| CH3 | H | CH3 | H | (CH2)3 | H |
| CH3 | CH3 | H | H | CH(CH3) | C6H11 |
| C2H5 | C2H5 | C2H5 | H | CH(CH3)(CH2)4 | CH3 |
| H | H | H | H | (CH2)3O | C6H5 |
| H | H | CH3 | H | (CH2)3O | 4-FC6H4 |
| CH3 | CH3 | H | H | (CH2)3O | CH3 |
| H | H | CH3 | H | (CH2)3O | 4-(4-FC6H4)C6H10 |
| H | H | C2H5 | H | (CH2)3O(CH2)2 | 4-ClC6H4 |
| H | H | H | H | (CH2)3O(CH2)2 | C6H5 |
| H | H | CH3 | H | (CH2)3OCH(CH3) | 4-piperidyl |
| CH3 | H | CH3 | H | (CH2)3OCH(CH3)(CH2)2 | C6H5 |

-continued

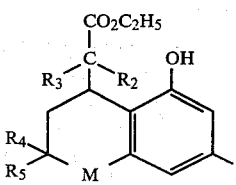

| R2 | R3 | R4 | R5 | Z | W |
|---|---|---|---|---|---|
| H | H | H | H | $(CH_2)_3OCH(CH_3)(CH_2)_2$ | $CH_3$ |
| H | H | H | H | $CH(CH_3)(CH_2)_2O$ | $C_6H_5$ |
| H | H | $CH_3$ | H | $CH(CH_3)(CH_2)_2OCH_2$ | $CH_3$ |
| $CH_3$ | H | $CH_3$ | H | $CH(CH_3)(CH_2)_2O(CH_2)_4$ | $C_6H_5$ |
| $CH_3$ | H | $CH_3$ | H | $CH(CH_3)(CH_2)_2OCH(CH_3)$ | $C_7H_{13}$ |
| H | H | H | H | $CH(CH_3)(CH_2)_2OCH_2CH(C_2H_5)$ | $CH_3$ |
| H | H | $CH_3$ | H | $(CH_2)_4O$ | $C_6H_5$ |
| $C_2H_5$ | H | $C_2H_5$ | H | $(CH_2)_4O(CH_2)_5$ | 4-pyridyl |
| $C_2H_5$ | H | $C_2H_5$ | H | $(CH_2)_4OCH_2$ | $4-FC_6H_4$ |
| H | H | H | H | $CH(CH_3)(CH_2)_3O$ | $2-(4-FC_6H_4)C_5H_8$ |
| H | H | $CH_3$ | H | $CH(CH_3)(CH_2)_3O(CH_2)_2$ | $C_6H_5$ |
| $CH_3$ | H | H | H | $CH(C_2H_5)(CH_2)_2O(CH_2)_2CH(CH_3)$ | $C_7H_{13}$ |
| H | H | $CH_3$ | H | $CH(CH_3)OCH_2$ | $C_5H_9$ |
| H | H | $CH_3$ | H | $CH(C_2H_5)(CH_2)_2O$ | $C_3H_9$ |
| H | H | H | H | $CH(C_2H_5)(CH_2)_2O$ | $2-(4-FC_6H_4)C_7H_{12}$ |
| H | H | H | H | $CH(CH_3)CH_2O(CH_2)_6$ | $CH_3$ |
| H | H | $CH_3$ | H | $CH(CH_3)CH_2O(CH_2)_6$ | $C_6H_5$ |
| H | H | H | H | $CH(CH_3)CH_2OCH_2(CH_3)CH_2$ | $C_6H_5$ |
| H | H | $CH_3$ | H | $CH(CH_3)CH_2OCH_2$ | $4-FC_6H_4$ |
| H | H | $CH_3$ | H | $CH(CH_3)CH_2O(CH_2)_2$ | 4-pyridyl |
| H | H | H | H | $CH(CH_3)CH_2OCH(CH_3)$ | $CH_3$ |
| $C_2H_5$ | $CH_3$ | $C_2H_5$ | H | $CH_2CH(CH_3)OCH_2$ | $CH_3$ |
| $C_2H_5$ | $CH_3$ | $CH_3$ | H | $CH_2CH(CH_3)O(CH_2)_6$ | $CH_3$ |
| $CH_3$ | $CH_3$ | $CH_3$ | H | $C(CH_3)_2(CH_2)_6$ | H |
| $CH_3$ | $CH_3$ | $C_2H_5$ | H | $C(CH_3)_2(CH_2)_6$ | H |
| $CH_3$ | $CH_3$ | $C_2H_5$ | $C_2H_5$ | $CH(CH_3)(CH_2)_3$ | $C_6H_5$ |
| $CH_3$ | $CH_3$ | $C_6H_5CH_2$ | H | $(CH_2)_3$ | $C_6H_5$ |
| H | H | $n-C_6H_{13}$ | H | $(CH_2)_4$ | $C_6H_5$ |
| $CH_3$ | $C_2H_5$ | $CH_3$ | $C_2H_5$ | $(CH_2)_4$ | $C_6H_5$ |
| $CH_3$ | $C_2H_5$ | $C_6H_5(CH_2)_4$ | H | $(CH_2)_2CH(C_2H_5)$ | $C_6H_5$ |
| $CH_3$ | $CH_3$ | $CH_3$ | $CH_3$ | $(CH_2)_8$ | $C_6H_5$ |
| $CH_3$ | $CH_3$ | $CH_3$ | $CH_3$ | $CH(CH_3)(CH_2)_7$ | $C_6H_5$ |
| H | H | $n-C_4H_9$ | H | $CH_2$ | $C_6H_5$ |
| $CH_3$ | H | $C_6H_5(CH_2)_2$ | H | $CH(CH_3)(CH_2)_2CH(CH_3)$ | $C_6H_5$ |
| H | H | $CH_3$ | H | $CH_2$ | $C_6H_5$ |
| $C_2H_5$ | $C_2H_5$ | $C_6H_5CH_2$ | H | $(CH_2)_3$ | $C_5H_9$ |
| H | H | $C_6H_5(CH_2)_3$ | H | $CH(CH_3)(CH_2)_5$ | $C_6H_{11}$ |
| $CH_3$ | H | $CH_3$ | $CH_3$ | $(CH_2)_9$ | $C_6H_{11}$ |
| H | H | $i-C_3H_7$ | H | $CH(CH_3)(CH_2)_2$ | 4-piperidyl |
| $C_2H_5$ | $C_2H_5$ | $C_2H_5$ | $C_2H_5$ | $C(CH_3)_2(CH_2)_6$ | H |

EXAMPLE 30A

When the procedure of Example 27 is repeated but starting with a corresponding 4-oxoquinoline compound in which the $N-CH_2C_6H_5$ group is replaced with $NR_6$, where $R_6$ is as defined below, and the products thus obtained hydrogenated by the procedure of Example 28, compounds of the following formulae are obtained in like manner. The requisite starting materials are provided in U.S. Pat. No. 4,260,764.

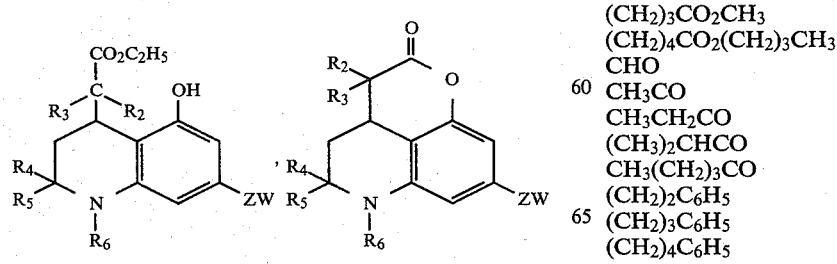

where $R_2$–$R_5$, Z and W are as defined in Example 30.

$R_6$
$CH_3$
$C_2H_5$
$n-C_4H_9$
$(CH_3)_2CH(CH_2)_2$
$n-C_6H_{13}$
$(CH_3)_2CH$
$CH_2CO_2CH_3$
$CH_2CO_2CH_2CH(CH_3)_2$
$CO_2C_2H_5$
$CH_2CH_2CO_2C_2H_5$
$(CH_2)_3CO_2CH_3$
$(CH_2)_4CO_2(CH_2)_3CH_3$
$CHO$
$CH_3CO$
$CH_3CH_2CO$
$(CH_3)_2CHCO$
$CH_3(CH_2)_3CO$
$(CH_2)_2C_6H_5$
$(CH_2)_3C_6H_5$
$(CH_2)_4C_6H_5$ $C_6H_5CO$
$C_6H_5(CH_2)_2CO$
$C_6H_5(CH_2)_3CO$
$CO_2CH_3$
$CO_2(CH_2)_3CH_3$
$(CH_3)_2CHCH_2$
$CH_3CH_2CH(CH_3)(CH_2)_2$
$CH_3(CH_2)_2CO$

EXAMPLE 31 dl-5-Hydroxy-4-(3-hydroxy-2-methyl-2-propyl)-2-methyl-7-(5-phenyl-2-pentyloxy)-1,2,3,4-tetrahydroquinoline To a mixture of 418 mg (0.011 mole) lithium aluminum hydride and 200 ml dry ethyl ether under nitrogen, is added dropwise with stirring at 5°–10° C., a solution of 4.39 g (0.01 mole) ethyl dl-2-[5-hydroxy-2-methyl-7-(5-phenyl-2-pentyloxy)-1,2,3,4-tetrahydroquinoline-4-yl]-2-methylpropionate in 50 ml dry ethyl ether. The mixture is then allowed to warm to room temperature and stirred overnight. The reaction is quenched by cautious addition of ethyl acetate, the mixture washed with water, brine and dried over anhydrous magnesium sulfate. Evaporation of solvent affords the crude product which may be purified, if desired, by column chromatography on silica gel.

When the corresponding lactone: dl-3,3,5-trimethyl-8-(5-phenyl-2-pentyloxy)-2,3,3a,4,5,6-hexahydropyrano[4,3,2-de]quinoline or its mixtures with the above ester are employed as starting material in the above procedure, the title compound is obtained in like manner.

In a similar manner the compounds provided in Examples 29 and 30 are reduced by the above method to obtain compounds of the formula

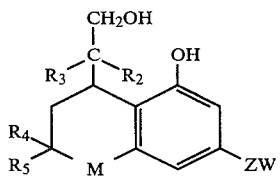

where $R_2$, $R_3$, $R_4$, $R_5$, M, Z and W are as defined in Examples 29 and 30.

Similarly, the compounds provided in Example 30A wherein $R_6$ is alkyl or aralkyl as defined therein provide the corresponding compounds of the above formula wherein M is $NR_6$ and $R_6$ is said alkyl or aralkyl.

EXAMPLE 32

Reduction of the lactones prepared in Examples 28–30 and by the procedure of Example 6 provides the corresponding lactols of the formula below

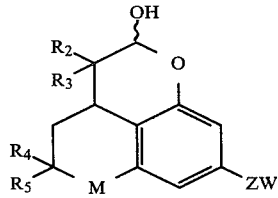

where $R_2$, $R_3$, $R_4$, $R_5$, M, Z and W are as defined for the lactone starting materials. Similarly, the lactones provided in Example 30A wherein $R_6$ is alkyl or aralkyl afford the corresponding lactols of the above formula where M is $NR_6$ and $R_6$ is said alkyl or aralkyl.

EXAMPLE 33

Reactions of the lactones or esters provided in Examples 28–30, or those of Examples 30A wherein $R_6$ is alkyl or aralkyl, with a Grignard reagent $R_8MgX$ where X is Cl, Br or I, by the procedure of Example 7 affords the corresponding tertiary alcohols of the formula

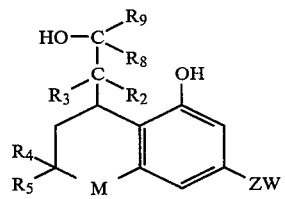

where $R_2$, $R_3$, $R_4$, $R_5$, M, Z and W are as defined in Examples 28–31; $R_8$ and $R_9$ are the same and are as defined in Example 7A.

EXAMPLE 34

Treatment of the lactols provided in Example 32 with Grignard reagents, $R_8MgX$ (X=Cl, Br or I) by the procedure of Examples 8 and 8A affords the corresponding secondary alcohols of the formula

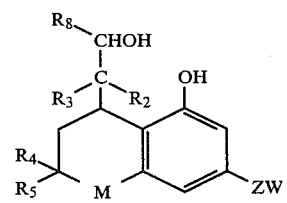

where $R_2$, $R_3$, $R_4$, $R_5$, M, Z and W are as defined in Example 32 and $R_8$ is as defined in Example 8A.

EXAMPLE 35

The following compounds are obtained by employing the lactols provided in Example 32 in the procedures of Examples 9 and 9A

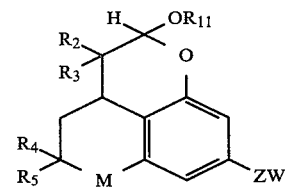

where $R_2$, $R_3$, $R_4$, $R_5$, M, Z and W are as defined in Example 32 and $R_{11}$ is as defined in Example 9A.

EXAMPLE 36

By employing the appropriate 1-benzyl-5-benzyloxy-2,2-($R_4$, $R_5$)-7-(ZW)-4-oxo-tetrahydroquinoline or 8-benzyloxy-3,3-($R_4$, $R_5$)-6-(ZW)-1-tetralone as starting material and either a lithio derivative, $LiC(R_2R_3)CN$, in the procedure of Example 27A, or a bromoacetonitrile, $BrC(R_2R_3)CN$ in the Reformatsky reaction as described in Example 27B and reduction of the resulting product by the procedure of Example 28, the following nitriles are obtained

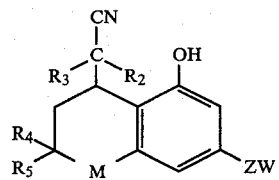

where $R_2$, $R_3$, $R_4$, $R_5$, M, Z and W are as defined in Examples 28–30.

EXAMPLE 37

The dihydroxy compounds obtained in Example 31 are monoacetylated by the method of Example 12, the resulting acetoxy compounds are then reacted by the procedure of Example 13 to provide the corresponding nitriles of the formula below

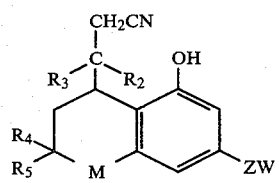

where $R_2$, $R_3$, $R_4$, $R_5$, M, Z and W are as defined in Examples 28–30.

EXAMPLE 38

The cyano compounds provided in Examples 36 and 37 are hydrolyzed by the method of Example 14 to provide carboxylic acids of the formula below where $R_7$ is hydrogen

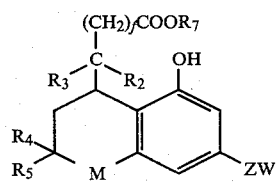

f is 0 or 1 and $R_2$–$R_5$, M, Z and W are as defined in Examples 28–30. The acids in turn are esterified to provide the above compounds where $R_7$ is $C_1$–$C_4$ alkyl or benzyl also as described in Example 14.

EXAMPLE 39

Lithium aluminum hydride reduction of the esters provided in Example 38 by the method of Example 5 affords primary alcohols of the formula

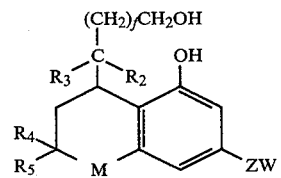

where f, $R_2$–$R_5$, M, Z and W are as defined in Example 38.

EXAMPLE 40

Lithium aluminum hydride reduction of the nitriles provided in Examples 36 and 37 by the method of Example 15 provides primary amines of the formula below

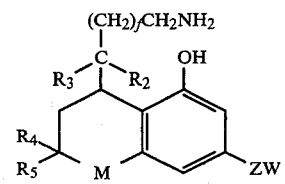

where f, $R_2$–$R_5$, M, Z and W are as defined in Example 38.

EXAMPLE 41

The primary amines provided in Example 40 are acylated by the method of Example 16 to provide the corresponding amino esters of the formula below by the procedure of Example 16.

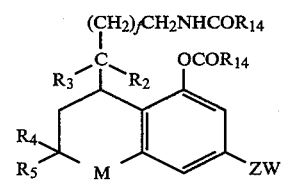

where $R_{14}$ is as defined in Example 16 and f, $R_2$–$R_5$, M, Z and W are as defined in Example 38.

EXAMPLE 42

In similar manner compounds of the formula below are obtained from the above amido esters by the procedure of Example 17.

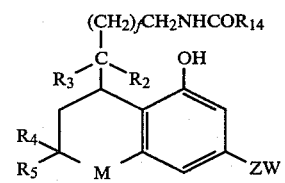

EXAMPLE 43

When the procedure of Example 18 is carried out starting with the hydroxy amides provided in Example 42, the following compounds are obtained in like manner.

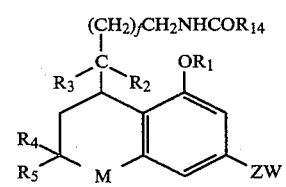

where $R_1$ is as defined in Example 18 and f, $R_2$–$R_5$, $R_{14}$, M, Z and W are as defined in Example 41.

EXAMPLE 44

Sulfonylation of the primary amines provided in Example 40 by the method of Example, 19 provides compounds of the formula below

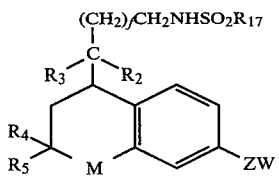

where $R_{17}$ is as defined in Example 19 and f, $R_2$–$R_5$, M, Z and W are as defined in Example 38.

EXAMPLE 45

Reaction of the esters or lactones provided in Examples 28–30 with ammonia or an amine of formula $R_{12}NH_2$ by the procedure of Example 20 similarly provides compounds of the formula

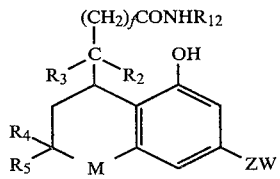

where $R_{12}$ is as defined in Example 20 and f, $R_2$–$R_5$, M, Z and W are as defined in Example 38.

EXAMPLE 46

Acetylation of the hydroxy carboxylic acids provided in Example 38 by the procedure of Example 12, conversion of the resulting acetoxy carboxylic acid to the acid chloride and subsequent reaction with amine of the formula $R_{12}R_{13}NH$ by the method of Example 21 affords compounds of the formula

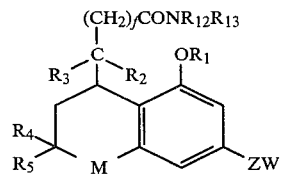

where $R_1$, $R_{12}$ and $R_{13}$ are as defined in Example 21 and f, $R_2$–$R_5$, M, Z and W are as defined in Example 38.

EXAMPLE 47

Reaction of the N,N-dimethylamides provided in Example 46 with the disiamylborane in tetrahydrofuran under the anhydrous conditions described in Example 22 provides the corresponding aldehydes of the formula

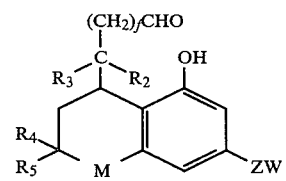

where f, $R_2$–$R_5$, M, Z and W are as defined in Example 38.

EXAMPLE 48

Treatment of the above aldehydes with a molar excess of Grignard reagent, $R_8MgBr$ or $R_8MgCl$, by the procedures of Examples 8 and 8A provides secondary alcohols of the formula

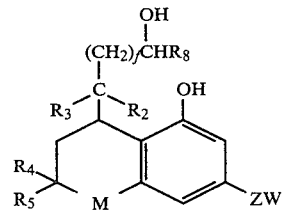

where $R_8$ is as defined in Example 8A and f, $R_2$–$R_5$, M, Z and W are as defined in Example 38.

EXAMPLE 49

Oxidation of the secondary alcohols obtained in Example 48 with chromic anhydride in pyridine by the method of Example 24 provides the corresponding ketones of the formula

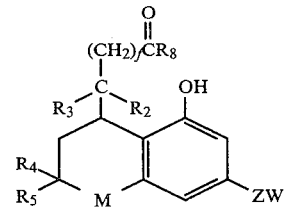

EXAMPLE 50

The ketones provided above are reacted with molar excess of Grignard reagent by the procedure of Example 25 to provide tertiary alcohols of the formula

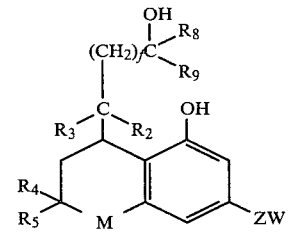

where $R_8$ and $R_9$ are as defined in Example 25 and f, $R_2$–$R_5$, M, Z and W are as defined in Example 38.

EXAMPLE 51 dl-3-(2-Carbonyloxymethyl)ethyl-5-hydroxy-2,2-dimethyl-7-(5-phenyl-2-pentyloxy)-3,4-dihydro-2H-benzopyran-4-one To 30.1 g (78 mmole) dl-5-hydroxy-3-hydroxymethylene-2,2-dimethyl-7-(5-phenyl-2-pentyloxy)-3,4-dihydro-2H-benzopyran-4-one was added 84 ml triethylamine and 210 ml (2.34 mole) methyl acrylate and the mixture was stirred at room temperature for two days. Additional methyl acrylate (210 ml) and triethylamine (30 ml) was added and stirring continued for two more days. The reaction mixture was concentrated in vacuo to obtain a residual oil which was chromatographed on a silica gel column taking 50 ml fractions. Twenty fractions were collected eluting with 4:1 (v/v) methylene chloride/hexane, elution was continued with methylene chloride for an additional 27 fractions, 9:1 (v/v) methylene chloride ethyl acetate for 11 fractions and ethyl acetate for 7 fractions. Fractions 18–50, containing the 3-formyl derivative of the desired product as determined by mass spectroscopy, were combined and evaporated to provide 23.0 g as an oil.

Fractions 51–58 were combined and evaporated to obtain 8.44 g of impure 3-formyl derivative which was purified further by chromatography on silica gel eluting with 7:3 (v/v) methylene chloride hexane (16 fractions), chloroform (20 fractions) and ethyl acetate (3 fractions). Fractions 10–25 were combined and evaporated to provide an additional 6.75 g of 3-formyl derivative.

The combined 3-formyl derivatives, 29.75 g, were dissolved in 200 ml of methanol, 3 ml of triethylamine was added and the mixture stirred for one hour at room temperature. The solution was evaporated to dryness, taken up in ethyl ether, washed with water, brine, dried over anhydrous magnesium sulfate and the ether evaporated to provide 27.8 g of the desired deformylated product. $^1$H-NMR(CDCl$_3$)ppm(delta): 1.4 (d, 3H), 3.55 (s, 3H), 4.3 (m, broad, 1H), 5.85 (m, 2H), 7.08 (s, 5H), 11.2 (s, broad, 1H).

EXAMPLE 52

A. Repeating the procedure of Example 51 but employing either an analogous tetralone or N-protected tetrahydroquinoline, specifically 2-hydroxymethylene-3,3-dimethyl-6-(5-phenyl-2-pentyloxy)-8-hydroxy-1-tetralone or 1-formyl-5-hydroxy-3-hydroxymethylene-2-methyl-7-(2-heptyloxy)-4-oxo-1,2,3,4-tetrahydroquinoline, provides analogous compounds. The former starting material, which is provided in U.S. Pat. No. 4,188,495, affords 2-(2-carbonyloxymethyl)ethyl-3,3-dimethyl-6-(5-phenyl-2-pentyloxy)-8-hydroxy-1-tetralone. The latter starting material, which is provided in U.S. Pat. No. 4,228,169, affords 3-(2-carbonyloxymethyl)-1-formyl-5-hydroxy-2-methyl-7-(2-heptyloxy)-4-oxo-1,2,3,4-tetrahydroquinoline.

In like manner compounds of the formula below are obtained from the appropriate starting materials.

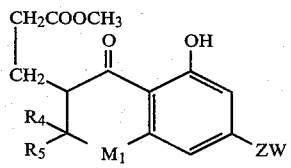

where R$_4$, R$_5$, Z and W are as defined in Examples 1A, 1B, and 1C and M$_1$ is O, CH$_2$ or NCHO.

B. Employing the procedure of Example 51 with the appropriate starting alpha-hydroxymethylene-3,4-dihydrobenzopyran-4-one, alpha-hydroxy-methylene-1-tetralone or alpha-hydroxymethylene-1-formyl-4-oxo-1,2,3,4-tetrahydroquinoline and the appropriate acrylate, R$_2$R$_3$C=CH-Q, the following compounds are obtained

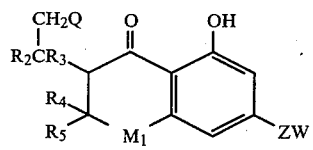

where R$_4$, R$_5$, Z and W are as defined in Examples 1A, 1B and 1C, M$_1$ is O, CH$_2$ or NCHO and R$_2$, R$_3$ and Q are as defined below.

| R$_2$ | R$_3$ | Q |
|---|---|---|
| H | H | CN |
| CH$_3$ | H | COOC$_2$H$_5$ |
| C$_2$H$_5$ | H | COOCH$_2$CH$_2$CH$_3$ |
| CH$_3$ | CH$_3$ | COO(CH$_2$)$_3$CH$_3$ |
| C$_2$H$_5$ | C$_2$H$_5$ | COOCH$_3$ |

EXAMPLE 53 dl-3-[5-Hydroxy-2,2-dimethyl-7-(5-phenyl-2-pentyloxy)-3,4-dihydro-2H-benzopyran-4-one-3yl]propionic acid To a solution of 27.8 g (0.057 mole) dl-3-(2-carbonyloxymethyl)ethyl-5-hydroxy-2,2-dimethyl-7-(5-phenyl-2-pentyloxy)-3,4-dihydro-2H-benzopyran-4-one in 200 ml of methanol was added 50 ml of 5N sodium hydroxide solution and the mixture stirred at room temperature for 30 minutes. The mixture was evaporated, the residue taken up in water, washed with ether and the aqueous phase acidified (pH 4) with 6N hydrochloric acid. The product was extracted with ether, the extracts dried (MgSO$_4$) and evaporated to provide 26.1 g of crude product. The crude material was purified by chromatography on silica gel (230 g) eluting with 1:1 (v/v) hexane/ethyl ether to afford 23.9 g of purified product.

$^1$H-NMR(CDCl$_3$)ppm(delta): 4.40 (m, 1H), 5.95 (m, 2H), 7.20 (s, 5H), 10.10 (s, 1H), 11.80 (s, 1H). Mass spectrum (m/e): 426 (M+), 280 (M-146).

EXAMPLE 54

Employing the carboxylate esters provided in Example 52 as starting material in the procedure of Example 53, the compounds of the formula below are obtained in like manner.

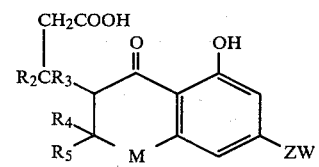

where R$_2$–R$_5$, Z and W are as defined in Example 52 and M is O, CH$_2$ or NH.

For starting materials wherein M is NCHO the methanolic sodium hydroxide reaction mixture is heated at reflux for six hours, the solvent evaporated, the residue taken up in water, washed with ether and the aqueous phase adjusted to the isoelectric point (pH 4–6) with hydrochloric acid and the precipitated product collected by filtration. If desired, it was purified by recrystallization or chromatography.

EXAMPLE 55 dl-10-Acetoxy-5,5-dimethyl-8-(5-phenyl-2-pentyloxy)-3,4-dihydro-pyrano[3,2-c]-5H-benzopyran-2-one (enol lactone)

A mixture of 1.55 g (3.3 mmole) dl-3-[5-hydroxy-2,2-dimethyl-7-(5-phenyl-2-pentyloxy)-3,4-dihydro-2H-benzopyran-4-one-3-yl]propionic acid, 270 mg (3.3 mmole) sodium acetate and 20 ml acetic anhydride was heated at 100° C. under a nitrogen atmosphere for 36 hours. The mixture was concentrated to dryness in vacuo, the residue triturated with ethyl ether and filtered. The filtrate was washed with water (2×1 ml), brine (2×1 ml), dried over anhydrous magnesium sulfate and evaporated to dryness to obtain 1.6 g of crude product contaminated with acetic acid; a one gram portion was purified by chromatography on 75 g of florisil (activated magnesium silicate) eluting with 1:1 (v/v) hexane/ethyl ether to afford 1.0 g of the desired enol lactone.

$^1$H-NMR(CDCl$_3$)ppm(delta): 1.30 (d, 3H), 1.50 (s, 6H), 2.30 (s, 3H), 6.20 (m, 2H), 7.20 (s, 5H). Mass spectrum (m/e): 450 (M+), 435 (M-15).

EXAMPLE 56

Employing the compounds provided in Example 54 in the procedure of Example 55, the following compounds are similarly obtained.

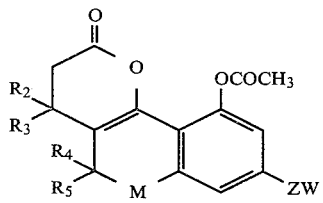

where R$_2$–R$_5$, M, Z and W are as defined in Example 54.

EXAMPLE 57 dl-3-[5-Acetoxy-2,2-dimethyl-7-(5-phenyl-2-pentyloxy)3,4-dihydro-2H-benzopyran-3-yl]propionic acid A mixture of 3.622 g 10-acetoxy-5,5-dimethyl-8-(5-phenyl-2-pentyloxy)-3,4-dihydropyrano[3,2-c]-5H-benzopyran-2-one, 3.0 ml of acetic acid and 3.5 g 10% Pd/C catalyst was hydrogenated at atmospheric pressure overnight. The catalyst was removed by filtration, washed with ethyl acetate and the filtrate evaporated in vacuo. To the residue was added 25 ml portions of dioxane and this evaporated to remove residual acetic acid as the azeotrope. The resulting residual oil, 3.8 g, was purified by chromatography on a silica gel column eluting with methylene chloride, taking 25 ml fractions. After 35 fractions were collected, elution with ethyl ether was employed for 5 fractions. The product containing fractions (#4–30) were combined and evaporated to dryness to obtain 843 mg of product.

$^1$H-NMR(CDCl$_3$)ppm(delta): 2.25 (s, 3H), 4.20 (m, 1H), 6.20 (broad s, 2H), 7.20 (s, 5H), 8.60 (s, 1H). Mass spectrum (m/e): 454 (M+).

EXAMPLE 58

In like manner the lactones provided in Example 56 are hydrogenated by the procedure of Example 57 and purified, if desired, by column chromatography to obtain compounds of the formula

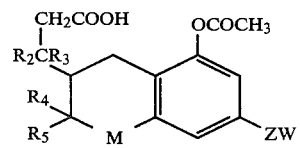

where R$_2$–R$_5$, M, Z and W are as defined in Example 54.

EXAMPLE 59

Methyl dl-3-[5-acetoxy-2,2-dimethyl-7-(5-phenyl-2-pentyloxy)-3,4-dihydro-2H-benzopyran-3-yl]propionate To a solution of 130 mg of dl-[5-acetoxy-2,2-dimethyl-7-(5-phenyl-2-pentyloxy)-3,4-dihydro-2H-benzopyran-3-yl]propionic acid in 10 ml of ethyl ether was added a freshly prepared solution of diazomethane in ether until the color of the reaction mixture remained yellow. The mixture was then stirred for a few minutes, quenched with acetic acid and evaporated to an oil. The oil was purified by column chromatography on silica gel eluting with methylene chloride for 17 fractions (25 ml per fraction) then with 9:1 methylene chloride/ethyl acetate for 6 fractions. The product fractions (#4–18) were combined and evaporated to provide 137 mg of the desired methyl ester. $^1$H-NMR(CDCl$_3$)ppm(delta): 2.20 (s, 3H), 3.70 (s, 3H), 4.20 (m, 1H), 6.22 (broad s, 2H), 7.25 (s, 5H). Mass spectrum (m/e): 468 (M+).

Similarly, the carboxylic acids provided in Example 58 are converted to methyl esters of the formula below

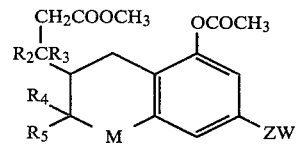

where R$_2$–R$_5$, M, Z and W are as defined in Example 54.

EXAMPLE 60 dl-5-Hydroxy-3-(3-hydroxypropyl)-2,2-dimethyl-7-(5-phenyl-2-pentyloxy)-3,4-dihydro-2H-benzopyran To a solution of 100 mg (0.21 mmole) methyl dl-3-[5-acetoxy-2,2-dimethyl-7-(5-phenyl-2-pentyloxy)-3,4-dihydro-2H-benzopyran-3-yl]propionate in 3.0 ml tetrahydrofuran was added 25 mg (0.66 mmole) lithium aluminum hydride in increments. The resulting mixture was stirred (nitrogen atmosphere) for 40 minutes, the reaction quenched with water, evaporated to dryness and the residue dissolved in ethyl acetate. The solution was washed with water (2×15 ml), brine (1×15 ml), dried over anhydrous magnesium sulfate and evaporated in vacuo to provide a residual oil, 66 mg. An additional 11 mg of oil was obtained by reworking the aqueous washes. The combined residual oils, 77 mg, were chromatographed on a column of silica gel, eluting with methylene chloride for seven fractions (15 ml/fraction), the same eluant containing 5% by volume ethyl acetate (10 fractions), 10% ethyl acetate (5 fractions) and ethyl acetate alone (7 fractions). Fractions 20–27 were combined and evaporated to dryness to afford 54 mg of the desired product.

$^1$H-NMR(CDCl$_3$)ppm(delta): 3.60 (t, 2H), 4.20 (m, 1H), 5.90 (s, 2H), 7.10 (s, 5H). Mass spectrum (m/e): 398 (M+).

The remaining methyl esters provided in Example 59 are reduced with lithium aluminum hydride by the above procedure to provide dihydroxy compounds of the formula

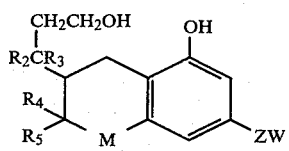

where R$_2$–R$_5$, M, Z and W are as defined in Example 54.

EXAMPLE 61 dl-5-Acetoxy-3-(3-hydroxypropyl)-2,2-dimethyl-7-(5-phenyl-2-pentyloxy)-3,4-dihydro-2H-benzopyran To a solution of 3.177 g (7.96 mmole) dl-5-hydroxy-3-(3-hydroxypropyl)-2,2-dimethyl-7-(5-phenyl-2-pentyloxy)-3,4-dihydro-2H-benzopyran in 40 ml methylene chloride, under a nitrogen atmosphere, was added 805 mg (7.96 mmole) triethylamine, the mixture stirred for 15 minutes and cooled to 0° C. At this temperature, 970 mg (7.79 mmole) 4-dimethylaminopyridine in 3 ml methylene chloride followed by 813 mg (7.96 mmole) acetic anhydride was added and the resulting mixture stirred at 0°–5° C. for one hour. After allowing the mixture to warm to room temperature, it was extracted three times with 30 ml portions methylene chloride. The extracts were washed with saturated sodium bicarbonate solution, dried (MgSO$_4$) and evaporated to obtain 4.158 g of crude oil. The crude product was purified by column chromatography on silica gel eluting with ethyl ether/methylene chloride 3:97 (v/v) for 7 fractions and 1:9 (v/v) for 43 fractions. Fractions 18–27 contained the diacetate. Fractions 28–45 containing desired monoacetate were combined and evaporated to afford 1.823 g of the title compound. $^1$H-NMR(CDCl$_3$)ppm(delta): 2.20 (s, 3H), 3.50 (t, 2H), 6.20 (m, 2H), 7.10 (s, 5H).

Employing the above procedure the remaining dihydroxy compounds of Example 60 are monoacetylated to provide compounds of the formula

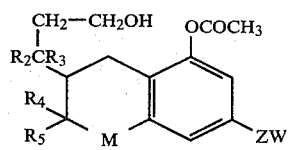

where R$_2$–R$_5$, M, Z and W are as defined in Example 54.

EXAMPLE 62 dl-3-(3-Cyanopropyl)-5-hydroxy-2,2-dimethyl-7-(5-phenyl-2-pentyloxy)-3,4-dihydro-2H-benzopyran A. dl-5-Acetoxy-3-(3-methanesulfonyloxypropyl)-2,2-dimethyl-7-(5-phenyl-2-pentyloxy)-3,4-dihydro-2H-benzopyran To 1.823 g (4.15 mmole) dl-5-acetoxy-3-(3-hydroxypropyl)-2,2-dimethyl-7-(5-phenyl-2-pentyloxy)-3,4-dihydro-2H-benzopyran was added 20 ml of pyridine, the mixture stirred under nitrogen to affect solution and cooled to 5° C. Methanesulfonyl chloride, 520 mg (4.56 mmole), was added, the resulting mixture stirred at 5°–10° C. for 20 minutes, then allowed to warm to room temperature and stirred for an additional 50 minutes. The mixture was concentrated in vacuo and the residual oil taken up in ethyl acetate, washed twice with water, once with brine and the organic layer dried over anhydrous magnesium sulfate. After evaporation of solvent in vacuo the desired product was obtained as an oil, 1.999 g.

$^1$H-NMR(CDCl$_3$)ppm(delta): 2.20 (s, 2H), 2.95 (s, 3H), 4.20 (m, 1H), 6.20 (m, 2H), 7.20 (s, 5H).

B. A mixture of 1.857 g (4.22 mmole) of the mesylate obtained in Part A, above, 2.8 g (43.0 mmole) potassium cyanide, 43.5 mg (0.252 mmole) potassium iodide and 40 ml of dimethylformamide/water (9:1 by weight) was heated at 90° C. for 1.5 hours. The solvent was evaporated in vacuo, the residue extracted three times with methylene chloride, the extracts washed with water, brine and dried over anhydrous magnesium sulfate. After evaporation of solvent 1.655 g of oil was obtained. The oil was purified on a short silica gel column, eluting with ethyl acetate. The product-containing fractions were combined and evaporated to provide 1.407 g (82%) of the title compound as an oil. Rf 0.62 on silica gel TLC, solvent-ethyl ether, develop with vanillin/heat. Mass spectrum (m/e): 407 (M+), 261 (M-146), 139 (base).

Employing the above procedures the remaining compounds provided in Example 61 are converted to nitriles of the formula

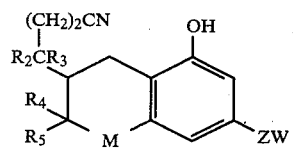

where R$_2$–R$_5$, M, Z and W are as defined in Example 54.

EXAMPLE 63 dl-4-[5-Hydroxy-2,2-dimethyl-7-(5-phenyl-2-pentyloxy)-3,4-dihydro-2H-benzopyran-3-yl]butyric acid A mixture of 1.407 g (3.45 mmole) dl-3-(3-cyanopropyl)-5-hydroxy-2,2-dimethyl-7-(5-phenyl-2-pentyloxy)-3,4-dihydro-2H-benzopyran, 50 ml methanol and 26 ml 1N sodium hydroxide was heated at reflux overnight. The methanol was evaporated and the aqueous residue washed with methylene chloride. The methylene chloride washings were extracted with 10 ml 1N sodium hydroxide, the combined aqueous layers acidified with hydrochloric acid, extracted with methylene chloride and the organic extracts dried over anhydrous magnesium sulfate. The solvent was evaporated in vacuo to obtain 1.189 g of the title acid as a foam. Mass spectrum (m/e): 426 (M+) 280 (M-146), 139 (base).

By means of the above procedure the remaining compounds provided in Example 62 form carboxylic acids of the formula

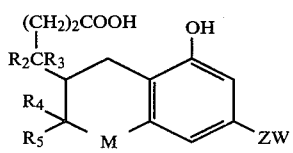

where $R_2$–$R_5$, M, Z and W are as defined in Example 54. The products wherein M is NH are isolated by isoelectric precipitation as described in Example 54.

EXAMPLE 64 dl-5-Hydroxy-3-(4-hydroxybutyl)-2,2-dimethyl-7-(5-phenyl-2-pentyloxy)-3,4-dihydro-2H-benzopyran To a solution of 1.238 g (2.9 mmole) dl-3-[5-hydroxy-2,2-dimethyl-7-(5-phenyl-2-pentyloxy)-3,4-dihydro-2H-benzopyran-3-yl]butyric acid in 20 ml tetrahydrofuran under a nitrogen atmosphere was added, in increments, 165 mg (4.35 mmole) lithium aluminum hydride and the resulting mixture stirred for 30 minutes at room temperature. The reaction was quenched by addition of Glauber's salt ($Na_2SO_4.10H_2O$), 20 ml ethyl acetate and about one gram of a filter aid was added. After stirring for 30 minutes the mixture was filtered, the solids washed with cold ethyl acetate. The filter cake was slurried with hot ethyl acetate, filtered and the combined filtrates evaporated in vacuo to provide 852 mg of residual oil. The oil was purified by chromatography on a silica gel column, eluting with ethyl acetate to provide 653 mg of the title compound, Rf 0.75 on silica gel TLC (solvent-ethyl acetate, developed with vanillin/heat). Mass spectrum (m/e): 412 ($M^+$), 266 (M-146), 139 (base).

Similarly the remaining acids provided in Example 64 are reduced to dihydroxy compounds of the formula

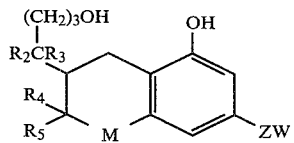

where $R_2$–$R_5$, M, Z and W are as defined in Example 54.

EXAMPLE 65 dl-3-(2-Cyanoethyl)-5-hydroxy-2,2-dimethyl-7-(5-phenyl-2-pentyloxy)-3,4-dihydro-2H-benzopyran A. Methyl dl-3-[5-acetoxy-2,2-dimethyl-7-(5-phenyl-2-pentyloxy)-3,4-dihydro-2H-benzopyran-3-yl]propionate, 4.68 g (0.01 mole), is dissolved in methanol and anhydrous ammonia is passed through the mixture at room temperature. The resulting mixture is heated at reflux for two hours while passing ammonia through it. After standing overnight the volatiles are removed by evaporation and the residue purified by column chromatography on silica gel to provide dl-3-[5-hydroxy-2,2-dimethyl-7-(5-phenyl-2-pentyloxy)-3,4-dihydro-2H-benzopyran-3-yl]propionamide.

B. The amide obtained above and 100 ml of thionyl chloride are heated at reflux for 18 hours. The reaction mixture is poured into ice-water, made alkaline by addition of sodium hydroxide solution, extracted with ether, the extracts dried ($MgSO_4$) and evaporated to dryness. The crude nitrile is purified by column chromatography on silica gel.

The remaining esters provided in Example 59 are converted to nitriles of the formula below in similar manner

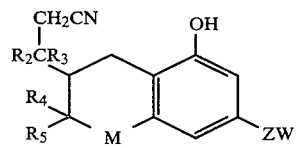

where $R_2$–$R_5$, M, Z and W are as defined in Example 54.

EXAMPLE 66

Lithium aluminum hydride reduction of the nitriles provided in Examples 62 and 65 by the procedure of Example 15 provides the corresponding primary amines of the formula

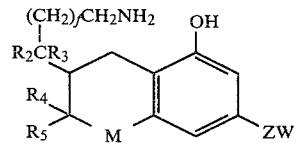

where f is 1 or 2 and $R_2$–$R_5$, M, Z and W are as defined in Examples 62 and 65.

EXAMPLE 67

Acylation of the above primary amines by the method of Example 16 and hydrolysis of the resulting amido ester by the method of Example 17 provides amides of the formula below

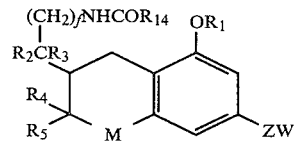

where $R_1$ is hydrogen, $R_{14}$ is as defined in Example 16 and f, $R_2$–$R_5$, M, Z and W are as defined in Example 66. The corresponding compounds wherein $R_1$ is defined in Example 18 are prepared from the above compounds by the procedure of Example 18.

EXAMPLE 68

5-Hydroxy-2,2-dimethyl-7-(1,1-dimethylheptyl)-3-(2-p-toluenesulfonylaminoethyl)-1,2,3,4-tetrahydroquinoline To 20 ml of methylene chloride is added 346 mg (1 mmole) dl-5-hydroxy-3-(2-aminoethyl)-7-(1,1-dimethylheptyl)-2,2-dimethyl-1,2,3,4-tetrahydroquinoline and 0.166 ml (1.2 mmole) triethylamine. The solution is cooled to $-20°$ C. and a solution of 191 mg (1 mmole) p-toluenesulfonyl chloride in 10 ml methylene chloride is added dropwise over ten minutes. The mixture is allowed to warm to 0° C., poured into ice/water and the layers separated. The aqueous layer is extracted with fresh methylene chloride, the combined organic layers washed with water, saturated sodium bicarbonate solution, brine and dried over anhydrous magnesium sulfate. Evaporation of solvent affords the crude product which is purified by chromatography on silica gel.

In like manner the remaining amines provided in Example 66 are reacted with sulfonyl chlorides of the formula $R_{17}SO_2Cl$ to provide compounds of the formula

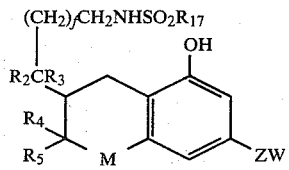

where f, $R_2$–$R_5$, M, Z and W are as defined in Example 66 and $R_{17}$ is as defined below.

$R_{17}$

CH$_3$
C$_2$H$_5$
(CH$_3$)$_2$CH
n-C$_4$H$_9$
n-C$_5$H$_{11}$
(CH$_3$)$_2$CHCH$_2$CH$_2$
C$_6$H$_5$
4-NH$_2$C$_6$H$_4$
3-FC$_6$H$_4$
2-ClC$_6$H$_4$
4-BrC$_6$H$_4$
4-ClC$_6$H$_4$
4-CH$_3$OC$_6$H$_4$
3-CH$_3$C$_6$H$_4$

EXAMPLE 69

Reaction of the methyl esters provided in Example 59 with ammonia or an amine, $R_{12}NH_2$, by the procedure of Example 20 provides amides of the formula below in which $R_{13}$ is hydrogen. Acetylation of the hydroxy carboxylic acids provided in Examples 54 and 63 by the procedure of Example 12 followed by conversion of the acetoxy acid to the corresponding acetoxy acid chloride and reaction of the latter with an amine $R_{12}R_{13}NH$ by the method of Example 21 affords amides of the formula below wherein f is 1 or 2, $R_2$–$R_5$, M, Z and W are as defined in Example 54 and $R_{12}$ and $R_{13}$ are as defined below

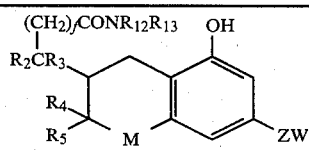

| $R_{12}$ | $R_{13}$ | $NR_{12}R_{13}$ |
|---|---|---|
| H | H | morpholino |
| CH$_3$ | H | piperidino |
| (CH$_3$)$_2$CH | H | pyrrolidino |
| (CH$_3$)$_2$CHCH$_2$ | H | N—methylpiperazino |
| n-C$_6$H$_{13}$ | H | N—ethylpiperazino |
| C$_6$H$_5$ | H | N—isopropylpiperazino |
| C$_6$H$_5$CH$_2$ | H | N—sec-butylpiperazino |
| CH$_3$ | CH$_3$ | N—n-butylpiperazino |
| CH$_3$ | C$_2$H$_5$ | |
| n-C$_3$H$_7$ | n-C$_3$H$_7$ | |
| (CH$_3$)$_2$CHCH$_2$CH$_2$ | (CH$_3$)$_2$CHCH$_2$CH$_2$ | |
| n-C$_6$H$_{13}$ | C$_2$H$_5$ | |
| C$_2$H$_5$ | C$_6$H$_5$ | |

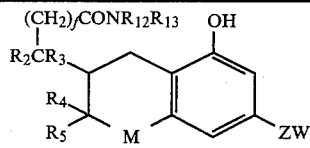

| $R_{12}$ | $R_{13}$ | $NR_{12}R_{13}$ |
|---|---|---|
| C$_6$H$_5$ | C$_6$H$_5$ | |
| CH$_3$ | C$_6$H$_4$CH$_2$ | |

EXAMPLE 70

The amides provided in Example 69 are reduced with lithium aluminum hydride by the method of Example 21A to provide amines of the formula

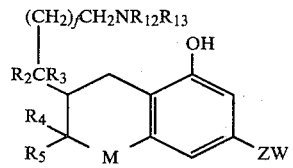

where f, $R_2$–$R_5$, $R_{12}$, $R_{13}$, M, Z and W are as defined in Example 69.

EXAMPLE 71

The N,N-dimethylamides provided in Example 69 are reacted with disiamylborane in tetrahydrofuran by the method of Example 22 to provide aldehydes of the formula

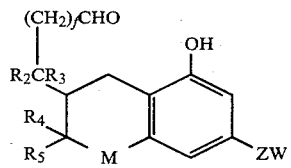

where f, $R_2$–$R_5$, M, Z and W are as defined in Example 69.

EXAMPLE 72

Treatment of the above aldehydes with a molar excess of Grignard reagent of formula $R_8MgBr$, $R_8MgCl$ or $R_8MgI$ by the methods of Examples 8 and 8A provides secondary alcohols of the formula

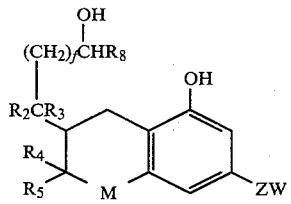

where f, $R_2$–$R_5$, M, Z and W are as defined in Example 69 and $R_8$ is as defined in Example 8A.

EXAMPLE 73

Oxidation of the above secondary alcohols by the method of Example 24 similarly provides the corresponding ketones of the formula

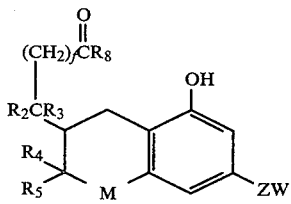

wherein f, $R_2$–$R_5$, $R_8$, M, Z and W are as defined in Example 72.

EXAMPLE 74

The ketones provided above are reacted with molar excess of Grignard reagent by the procedure of Example 25 to provide tertiary alcohols of the formula

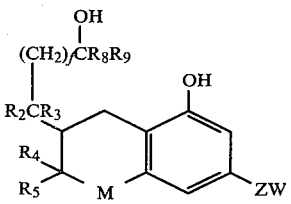

where f, $R_2$–$R_5$, M, Z and W are as defined in Example 69 and $R_8$ and $R_9$ are the same and are defined in Example 25.

EXAMPLE 75 dl-4-(2-Hydroxyethyl)-5-hydroxy-1,2-dimethyl-7-(4-thiaoctyl)-1,2,3,4-tetrahydroquinoline To a stirred solution of dl-4-(2-hydroxyethyl)-5-hydroxy-2-methyl-7-(4-thiaoctyl)-1,2,3,4-tetrahydroquinoline (337 mg, 1.0 mmole) in 5 ml acetonitrile cooled to 15° C. is added 0.5 ml aqueous formaldehyde and 100 mg sodium cyanoborohydride. Acetic acid is added to maintain a neutral pH until the reaction is complete. The reaction mixture is partitioned between water and ethyl ether, the organic phase dried ($MgSO_4$) and evaporated to afford the title compound.

In like manner the corresponding compounds wherein $R_6$ is ethyl, n-butyl, isobutyl, isoamyl, n-hexyl, $C_6H_5CH_2$, $C_6H_5(CH_2)_2$, $C_6H_5(CH_2)_3$ and $C_6H_5(CH_2)_4$ are obtained when the formaldehyde employed in the above procedure is replaced by an equimolar amount of acetaldehyde, n-butyraldehyde, isobutyraldehyde, isoamylaldehyde, $C_6H_5CHO$, $C_6H_5CH_2CHO$, $C_6H_5(CH_2)_2CHO$ or $C_6H_5(CH_2)_3CHO$, respectively.

Similarly the compounds provided above wherein $R_6$ is hydrogen are converted to the corresponding compounds wherein $R_6$ is methyl, ethyl, n-butyl, isobutyl, isoamyl, n-hexyl, $C_6H_5CH_2$, $C_6H_5(CH_2)_2$, $C_6H_5(CH_2)_3$ or $C_6H_5(CH_2)_4$ by the same procedure.

EXAMPLE 76

Methyl dl-3-[5-acetoxy-1-benzoyl-2,2-dimethyl-7-(2-heptyloxy)-1,2,3,4-tetrahydroquinolin-3-yl]propionate To a stirred solution of methyl dl-3-[5-acetoxy-2,2-dimethyl-7-(2-heptyloxy)-1,2,3,4-tetrahydroquinolin-3-yl]propionate (838 mg, 2 mmole) in 3 ml pyridine is added 0.42 g (3 mmole) benzoyl chloride in 5 ml chloroform. After stirring at reflux for one hour, the mixture is cooled, poured onto ice and extracted with ethyl ether. The combined ether extracts are washed with water, sodium bicarbonate, dried ($MgSO_4$) and evaporated to dryness to afford the desired product which is purified, if desired, by crystallization or column chromatography.

When the benzoyl chloride is replaced by an equimolar amount of acetyl chloride, propionyl chloride, isobutyryl chloride, valeryl chloride, 2-phenylacetyl bromide or 4-phenylbutyryl chloride, the corresponding compounds are obtained where $R_6$ is $CH_3CO$, $CH_3CH_2CO$, $(CH_3)_2CHCO$, $CH_3(CH_2)_3CO$, $C_6H_5CH_2CO$ or $C_6H_5(CH_2)_3CO$, respectively.

In like manner the compounds provided above wherein $R_6$ is hydrogen are converted to the corresponding benzoyl, acetyl, propionyl, butyryl, isobutyryl, valeryl, 2-phenylacetyl, 3-phenylpropionyl and 4-phenylbutyryl derivatives by reaction with the appropriate acyl chloride or acyl bromide. Use of carbobenzyloxy chloride affords the corresponding compounds wherein $R_6$ is $COOCH_2C_6H_5$. Of course when the 2- or 3-substituent of the tetrahydroquinoline starting material contains a primary amino, secondary amino or hydroxy group, the corresponding bis-amides or acyloxy amides are also obtained.

EXAMPLE 77 dl-4-(3-Oxobutyl)-1,2-dimethyl-5-(4-morpholinobutyryloxy)-7-(5-phenyl-2-pentyloxy)-1,2,3,4-tetrahydroquinoline To a solution of 614 mg (1.5 mmole) dl-4-(3-oxobutyl-5-hydroxy-2-methyl-7-(5-phenyl-2-pentyloxy)-1,2,3,4-tetrahydroquinoline in 40 ml of dry methylene chloride is added 315 mg (1.5 mmole) 4-morpholinobutyric acid hydrochloride, and the mixture is stirred at room temperature under a nitrogen atmosphere. To this is added dropwise 12.5 ml of 0.1 molar dicyclohexylcarbodiimide in methylene chloride and the resulting mixture is stirred for 24 hours. It is then cooled to 0° C., filtered, the filtrate extracted with 0.1N hydrochloric acid, the aqueous phase washed with ether, then made alkaline with sodium hydroxide solution and extracted with ether. The ether extracts are dried ($MgSO_4$) and evaporated to dryness to afford the title compound. The product is purified, if desired, by chromatography on silica gel.

Repetition of this procedure, but using an appropriate 5-hydroxy compound selected from those provided above and the appropriate alkanoic acid or acid of formula $R_{15}R_{16}N(CH_2)_p$—COOH.HCl affords the corresponding 5-$OR_1$ substituted compounds wherein $R_1$ is as defined in Example 18.

EXAMPLE 78 dl-Butyl 3-[4-(2-hydroxyethyl)-5-hydroxy-1,2-dimethyl-1,2,3,4-tetrahydroquinolin-7-yl]propyl sulfoxide Equimolar amounts of m-chloroperbenzoic acid and dl-4-(2-hydroxyethyl)-5-hydroxy-1,2-dimethyl-7-(4-thiaoctyl)-1,2,3,4-tetrahydroquinoline are added to a mixture of chloroform and acetic acid (2:1 v/v) and the mixture stirred at room temperature for one hour. The mixture is washed with water, the organic phase dried ($MgSO_4$) and evaporated to dryness at reduced pressure to afford the title compound.

In like manner the remaining thio ethers provided herein are oxidized to the corresponding sulfoxides.

EXAMPLE 79 dl-Butyl-3-[4-(2-hydroxyethyl)-5-hydroxy-1,2-dimethyl-1,2,3,4-tetrahydroquinolin-7-yl]propyl sulfone The procedure of Example 78 is repeated but using 2 equivalents of m-chloroperbenzoic acid as oxidizing agent per mole of tio ether reactant to give the title sulfone.

Similarly the remaining thio ethers provided herein are oxidized to the corresponding sulfones.

EXAMPLE 80

General Hydrochloride Acid Addition Salt Formation

Into an ethereal solution of the appropriate free base of formula (I), where one or more of M, $R_1$, and Q is a basic nitrogen containing group, is passed a molar excess of anhydrous hydrogen chloride and the resulting precipitate is separated and recrystallized from an appropriate solvent, e.g. methanol-ether.

Similarly, the free bases of formula (I) are converted to their corresponding hydrobromide, sulfate, nitrate, phosphate, acetate, butyrate, citrate, malonate, maleate, fumarate, malate, glycolate, gluconate, lactate, salicylate, sulfosalicylate, succinate, pamoate and tartarate salts.

EXAMPLE 81 dl-5-Hydroxy-4-(2-hydroxyethyl)-2,2-dimethyl-7-(1,1-dimethylheptyl)-3,4-dihydro-2H-benzopyran, 100 mg, is intimately mixed and ground with 900 mg of starch. The mixture is then loaded into telescoping gelatin capsules such that each capsule contains 10 mg of drug and 90 mg of starch.

EXAMPLE 82

A tablet base is prepared by blending the ingredients listed below:
Sucrose: 80.3 parts
Tapioca starch: 13.2 parts
Magnesium stearate: 6.5 parts
Sufficient dl-5-acetoxy-4-(2-acetylaminoethyl)-2,2-dimethyl-7-(1,1-dimethylheptyl)-3,4-dihydro-2H-benzopyran is blended into this base to provide tablets containing 0.1, 0.5, 1, 5, 10 and 25 mg of drug.

EXAMPLE 83

Suspensions of dl-5-hydroxy-3-(3-hydroxypropyl)-2,2-dimethyl-7-(5-phenyl-2-pentyloxy)-3,4-dihydro-2H-benzopyran are prepared by adding sufficient amounts of drug to 0.5% methylcellulose to provide suspensions having 0.05, 0.1, 0.5, 1, 5 and 10 mg of drug per ml.

EXAMPLE 84

5-Benzyloxy-4-cyano-2,2-dimethyl-7-(1,1-dimethylheptyl)-3,4-dihydro-2H-benzopyran A. A mixture of 5.0 g (12.3 mmole) 5-benzyloxy-2,2-dimethyl-7-(1,1-dimethylheptyl)-3,4-dihydro-2H-benzopyran-4-one and 20 ml benzene is stirred under nitrogen. To the resulting solution is added 2.04 ml trimethylsilylnitrile, 80 mg zinc iodide and starting continued at room temperature for three hours. Pyridine, 16 ml, and phosphorus oxychloride, 9.4 g, are added and the mixture heated at reflux for 3.5 hours, cooled to room temperature, poured onto a mixture of ice and 35 ml concentrated hydrochloric acid. The resulting mixture is extracted with ethyl acetate, dried (MgSO$_4$) and the solvent evaporated in vacuo to provide 5.63 g residual oil which is purified by chromatography on silica gel, eluting with hexane/ethyl ether. Evaporation of solvent from the product fractions gives 3.93 g 5-benzyloxy-4-cyano-2,2-dimethyl-7-(1,1-dimethylheptyl)-2H-benzopyran. Repeating the above procedure on a 5-fold scale gives 24.5 g of crude material which is purified on silica gel to provide 19.06 g of product.

$^1$H-NMR(CDCl$_3$)ppm(delta): 5.05 (s, 2H), 6.10 (s, 1H), 6.35 (s, 2H), 7.20 (m, 5H).

B. A mixture of 418 mg (1 mmole) of the unsaturated nitrile obtained in Part A, above, 485 mg magnesium turnings, 15 ml methanol and 5 ml tetrahydrofuran is stirred under nitrogen overnight at room temperature. The mixture is cooled in ice, water added to the flask to effect precipitation. The mixture is adjusted to pH 3.0 with hydrochloric acid and the clear solution extracted with ethyl acetate. The extracts are washed with water, brine and dried (MgSO$_4$). Evaporation of solvent at reduced pressure gives 422 mg crude material which is purified by chromatography on silica gel, eluting with hexane/ethyl ether. Evaporation of the combined product fractions yields 294 mg (70%) of the title compound.

$^1$H-NMR(CDCl$_3$)ppm(delta): 4.00 (t, 1H), 5.10 (s, 2H), 6.40 (s, 2H), 7.30 (m, 5H).

EXAMPLE 85

5-Benzyloxy-4-carboxamido-2,2-dimethyl-7-(1,1-dimethylheptyl)-3,4-dihydro-2H-benzopyran To 3.4 g (8.2 mmole) 5-benzyloxy-4-cyano-2,2-dimethyl-7-(1,1-dimethylheptyl)-3,4-dihydro-2H-benzopyran is added a solution of 40 g potassium hydroxide in 160 g ethylene glycol and 10 ml water. The mixture is heated at 150° C. under an argon atmosphere for 24 hours, diluted with water (700 ml), acidified to pH 5 and extracted with ethyl acetate. The combined extracts are washed with water, brine, dried (MgSO$_4$) and solvent evaporated to give 8.5 g crude product. The crude is purified by chromatography on silica gel, eluting with ethyl ether/hexane (1:4, then 1:1). The combined product fractions are evaporated to give 2.0 g of the desired amide. Fractions containing starting material were combined, evaporated to dryness, hydrolyzed further under the above conditions for 48 hours and worked up as before to give 1.5 g crude material which is purified on a silica gel column to afford an additional 1.0 g of amide and 550 mg of the corresponding carboxylic acid.

The combined amide fractions were crystallized from methylene chloride/hexane to yield 2.55 g of product, m.p. 117°–120° C.

$^1$H-NMR(CDCl$_3$)ppm(delta): 3.70 (t, 1H), 5.00 (s, 2H), 5.75 and 6.15 (broad singlets 1H+1H), 6.50 (s, 2H), 7.30 (m, 5H).

EXAMPLE 86

4-Carboxamido-5-hydroxy-2,2-dimethyl-7-(1,1-dimethylheptyl)-3,4-dihydro-2H-benzopyran A mixture of 1.6 g 5-benzyloxy-4-carboxamido-2,2-dimethyl-7-(1,1-dimethylheptyl)-3,4-dihydro-2H-benzopyran, 320 mg 10% palladium/carbon and 50 ml methanol is hydrogenated with shaking at 3 atmospheres pressure overnight. The catalyst is removed by filtration and the filtrate evaporated to afford 1.21 g solid which is crystallized from ethyl acetate to yield 520 mg product, m.p. 174.5°–175° C. An additional 220 mg of product is recovered from the mother liquors.

$^1$H-NMR(CDCl$_3$)ppm(delta): 2.10 (d, 2H), 3.65 (t, 1H), 4.80 (broad s, 3H), 6.30 (dd, 2H).

EXAMPLE 87

4-Cyano-5-hydroxy-2,2-dimethyl-7-(1,1-dimethylheptyl)-3,4-dihydro-2H-benzopyran

Hydrogenation of 5-benzyloxy-4-cyano-2,2-dimethyl-7-(1,1-dimethylheptyl)-3,4-dihydro-2H-benzopyran by the above procedure affords the title hydroxy nitrile, m.p. 142°–144° C.

$^1$H-NMR(CDCl$_3$)ppm(delta): 2.20 (d, 2H), 4.05 (t, 1H), 6.40 (m, 2H).

EXAMPLE 88

5-Hydroxy-4-methoxycarbonyl-2,2-dimethyl-7-(1,1-dimethylheptyl)-3,4-dihydro-2H-benzopyran A. 5-Benzyloxy-2,2-dimethyl-7-(1,1-dimethylheptyl)-3,4-dihydro-2H-benzopyran-4-carboxylic acid A mixture of 2.0 g 5-benzyloxy-4-cyano-2,2-dimethyl-7-(1,1-dimethylheptyl)-3,4-dihydro-2H-benzopyran, 20 g potassium hydroxide and 100 ml ethylene glycol are heated under nitrogen at reflux for 18 hours and cooled to ambient temperature. The mixture is acidified to pH 3 with concentrated hydrochloric acid, extracted with ethyl acetate and the extracts dried (MgSO$_4$). Evaporation of solvent gives an oil which is taken up in ethyl ether, washed with water, brine, dried (MgSO$_4$) and the solvent evaporated to give 2.09 g of crude solid. The crude was purified by chromatography on silica gel, eluting with ethyl ether/hexane. The combined product fractions are combined and solvent evaporated to afford 1.69 g of the product, m.p. 137°–138° C.

B. Methyl 5-benzyloxy-2,2-dimethyl-7-(1,1-dimethylheptyl)-3,4-dihydro-2H-benzopyran-4-carboxylate A solution of 550 mg of the above carboxylic acid dissolved in 20 ml dry ethyl ether is treated with a molar excess of diazomethane. The mixture is allowed to stand at room temperature for 15 minutes, washed with dilute sodium bicarbonate solution, dried (MgSO$_4$) and the ether evaporated to give 470 mg of methyl ester which was used in the next step without purification.

C. The product from Part B, above (470 mg), is mixed with 200 mg 10% palladium/carbon catalyst and 40 ml methanol. The mixture is hydrogenated with shaking at 3 atmospheres pressure for two hours. Removal of catalyst by filtration and evaporation of solvent gives 320 mg of crude product. This is purified by chromatography on silica gel, eluting with 1:1 hexane/ethyl ether to give 300 mg of the desired 5-hydroxy compound.

$^1$H-NMR(CDCl$_3$)ppm(delta): 2.10 (dd, 2H), 3.75 (s, 3H), 3.80 (t, 1H), 6.40 (s, 2H), 6.50 (s, 1H).

EXAMPLE 89

4-N-Acetylcarboximido-5-hydroxy-2,2-dimethyl-7-(1,1-dimethylheptyl)-3,4-dihydro-2H-benzopyran A. p-Nitrophenyl 5-benzyloxy-2,2-dimethyl-7-(1,1-dimethylheptyl)-3,4-dihydro-2H-benzopyran-4-carboxylate A mixture of 3.3 g (7.53 mmole) 5-benzyloxy-2,2-dimethyl-7-(1,1-dimethylheptyl)-3,4-dihydro-2H-benzopyran-4-carboxylic acid, 5.0 g (21.3 mmole) p-nitrophenyl trifluoroacetate and 100 ml dry pyridine, under nitrogen, is stirred at room temperature for three hours. The pyridine is evaporated in vacuo, ethyl ether is added to the residue and this is washed with 1N sodium hydroxide, water, 10% hydrochloric acid, brine, dried (MgSO$_4$) and the solvent evaporated to obtain 4.5 g crude oil. This is taken up in pentane and cooled to obtain 3.38 g of crystals, m.p. 87°–87.5° C.

B. 4-N-Acetylcarboximido-5-benzyloxy-2,2-dimethyl-7-(1,1-dimethylheptyl)-3,4-dihydro-2H-benzopyran To 301 mg (5.1 mmole) acetamide is added 35 ml dry tetrahydrofuran and nitrogen passed through the solution while adding 103 mg sodium hydride (99%) (4.3 mmole). The resulting mixture is stirred overnight under nitrogen, 400 mg (0.716 mmole) of the p-nitrophenyl ester provided in Part A is added and stirring is continued for one hour at room temperature. The mixture is poured onto ice/water, adjusted to pH 3.0 with 10% hydrochloric acid and extracted with ethyl acetate. The extracts are washed with brine, saturated sodium bicarbonate solution, brine again and dried (MgSO$_4$). Evaporation of solvent yields 416 mg crude solid. The crude is taken up in methylene chloride, washed with sodium bicarbonate solution, brine, dried (MgSO$_4$) and solvent evaporated to afford 331 mg foam. Upon addition of hexane, crystals are precipitated, 249 mg. Treatment of this with hot hexane gives 216 mg upon cooling and filtration, m.p. 157°–158° C.

$^1$H-NMR(CDCl$_3$)ppm(delta): 2.20 (s, 3H), 3.80 (t, 1H), 5.0 (s, 2H), 6.50 (s, 2H), 7.30 (s, 5H), 8.10 (s, 1H).

C. The product from Part B, above, 216 mg, 45 mg 5% palladium/carbon and 25 ml ethyl acetate is shaken under hydrogen at atmospheric pressure for 2.5 hours. Filtration and evaporation of the filtrate affords 158 mg of product, m.p. 146°–147° C.

D. Repeating the procedure of Part B, above, with the appropriate amide of formula R$_{19}$CONH$_2$, sulfonamide of formula R$_{17}$SO$_2$NH$_2$ or urea in place of acetamide and hydrogenation of the resulting product by the method of Part C, above, affords the corresponding imido compounds of the formula below

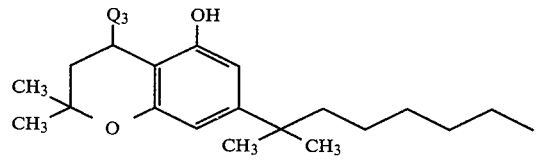

where Q$_3$ is CONHCOR$_{19}$, CONHSO$_2$R$_{17}$ or CONHCONH$_2$ and R$_7$ and R$_{17}$ are as shown below.

| Q$_3$ = CONHCOR$_{19}$: | |
|---|---|
| R$_{19}$ | Comment |
| CH(CH$_3$)$_2$ | M.P. 143–148° C. |
| C(CH$_3$)$_3$ | Mass spectrum, m/e: M$^+$ 431 base 360 |
| | $^1$H—NMR (CDCl$_3$) ppm (delta): 4.05 (t, 1H), 6.50 (m, 2H), 7.1 (s, 1H) |
| C$_6$H$_5$ | M.P. 172–173° C. |
| C$_6$H$_5$CH(CH$_3$) (diastereomer A) | M.P. 141–146° C. |
| | Mass spectrum, m/e: M$^+$ 479 |
| | $^1$H—NMR (DCCl$_3$) ppm (delta): 3.85 (t, 1H), 4.3 (q, 1H), 6.2 (m, 2H), 7.2 (s, 5H) |
| C$_6$H$_5$CH(CH$_3$) (diastereomer B) | M.P. 144–149° C. base 105 |
| | $^1$H—NMR (CDCl$_3$) ppm (delta): 3.90 (t, 1H), 4.40 (q, 1H), 6.35 (m, 2H), 7.25 (s, 5H) |
| C$_6$H$_5$CH$_2$ | — |
| n-C$_4$H$_9$ | — |
| Q$_3$ = CONHCONH$_2$ | M.P. 154–158° C. |
| | Mass spectrum, m/e: M$^+$ 390 (M—NH$_3$) 373 |
| Q$_3$ = CONHSO$_2$R$_{17}$: | |

-continued

| R$_{17}$ | Comment |
| --- | --- |
| CH$_3$ | M.P. 155–156° C. |
| | Mass spectrum, m/e: M$^+$ 425 |
| | base 303 |
| C$_2$H$_5$ | — |
| (CH$_3$)$_2$CH | — |
| CH$_3$(CH$_2$)$_4$ | — |
| CH$_3$(CH$_2$)$_5$ | — |
| (CH$_3$)$_2$CH(CH$_2$)$_3$ | — |
| C$_6$H$_5$CH$_2$ | — |
| 4-CH$_3$C$_6$H$_4$ | — |
| C$_6$H$_5$ | — |
| 2-ClC$_6$H$_4$ | — |
| 4-BrC$_6$H$_4$ | — |
| 3-FC$_6$H$_4$ | — |
| 4-NH$_2$C$_6$H$_4$ | — |
| 3-CH$_3$OC$_6$H$_4$ | — |

EXAMPLE 90

5-Hydroxy-4-(5-tetrazolyl)-2,2-dimethyl-7-(1,1-dimethylheptyl)-3,4-dihydro-2H-benzopyran Finely ground sodium azide (325 mg, 5 mmole) is added to a solution of 5-acetoxy-4-cyano-2,2-dimethyl-7-(1,1-dimethylheptyl)-3,4-dihydro-2H-benzopyran (1.855 g, 5 mmole) in 10 ml ethanol-free chloroform containing 271 mg (2 mmole) N-methylpiperidine hydrochloride and 5 drops of N-methylpiperidine. The mixture is heated at reflux for one hour, another 2 mmoles of N-methylpiperidine hydrochloride is added, refluxing is continued for one hour and the mixture is allowed to stand overnight at room temperature. The mixture is partitioned between chloroform and aqueous sodium carbonate solution, the aqueous phase is adjusted to pH 5 and extracted again with chloroform. The combined organic layers are washed with water, dried (MgSO$_4$) and the solvent evaporated in vacuo to afford the title compound.

In like manner any of the nitriles provided above are converted to the corresponding 5-tetrazolyl derivative by the above procedure.

EXAMPLE 91

5-Hydroxy-2,2-dimethyl-7-(1,1-dimethylheptyl)-3,4-dihydro-2H-benzopyran-4-hydroxamic acid A. 5-Hydroxy-2,2-dimethyl-7-(1,1-dimethylheptyl)-3,4-dihydro-2H-benzopyran-4-carboxylic acid A mixture of 5.0 g. of 5-benzyloxy-2,2-dimethyl-7-(1,1-dimethylheptyl)-3,4-dihydro-2H-benzopyran-4-carboxylic acid (prepared by the method of Example 88, Part A), 500 mg. 5% palladium-on-carbon catalyst and 150 ml. ethyl acetate is hydrogenated for 18 hours by the procedure of Example 86. After removal of catalyst and evaporation of solvent 4.25 g. of foam is obtained. Purification by silica gel chromatography, eluting with 2:1 hexane/ethyl ether affords 1.84 g. of product, M.P. 147°–148° C.

B. p-Nitrophenyl-5-hydroxy-2,2-dimethyl-7-(1,1-dimethylheptyl)-3,4-dihydro-2H-benzopyran-4-carboxylate A mixture of 4.25 g. (12.3 mmole) of the product of Part A, 8.67 g. (37 mmole) p-nitrophenyltrifluoroacetate and 50 ml. dry pyridine is stirred for 65 hours at room temperature. The mixture is evaporated to remove pyridine and the residue is worked up as described in Example 89, Part A, to obtain 5.085 g. (88%) of the desired ester; $^1$H-NMR (CDCl$_3$) ppm (delta): 6.5 (m, 2H), 6.7 (s, OH̲), 7.0–7.3 (m, 2H), 8.0–8.3 (m, 2H).

C. A mixture of 43 mg. (1.066 mmole) powdered sodium hydroxide in 10 ml. pyridine under a nitrogen atmosphere is stirred and warmed to effect solution then cooled to 0° C. To this is added 111 mg. (1.6 mmole) hydroxylamine hydrochloride and the mixture stirred for 15 minutes. A solution of 250 mg. (0.533 mmole) of the product of Part B in 3.0 ml. pyridine is added, the mixture allowed to warm to room temperature and stirred overnight. The pyridine is evaporated, the residue taken up in water and extracted with ethyl acetate. The combined extracts are washed with water and saturated brine and dried (MgSO$_4$). Evaporation of solvent affords 260 mg. of crude product which is charged to a column of 30 g. silica gel. Elution with 1:1 hexane/ethyl ether for 10 fractions then with ethyl acetate to elute the desired product. Evaporation of solvent (fractions 18–20) gave 158 mg. title compound. Mass spectrum (M$^+$ 363); $^1$H-NMR (CDCl$_3$) ppm (delta): 6.20 (4H, 2 aromatic, NH̲, OH̲), 10.0 (1H, exchanges with D$_2$O).

EXAMPLE 92

N-2-Pyridyl 5-hydroxy-2,2-dimethyl-7-(1,1-dimethylheptyl)-3,4-dihydro-2H-benzopyran-carboxamide A. N-2-Pyridyl 5-benzyloxy-2,2-dimethyl-7-(1,1-dimethylheptyl)-3,4-dihydro-2H-benzopyran-carboxamide A mixture of 1.118 g. (2.0 mmole) 4-nitrophenyl 5-benzyloxy-2,2-dimethyl-7-(1,2-dimethylheptyl)-3,4-dihydro-2H-benzopyran-carboxylate, 376 mg. (4.0 mmole) 2-aminopyridine and 4 ml. pyridine is placed in a sealed tube and heated for 18 hours at 155°–157° C. After cooling the tube is opened, the mixture concentrated to dryness in vacuo, the residue dissolved in ethyl ether, washed with 1N hydrochloric acid (25 ml.), 1N sodium hydroxide (3×25 ml.), water (2×25 ml.) and brine (25 ml.). The washed ether solution is dried (MgSO$_4$) and solvent evaporated to afford 966 mg. of oil. The oil is purified by chromatography on a silica gel column, eluting with hexane/methylene chloride (1:4), then with 15% ethyl ether in methylene chloride. The product-containing fractions are combined and solvent evaporated in vacuo to yield 823 mg. (80%) of the desired amide.

B. A mixture of 691 mg. each of the above amide and 10% Pd/C catalyst, 1.08 g. 1,4-cyclohexadiene and 25 ml. dry ethanol is hydrogenated by the procedure of Example 86. After removal of solvent in vacuo 680 mg. of crude debenzylated product is obtained. This is purified by column chromatography on silica gel, eluting with methylene chloride, then methylene chloride containing 10% ethyl ether and finally with ethyl ether alone to obtain 515 mg. (90%) of debenzylated material which is crystallized from ethyl acetate/hexane to afford 398 mg. (70%) of product, M.P. 166°–167° C.; mass spectrum, m/e: 424 (molecular ion), 119 base.

C. By employing the appropriate amine, ArNH$_2$, in place of 2-pyridylamine the following compounds are obtained by the above procedure.

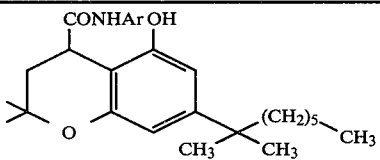

| Ar | M.P. °C. | Mass Spectra (m/e) | |
|---|---|---|---|
| (thiazole with CH3) | 238.5–239 | M+ base | 430 127 |
| (thiadiazole with CH3) | — | M+ base | 534 91 |
| (thiazole with CH3) | 208–209 | M+ base | 444 141 |
| (pyrazine) | — | M+ base | 425 96 |
| (isoxazole with CH3) | — | — | |
| C6H5 | — | — | |
| (triazole N=N/N–NH) | — | — | |

EXAMPLE 93

5-Hydroxy-2,2-dimethyl-7-(1,1-dimethylheptyl)-spiro[3,4-dihydro-2H-benzopyran-4,3'-pyrrolidin-2',5'-dione]

A. 5-Benzyloxy-4-ethoxycarbonylmethyl-4-methoxycarbonyl-2,2-dimethyl-7-(1,1-dimethylheptyl)-3,4-dihydro-2H-benzopyran Under anhydrous conditions, under a nitrogen atmosphere 5.31 ml. of 1.6 molar n-butyllithium in hexane is charged to a flask containing 80 ml. dry tetrahydrofuran at −78° C. A solution of 1.2 ml. (848 mg., 8.4 mmole) freshly distilled diisopropylamine is added dropwise and the resulting mixture stirred at −78° C. for three hours. Then a solution of 3.1 g. (6.85 mmole) methyl 5-benzyloxy-2,2-dimethyl-7-(1,1-dimethylheptyl)-3,4-dihydro-2H-benzopyran-4-carboxylate (Example 88, Part B) in 10 ml. THF is added slowly and the resulting mixture stirred for three hours at −78° C. To this is added dropwise 1.40 g. (8.4 mmole) ethyl bromoacetate and the mixture stirred for 15 minutes. The reaction is quenched by addition of acetic acid and the mixture allowed to warm to ambient temperature. The product was isolated by the procedure described in Example 3, Part A, to obtain 2.89 g. (78%) of the desired diester, $R_f$ 0.29, hexane/ethyl ether, 3:1.

B. 5-Benzyloxy-2,2-dimethyl-7-(1,1-dimethylheptyl)-spiro[3,4-dihydro-2H-benzopyran-4,3'-tetrahydrofuran-2',5'-dione]

A mixture of 2.355 g. (4.37 mmole) of the diester from Part A, above, 17.5 g. ethylene glycol, 1 ml. water and 8.74 g. potassium hydroxide is stirred under nitrogen at 150° C. for two hours then allowed to cool and stir overnight at room temperature. The mixture is poured into 350 ml. ice/water, acidified to pH 2–3 with 1N hydrochloric acid and extracted with ethyl acetate. The combined extracts are washed with water, brine and dried (MgSO4). Upon evaporation of solvent in vacuo 2.0 g. of residual dicarboxylic acid is obtained. In a separate flask 50 ml. of acetic anhydride is stirred under a nitrogen atmosphere while heating to reflux (140° C.). To this is added dropwise over four minutes a solution of the dicarboxylic acid (2.0 g) dissolved in 10 ml. ethyl acetate. The resulting mixture is stirred at 140° C. for ten minutes then allowed to cool to room temperature. The solvent is evaporated, the residue taken up in ethyl ether, washed with water, brine and dried (MgSO4). Evaporation of solvent affords 1.9 g. of light brown solid. 1H-NMR (CDCl3) ppm (delta): 3.15 doublet, 5.1 singlet, 6.25 singlet and 7.3 singlet; infrared (CHCl3): 1787 cm−1 (anhydride C=O).

C. A mixture of 100 mg. (0.209 mmole) of the product obtained in Part B and 125 mg. (2.08 mmole) urea is heated under nitrogen at 200° C. for 20 minutes and allowed to cool. The solidified reaction mixture is dissolved in ethyl ether, washed with water, brine and dried (MgSO4). Evaporation of solvent yielded 67 mg. of the 5-benzyl ether of the title compound which is taken up in 15 ml. ethyl acetate and hydrogenated over 50 mg. of 10% palladium/carbon catalyst. The catalyst is removed by filtration, solvent evaporated and the residue taken up in ethanol (15 ml.) and hydrogenated again with fresh catalyst at 2.5 atmospheres pressure. Isolation of product by filtration and evaporation of solvent affords 54 mg. of the solid title compound, M.P. 105°–120° C. which upon recrystallization gives crystals, M.P. 141°–143° C.; mass spectrum, molecular ion m/e 387; infrared (CHCl3) 1715 cm−1 (C=O).

EXAMPLE 94

5-Benzyloxy-2,2-dimethyl-7-(2-methylpropyl)-3,4-dihydro-2H-benzopyran-4-one

A. 3,5-Dihydroxyisobutylbenzene

A mixture of 66.2 g. 1-hydroxy-1-(3,5-dimethoxyphenyl)-2-methylpropane (from reaction of 3,5-dimethoxybenzaldehyde and isopropylmagnesium chloride in ethyl ether at 0°–5° C.) and 230 g. pyridine hydrochloride is heated under nitrogen at 190° C. for 3.5 hours. The resulting mixture is cooled to 30° C., poured into 500 ml. ice/water and the mixture acidified (pH 3.0) with 10% hydrochloric acid. The acid mixture is extracted three times with ethyl acetate, the extracts washed with water, brine, dried (MgSO4) and the solvent evaporated in vacuo to provide 50.9 g of residual oil. This is taken up in methylene chloride, filtered and the solvent evaporated to provide 43 g. of crude 3,5-dihydroxyisobutenylbenzene which is purified by chromatography on a silica gel column (1200 g.) eluting with mixtures of ethyl ether/methylene chloride to yield 31.9 g. of purified olefin. 1H-NMR (CDCl3) ppm (delta): 1.75 (d, 6H), 5.95 (s, 1H), 6.05–6.35 (m, 3H), 6.50 (s, 2H).

To 16 g. of this olefin in 100 ml. ethyl acetate is added 1.6 g. 10% palladium/carbon and the mixture is hydrogenated at 3-4 atmospheres for 6 hours. Isolation of product in the usual manner affords 15.4 g. of material which is used in the next step. $^1$H-NMR (CDCl$_3$) ppm (delta): 0.85 (d, 6H), 2.20 (d, 2H), 6.15 (s, 3H), 6.60 (s, 2H).

B. 5-Hydroxy-2,2-dimethyl-7-(2-methylpropyl)-3,4-dihydro-2H-benzopyran-4-one

A mixture of 20.3 ml. methanesulfonic acid and 1.0 g. phosphorus pentoxide under nitrogen is heated to 70° C. and 2.1 g. (12.7 mmole) of the product of Part A in 5 ml. ethyl ether is added. To this is added 1.27 g. (12.7 mmole) 3,3-dimethylacrylic acid and the mixture is maintained at 70° C. for 15 minutes then poured into ice/water and extracted with ethyl acetate. After washing of the extracts with water and brine, the extracts are dried (MgSO$_4$) and evaporated to provide a residual oil. Purification on a silica gel column, eluting with methylene chloride affords 1.04 g. of the desired product, R$_f$ 0.75, CH$_2$Cl$_2$; $^1$H-NMR (CDCl$_3$) ppm (delta): 2.30 (d, 2H), 2.65 (s, 2H), 6.10-6.25 (m, 2H), 11.6 (s, 7H).

C. A mixture of 2.0 g. of the product of Part B, above, 50 ml. acetone and 5.55 g. powdered potassium carbonate is stirred for five minutes and 1.38 g. of benzyl bromide is added. The mixture is stirred at reflux for 16 hours, cooled, filtered and the filtrate evaporated to provide an oil which gives crystals from cold hexane, M.P. 77.5°-78° C., 1.49 g. $^1$H-NMR (CDCl$_3$) ppm (delta): 2.30 (d, 2H), 2.60 (s, 2H), 5.04 (s, 2H), 6.25 (s, 2H), 7.05-7.60 (m, 5H).

EXAMPLE 95

5-Benzyloxy-4-cyano-2,2-dimethyl-7-(2-methylpropyl)-3,4-dihydro-2H-benzopyran

A. By the procedure of Example 84, Part A a mixture of 1.49 g. (4.43 mmole) 5-benzyloxy-2,2-dimethyl-7-(2-methylpropyl)-3,4-dihydro-2H-benzopyran-4-one, 10 ml. benzene, 0.8 ml. trimethylsilylnitrile, 30 mg. zinc iodide, 6 ml. pyridine and 3.5 g. phosphorus oxychloride are converted to 5-benzyloxy-4-cyano-2,2-dimethyl-7-(2-methylpropyl)-2H-benzopyran, 2.2 g. $^1$H-NMR (CDCl$_3$) ppm (delta): 2.25 (d, 2H), 5.05 (s, 2H), 6.15 (s, 1H), 6.23 (s, 2H), 7.05-7.60 (m, 5H).

B. Hydrogenation of the above olefin by the method of Example 84, Part B, employing 1.94 g. magnesium turnings and 100 ml. methanol gives 12.3 g. of crude dihydro nitrile which is purified by silica gel chromatography, eluting with ethyl acetate/methylene chloride, 1:4. The product fractions yield 7.8 g. of the title compound. $^1$H-NMR (CDCl$_3$) ppm (delta): 3.85 (t, 1H), 5.04 (s, 2H), 6.20 (s, 2H), 7.05-7.60 (m, 5H).

EXAMPLE 96

4-Nitrophenyl 5-benzyloxy-2,2-dimethyl-7-(2-methylpropyl)-3,4-dihydro-2H-benzopyran-4-carboxylate A. 5-Benzyloxy-2,2-dimethyl-7-(2-methylpropyl)-3,4-dihydrobenzopyran-4-carboxylic acid A mixture of 7.8 g. (22.2 mmole) of the product of the preceding Example, 12.5 g. KOH pellets and 200 ml. ethylene glycol are reacted by the procedure of Example 88, Part A to provide 8.25 g. of crude acid which is purified by silica gel chromatography, eluting with ethyl ether/methylene chloride, 1:4, ether alone and finally methanol/ethyl ether, 1:9 affords 6.13 g. which gave crystals from methylene chloride/hexane, M.P. 152°-153° C.

B. A mixture of 3.0 g. (8.15 mmole) of the acid obtained in Part A, 2.87 g. (12.2 mmole) p-nitrophenyl trifluoroacetate and 40 ml. dry pyridine is stirred at room temperature for 60 hours. The pyridine is evaporated in vacuo, the residue washed with 1N hydrochloric acid (3×25 ml.), 1N sodium hydroxide (4×25 ml.), water, brine and dried (MgSO$_4$). Evaporation of solvent provides 4.0 g. of crude product as a foam which is crystallized from methylene chloride/hexane to give 3.67 g. of title compound, M.P. 125°-126° C.

EXAMPLE 97

5-Hydroxy-2,2-dimethyl-7-(2-methylpropyl)-3,4-dihydro-2H-benzopyran-4-carboxylic acid The title compound, M.P. 185°-187° C. is obtained by catalytic hydrogenolysis of the corresponding 5-benzyl ether provided in Example 96, Part A, employing methods described above.

EXAMPLE 98

A. Employing the methods of Examples 89 and 92, but starting with the p-nitrophenyl ester provided in Example 96 and the appropriate amide or urea, the following compounds are obtained in like manner.

| Q$_3$ | M.P. °C. |
|---|---|
| CONHCOCH$_3$ | 156-157 |
| CONHCOCH(CH$_3$)$_2$ | 117-120 |
| CONH$_2$ | 206-207 |
| CONHCOC$_6$H$_5$ | — |
| CONH—tetrazol-5-yl | — |
| CONHCO—(thiazol-CH$_3$) | — |
| CONHCOC(CH$_3$)$_3$ | — |
| CONHCOCH$_2$CH(CH$_3$)$_2$ | — |
| CONHSO$_2$CH(CH$_3$)$_2$ | — |
| CONHSO$_2$C$_6$H$_5$ | — |

EXAMPLE 99

A. Employing 3,3-dimethyl-6-(5-phenyl-2-pentyloxy)-8-benzyloxy-1-tetralone (provided in U.S. Pat. No. 4,188,495) as starting material in the procedure of Example 84, Part A affords a quantitative yield of the corresponding unsaturated nitrile, 8-benzyloxy-1-cyano-3,3-dimethyl-6-(5-phenyl-2-pentyloxy)-3,4-dihydronaphthalene as an orange oil.

B. The oil from Part A above is hydrogenated by the procedure of Example 84, Part B to provide the corresponding tetralin, 8-benzyloxy-1-cyano-3,3-dimethyl-6-(5-phenyl-2-pentyloxy)tetralin, in 89% yield as an orange oil.

C. The tetralin nitrile provided above is hydrolyzed in ethylene glycol with potassium hydroxide by the procedure of Example 88, Part A, to provide the corresponding acid, 8-benzyloxy-3,3-dimethyl-6-(5-phenyl-2-pentyloxy)-tetralin-1-carboxylic acid as a white foam in 39% yield.

D. A mixture of 1.6 g. of the product of Part C, above, 20 ml. methanol and 320 mg. 5% Pd/C catalyst is hydrogenated at three atmospheres pressure for three hours and the product isolated by filtration and evaporation of the filtrate to give 1.2 g. of colorless solid foam which is 92.5% pure mixture of diastereomers by HPLC analysis on a Zobax Sil (registered Trademark of E. I. duPont de Nemours and Co., Inc., Wilmington, Del.) column, 2% isopropyl alcohol in hexane at 1 ml./minute. $^1$H-NMR (CDCl$_3$) ppm (delta): 0.8 (s, 3H), 1.0 (s, 3H), 1.2 (d, 4H), 1.74 (m, 6H), 2.5 (m, 4H), 3.7 (m, 1H), 4.16 (m, 1H), 6.1 (s, 2H), 7.1 (s, 5H), 8.1 (broad s, 1H) which is in agreement with the structure for 8-hydroxy-3,3-dimethyl-6-(5-phenyl-2-pentyloxy)tetralin-1-carboxylic acid.

E. Reaction of the above acid (3.14 mmole) with p-nitrophenyl trifluoroacetate (3.45 mmole) in pyridine (15 ml.) by the method of Example 91, Part B gives 1.1 g. (69%) of p-nitrophenyl 8-hydroxy-3,3-dimethyl-6-(5-phenyl-2-pentyloxy)tetralin-1-carboxylate as a yellow oil.

F. Use of the benzyl ether provided in Part C, above, in the procedure of Part E, above, affords p-nitrophenyl-8-benzyloxy-3,3-dimethyl-6-(5-phenyl-2-pentyloxy)tetralin-1-carboxylate as an oil in 90% yield; TLC: R$_f$ 0.68 with hexane/ethyl acetate, 2:1 solvent.

EXAMPLE 100

8-Hydroxy-3,3-dimethyl-6-(5-phenyl-2-pentyloxy)tetralin-1-carboxamide

A. Reaction of 2.3 g. (3.9 mmole) p-nitrophenyl-8-benzyloxy-3,3-dimethyl-6-(5-phenyl-2-pentyloxy)tetralin-1-carboxylate in an excess of liquid ammonia at −70° C. for 30 minutes and evaporation of excess ammonia gives a yellow paste which upon silica gel chromatography eluting with 1:1 ethyl acetate/hexane yields 730 mg. of amide, R$_f$0.15 on TLC with 2:1 ethyl acetate/hexane solvent system. Starting material (1.15 g.) is also recovered.

B. Hydrogenations of the product of Part A in 50 ml. methanol with 400 mg. 5% Pd/C catalyst at 3 atmospheres pressure for 4.5 hours and work-up in the usual manner affords a crude product which is purified on a silica gel column using 2:1 ethyl acetate/hexane as solvent to give 130 mg. of title compound, as a white solid, M.P. 155°–157° C. $^1$H-NMR (CDCl$_3$) ppm (delta): 0.8 (s, 3H), 1.0 (s, 3H), 1.16 (d, 3H), 1.7 (m, 6H), 2.47 (m, 4H), 3.57 (m, 1H), 4.16 (m, 1H), 6.1 (d, 3H), 7.2 (s, 5H).

C. Reaction of 0.55 g. (1.1 mmole) p-nitrophenyl 8-hydroxy-3,3-dimethyl-6-(5-phenyl-2-pentyloxy)tetralin-1-carboxylate in 10 ml. tetrahydrofuran with an excess of methylamine (gas) at room temperature, pouring the resulting mixture into 10% hydrochloric acid, extracting with ethyl acetate and work-up in the usual manner affords 0.50 g. of the N-methyl amide: N-methyl 8-hydroxy-3,3-dimethyl-6-(5-phenyl-2-pentyloxy)tetralin-1-carboxamide as a foam. $^1$H-NMR (CDCl$_3$) ppm (delta): 0.8 (s, 3H), 1.0 (s, 3H), 1.2 (d, 4H), 1.7 (m, 6H), 2.53 (m, 6H), 3.6 (m, 1H), 4.23 (m, NH), 6.2 (d, 2H), 7.13 (s, 5H).

EXAMPLE 101

8-Hydroxy-3,3-dimethyl-6-(5-phenyl-2-pentyloxy)-tetralin-1-carbonyl urea

By reacting 1.2 g. (2 mmole) p-nitrophenyl 8-benzyloxy-3,3-dimethyl-6-(5-phenyl-2-pentyloxy)tetralin-1-carboxylate, 0.3 g. (5 mmole) urea and 0.248 g. (10 mmole) sodium hydride in 12 ml. dimethylsulfoxide at room temperature for one hour and isolation of product by the method of Example 89, Part B and removal of benzyl group by hydrogenolysis by the procedure of Example 89, Part C affords the pure title compound in 36% overall yield. $^1$H-NMR (CDCl$_3$) ppm (delta): 0.77 (s, 3H), 1.1 (m, 8H), 1.7 (m, 4H), 2.5 (m, 4H), 3.6 (m, 1H), 4.16 (m, 1H), 5.7 (s, 1H), 6.1 (s, 2H), 7.1 (s, 5H), 8.2 (s, 2H).

EXAMPLE 102

Reacting 1.1 g. (1.9 mmole) p-nitrophenyl 8-hydroxy-3,3-dimethyl-6-(5-phenyl-2-pentyloxy)tetralin-1-carboxylate, 1.0 g. (17 mmole) acetamide, 361 mg. (15 mmole) sodium hydride in 70 ml. tetrahydrofuran by the method of Example 89, Parts B and C, likewise provides 8-hydroxy-3,3-dimethyl-6-(5-phenyl-2-penthyloxy)-1-N-acetylcarboximide in 55% yield as a foam; $^1$H-NMR (CDCl$_3$) ppm (delta): 0.7 (s, 3H), 1.0 (s, 3H), 1.16 (d, 3H), 1.6 (m, 6H), 2.3 (s, 3H), 2.5 (m, 4H), 3.73 (m, 1H), 4.13 (m, 1H), 6.1 (s, 2H), 7.1 (s, 5H), 8.5 (NH).

EXAMPLE 103

Ethyl 3-[8-hydroxy-3,3-dimethyl-6-(5-phenyl-2-pentyloxy)tetralin-1-yl]-3-oxopropionate A solution of 0.50 g. (1 mmole) 8-benzyloxy-3,3-dimethyl-6-(5-phenyl-2-pentyloxy)tetralin-1-carboxylic acid in 5 ml. ethyl ether is cooled to 0° C. and 0.25 g. (1.2 mmole) phosphorus pentachloride is added. The mixture is stirred at 0° C. for 30 minutes then at room temperature for 30 minutes. Evaporation of ether in vacuo affords the acid chloride as a brown oil.

In a separate flask 0.5 ml. (3.4 mmole) diisopropylamine in 6 ml. tetrahydrofuran is cooled to −78° C. and 1.4 ml. of 2.1M n-butyllithium is added and the mixture allowed to warm to 0° C. and stirred at 0° C. for 30 minutes. The mixture is then cooled to −78° C. and 0.30 ml. (3.1 mmole) ethyl acetate (dry, distilled) is added and the mixture is stirred at −78° C. for 2.5 hours. To this is added the above acid chloride in 2 ml. tetrahydrofuran and the mixture is stirred at −78° C. for two hours. The reaction is quenched with water, warmed to room temperature, poured into 10% hydrochloric acid and the mixture extracted with ethyl ether. The extracts are washed with water, brine and dried (MgSO$_4$). Evaporation of solvent affords 0.55 g. of yellow oil which is purified by chromatography on silica gel with 3:1 hexane ethyl ether as solvent to afford 0.13 g. (24%) of the benzyl ether of the title compound which is hydrogenated by the method of Example 89, Part C, to yield 110 mg. of colorless oil which is further purified by silica gel chromatography: 61 mg. (56%). $^1$H-NMR (CDCl$_3$) ppm (delta): 0.8 (s, 3H), 1.07 (s, 3H), 1.2 (m, 7H), 1.7 (m, 5H), 2.53 (m, 4H), 3.5 (s, 2H), 3.8 (m, 2H), 4.13 (m, 2H), 6.13 (s, 2H), 6.5 (s, 1H), 7.13 (s, 5H). Mass spectrum (m/e): M+ 452.

EXAMPLE 104

3-[8-Hydroxy-3,3-dimethyl-6-(5-phenyl-2-pentyloxy)-tetralin-1-yl]-3-oxopropionitrile To a solution of 2.4 ml. of 2.1M n-butyllithium in 3.7 ml. tetrahydrofuran at −78° C. is added a solution of 0.26 ml. (5 mmole) acetonitrile in 3.7 ml. THF and the mixture is stirred for one hour at −78° C. A solution of 1.1 g. (2.0 mmole) p-nitrophenyl 8-benzyloxy-3,3-dimethyl-6-(5-phenyl-2-pentyloxy)tetralin-1-carboxylate in 3.7 ml. THF is added and stirring continued at −78° C. for 30 minutes. The reaction mixture is warmed to room temperature, quenched with 7 ml. 10% hydrochloric acid and extracted with ethyl ether. Isolation of product as in the preceding Example affords 1.13 g. of crude benzyl ether which gives 500 mg. of purified intermediate by silica gel chromatography: mass spectrum-molecular ion, 495.

Removal of the benzyl group by hydrogenolysis by the method of Example 89, Part C gives the pure title compound. $^1$H-NMR (CDCl$_3$) ppm (delta): 0.8 (s, 3H), 1.06 (s, 3H), 1.2 (m, 5H), 1.7 (m, 4H), 2.5 (m, 4H), 3.5 (s, 2H), 4.0 (m, 2H), 6.1 (s, 2H), 7.1 (s, 5H).

EXAMPLE 105

8-Hydroxy-1-trifluoroacetylaminomethyl-3,3-dimethyl-6-(5-phenyl-2-pentyloxy)tetralin To a suspension of 114 mg. (3 mmole) lithium aluminum hydride in 10 ml. ethyl ether at room temperature is added a solution of 1.36 g. (3.0 mmole) 8-benzyloxy-1-cyano-3,3-dimethyl-6-(5-phenyl-2-pentyloxy)tetralin in 10 ml. tetrahydrofuran and the mixture is heated at reflux for two hours. After cooling to 0° C. 30 ml. ether is added and the reaction is quenched by addition of 150 ml. water, 150 ml. sodium hydroxide. Another 450 ml. water is added, the mixture is stirred for 15 minutes, filtered, washing with ether and the separated organic layer is dried (MgSO$_4$) and concentrated to about 50 ml. volume. To this solution of crude amine 0.70 ml. triethylamine and 565 microliters (4.0 mmole) trifluoroacetic anhydride is added over a 15 minute period at room temperature. The mixture is then diluted with 50 ml. ether and washed with 10% hydrochloric acid (25 ml.), water (25 ml.), saturated sodium bicarbonate solution, brine and dried (MgSO$_4$). Evaporation of solvent and column chromatography of the residue on silica gel eluting with methanol/methylene chloride 1:9 gives 500 mg. of the benzyl ether of the title compound which is debenzylated by the method of Example 89, Part C, to afford 250 mg. of oil. Mass spectrum (m/e): 367, 337, 191, 91, 69. $^1$H-NMR (CDCl$_3$) ppm (delta): 0.7 (s, 3H), 0.8 (s, 3H), 1.1 (d, 3H), 1.2–2.0 (m, 6H), 2.0–3.0 (m, 7H), 4.0 (m, 1H), 5.8–6.0 (m, 2H), 6.1 (NH), 7.0 (s, 5H).

EXAMPLE 106

Employing the procedures of Examples 84–105 the following compounds are obtained in similar manner

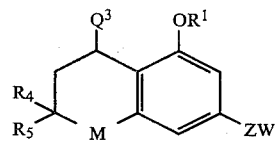

where M, R$_1$, R$_4$, R$_5$, Z and W are as previously defined and Q$_3$ is:

| Q$_3$ |
|---|
| 5-tetrazolyl |
| COOCH$_2$C$_6$H$_5$ |
| COOC$_2$H$_5$ |
| COOCH(CH$_3$)$_2$ |
| COO(CH$_2$)$_3$CH$_3$ |
| CONHOH |
| CONHCONH$_2$ |
| CONH$_2$ |
| CONHCH$_3$ |

-continued

| Q$_3$ |
|---|
| CONHCH$_2$CH(CH$_3$)$_2$ |
| CONH(CH$_2$)$_5$CH$_3$ |
| CONHCH(CH$_3$)$_2$ |
| CONHCH(CH$_3$)(CH$_2$)$_3$CH(CH$_3$)$_2$ |
| CONHC$_6$H$_5$ |
| CONHCH$_2$C$_6$H$_5$ |

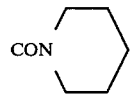

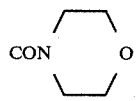

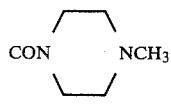

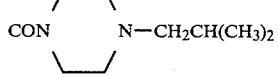

| |
|---|
| CONHCOCH$_3$ |
| CONHCOC$_2$H$_5$ |
| CONHCO(CH$_2$)$_2$CH$_3$ |
| CONHCOCH(CH$_3$)$_2$ |
| CONHCOCH$_2$CH(CH$_3$)$_2$ |
| CONHCOCH(CH$_3$)CH$_2$CH$_3$ |
| CONHCOC(CH$_3$)$_3$ |
| CONHCOC$_6$H$_5$ |
| CONHCOCH$_2$C$_6$H$_5$ |
| CONHCOCH$_2$CH$_2$C$_6$H$_5$ |
| CONHSO$_2$CH$_3$ |
| CONHSO$_2$CH(CH$_3$)$_2$ |
| CONHSO$_2$CH(CH$_3$)(CH$_2$)$_3$CH$_3$ |
| CONHSO$_2$CH(CH$_3$)CH$_2$CH$_3$ |
| CONHSO$_2$CH$_2$C$_6$H$_5$ |
| CONHSO$_2$(4-CH$_3$C$_6$H$_4$) |
| CONHSO$_2$(3-NH$_2$C$_6$H$_4$) |
| CONHSO$_2$(4-FC$_6$H$_4$) |
| CONHSO$_2$(2-ClC$_6$H$_4$) |
| CONHSO$_2$(3-CH$_3$OC$_6$H$_4$) |

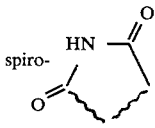

| |
|---|
| COCH$_2$CN |
| COCH$_2$COOH |
| COCH$_2$CO$_2$C$_2$H$_5$ |

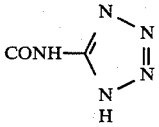

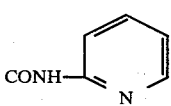

-continued

Q₃

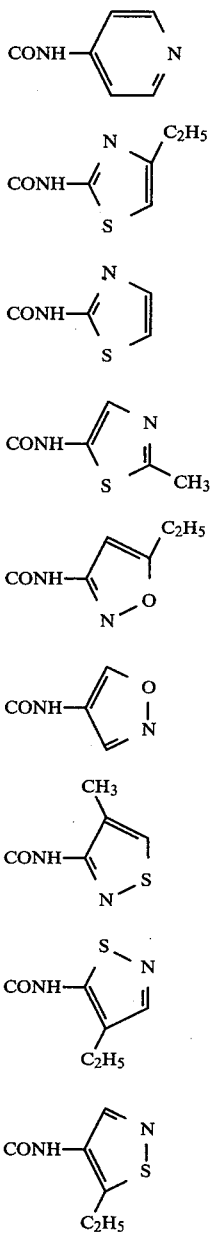

EXAMPLE 107

2-[8-Acetoxy-3,3-dimethyl-6-(5-phenyl-2-pentyloxy)tetralin-1-yl]acetic acid

To a solution of sodium methoxide prepared from 0.2 g. sodium metal and 32 ml. methanol is added a solution of 0.20 g. (0.53 mmole) of the lactone of 2-[8-hydroxy-3,3-dimethyl-6-(5-phenyl-2-pentyloxy)tetralin-1-yl]acetic acid and the mixture is stirred for 30 minutes. The methanol is evaporated in vacuo, the residue is cooled in ice and a cold solution of 6.4 ml. acetyl chloride in 12.8 ml. ethyl acetate is added and the resulting mixture stirred 15 minutes. The mixture is concentrated to dryness in vacuo, the residue taken up in fresh ethyl acetate, washed with water, brine and dried (MgSO₄) to yield 0.30 g. yellow oil. The oil is purified on a silica gel column using mixtures of methylene chloride and methanol as eluant to afford 110 mg. (47%) of title compound. ¹H-NMR (CDCl₃) ppm (delta): 0.8 (s, 3H), 1.03 (s, 3H), 1.23 (d, 4H), 1.7 (m, 6H), 2.3 (s, 3H), 2.5 (m, 4H), 2.9 (m, 1H), 3.13 (m, 1H), 4.2 (m, 1H), 6.4 (s, 2H), 7.13 (s, 5H).

EXAMPLE 108

2-[8-Hydroxy-3,3-dimethyl-6-(5-phenyl-2-pentyloxy)-tetralin-1-yl]acetamide

A solution of 0.76 g. (2 mmole) 2-[8-hydroxy-3,3-dimethyl-6-(5-phenyl-2-pentyloxy)tetralin-1-yl]acetic acid lactone in 10 ml. ethyl ether is added to an excess of liquid ammonia at −30° C. and the mixture stirred while warming to room temperature over two hours. Evaporation of solvent affords a solid white residue which is taken up in ethyl acetate, washed with water, brine and dried (MgSO₄). Evaporation of solvent yields 800 mg. (100%) of title compound, M.P. 67°-72° C. ¹H-NMR (CDCl₃) ppm (delta): 0.86 (s, 3H), 1.06 (s, 3H), 1.26 (d, 5H), 1.7 (m, 6H), 2.6 (m, 6H), 3.4 (m, 1H), 4.26 (m, 1H), 5.6 (m, 2H, N$\underline{H}$₂), 6.2 (m, 2H), 7.2 (s, 5H).

We claim:

1. A compound of the formula

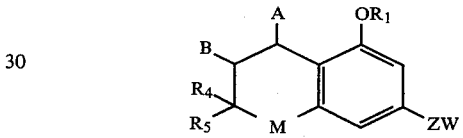

and pharmaceutically acceptable cationic and acid addition salts thereof;

wherein M is O, B is hydrogen and A is

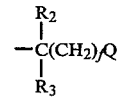

wherein f is zero or 1, R₂ and R₃ are each hydrogen, methyl or ethyl; and Q is a member selected from the group consisting of CO₂R₇, COR₈, C(OH)R₈R₉, CN, CONR₁₂R₁₃, CH₂NR₁₂R₁₃, CH₂NHCOR₁₄,

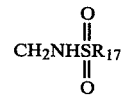

and 5-tetrazolyl;

A and OR₁ when taken together form

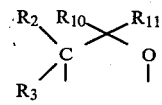

where R₁₀ is hydrogen and R₁₁ is hydroxy or alkoxy having from one to four carbon atoms or taken together R₁₀ and R₁₁ are an oxygen atom;

R₁ is a member selected from the group consisting of hydrogen, benzyl, benzoyl, alkanoyl having from one to five carbon atoms and —CO—(CH₂-

)$_p$—NR$_{15}$R$_{16}$ wherein p is 0 or an integer from 1 to 4; each of R$_{15}$ and R$_{16}$ when taken individually is selected from the group consisting of hydrogen and alkyl having from one to four carbon atoms; R$_{15}$ and R$_{16}$ when taken together with the nitrogen atom to which they are attached form a 5- or 6-membered heterocyclic ring selected from the group consisting of piperidino, pyrrolo, pyrrolidino, morpholino and N-alkylpiperazino having from one to four carbon atoms in the alkyl group;

R$_4$ is hydrogen, alkyl having from 1 to 6 carbon atoms or —(CH$_2$)$_z$—C$_6$H$_5$ wherein z is an integer from 1 to 4;

R$_5$ is hydrogen, methyl or ethyl;

R$_7$ is hydrogen, alkyl having from one to four carbon atoms or benzyl;

R$_8$ and R$_9$ are each hydrogen, alkyl having from one to four carbon atoms, phenyl or benzyl;

when taken separately, R$_{12}$ and R$_{13}$ are each hydrogen, alkyl having from one to six carbon atoms, phenyl or benzyl; R$_{12}$ and R$_{13}$ when taken together with the nitrogen atom to which they are attached form a 5- or 6-membered heterocyclic ring selected from the group consisting of piperidino, pyrrolidino, morpholino and N-alkylpiperazino having from one to four carbon atoms in the alkyl group;

R$_{14}$ is a member selected from the group consisting of hydrogen, alkyl having from one to five carbon atoms, trifluoromethyl, benzyl, furyl, thienyl, pyridyl, or R$_{18}$C$_6$H$_4$ where R$_{18}$ is H, NH$_2$, F, Cl, Br, CH$_3$, or OCH$_3$;

R$_{17}$ is alkyl having from one to six carbon atoms, benzyl or R$_{18}$C$_6$H$_4$;

Z is selected from the group consisting of
(a) alkylene having from one to nine carbon atoms;
(b) —(alk$_1$)$_m$—X—(alk$_2$)$_n$— wherein each of (alk$_1$) and (alk$_2$) is alkylene having from one to nine carbon atoms, with the proviso that the summation of carbon atoms in (alk$_1$) plus (alk$_2$) is not greater than nine; each of m and n is 0 or 1; X is selected from the group consisting of O, S, $$\overset{O}{\underset{O}{\overset{\|}{S}}} \text{ and } \overset{O}{\underset{O}{\overset{\|}{S}}};$$

and
W is selected from the group consisting of hydrogen, methyl, pyridyl, piperidyl,

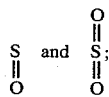

wherein W$_1$ is selected from the group consisting of hydrogen, fluoro and chloro; and

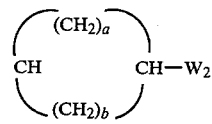

wherein W$_2$ is selected from the group consisting of hydrogen and

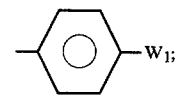

a is an integer from 1 to 5 and b is 0 or an integer from 1 to 5; with the proviso that the sum of a and b is not greater than 5 and the further proviso that when Z is —(alk$_1$)X, W is other than hydrogen.

2. A compound according to claim 1 wherein R$_1$ is hydrogen or alkanoyl having from one to five carbon atoms, R$_5$ is hydrogen or methyl and R$_4$ is hydrogen or alkyl having from one to six carbon atoms.

3. A compound according to claim 2 wherein R$_1$ is hydrogen or acetyl, Z is alkylene or —(alk$_1$)$_m$—O—(alk$_2$)$_n$— and W is hydrogen or phenyl.

4. A compound according to claim 1 wherein f is zero.

5. A compound according to claim 4 wherein R$_2$ and R$_3$ are each hydrogen, R$_4$ and R$_5$ are each methyl, Q is COOR$_7$, CHO, CH$_2$NHCOR$_{14}$ or C(OH)R$_8$R$_9$ where R$_8$ and R$_9$ are each hydrogen or methyl, Z is OCH(CH$_3$)CH$_2$CH$_2$CH$_2$ and W is phenyl.

6. A compound according to claim 5 wherein R$_1$ is hydrogen or COCH$_3$ and Q is CHO, CH$_2$OH or CH$_2$NHCOCH$_3$.

7. The compound according to claim 6 wherein Q is CH$_2$OH and R$_1$ is hydrogen.

8. A compound according to claim 4 wherein Q is CH$_2$OH, CH(CH$_3$)OH, C(CH$_3$)$_2$OH, CHO or COOR$_7$ where R$_7$ is methyl or ethyl; Z is C(CH$_3$)$_2$(CH$_2$)$_6$ and W is hydrogen.

9. A compound according to claim 8 wherein Q is CHO, C(CH$_3$)$_2$OH, CH(CH$_3$)OH or, CH$_2$OH.

10. The compound according to claim 9 wherein Q is CH$_2$OH, R$_1$ is hydrogen, R$_2$ and R$_3$ are each hydrogen and R$_4$ and R$_5$ are each methyl.

11. A method for producing analgesia in a mammalian subject which comprises administering to said subject an analgesia producing amount of a compound according to claim 1.

12. A pharmaceutical composition suitable for use as an analgesic which comprises a pharmaceutically acceptable carrier and an analgesia producing amount of a compound according to claim 1.

13. A method for prevention and treatment of nausea in a mammal subject to said nausea which comprises orally or parenterally administering to said mammal a compound according to claim 1 in an amount effective to prevent nausea.

14. A pharmaceutical composition suitable for use in prevention and treatment of nausea which comprises a pharmaceutically-acceptable carrier and a compound according to claim 1 in an amount effective to prevent nausea.

* * * * *